(12) United States Patent
Sparks et al.

(10) Patent No.: US 12,358,893 B2
(45) Date of Patent: Jul. 15, 2025

(54) METALLOENZYME INHIBITOR COMPOUNDS

(71) Applicant: Corxel Pharmaceuticals Hong Kong Limited, Causeway Bay (HK)

(72) Inventors: Steven Sparks, Apex, NC (US); Christopher M. Yates, Raleigh, NC (US)

(73) Assignee: Corxel Pharmaceuticals Hong Kong Limited, Causeway Bay (HK)

( * ) Notice: Subject to any disclaimer, the term of this patent is extended or adjusted under 35 U.S.C. 154(b) by 927 days.

(21) Appl. No.: 17/421,567

(22) PCT Filed: Jan. 8, 2020

(86) PCT No.: PCT/US2020/012786
§ 371 (c)(1),
(2) Date: Jul. 8, 2021

(87) PCT Pub. No.: WO2020/146532
PCT Pub. Date: Jul. 16, 2020

(65) Prior Publication Data
US 2022/0081420 A1    Mar. 17, 2022

Related U.S. Application Data

(60) Provisional application No. 62/789,832, filed on Jan. 8, 2019.

(51) Int. Cl.
*C07D 403/04* (2006.01)
*A61K 45/06* (2006.01)
*C07D 471/04* (2006.01)
*C07D 519/00* (2006.01)

(52) U.S. Cl.
CPC ............ *C07D 403/04* (2013.01); *A61K 45/06* (2013.01); *C07D 471/04* (2013.01); *C07D 519/00* (2013.01)

(58) Field of Classification Search
CPC .. C07D 403/04; C07D 471/04; C07D 519/00; A61K 45/06
See application file for complete search history.

(56) References Cited

U.S. PATENT DOCUMENTS

| | | |
|---|---|---|
| 4,309,551 A | 1/1982 | Schoenberger et al. |
| 4,738,851 A | 4/1988 | Schoenwald et al. |
| 4,882,150 A | 11/1989 | Kaufman |
| 4,921,475 A | 5/1990 | Sibalis |
| 5,008,110 A | 4/1991 | Benecke et al. |
| 5,077,033 A | 12/1991 | Viegas et al. |
| 5,087,240 A | 2/1992 | Sibalis |
| 5,088,977 A | 2/1992 | Sibalis |
| 5,106,863 A | 4/1992 | Hajos et al. |
| 5,163,899 A | 11/1992 | Sibalis |
| 5,164,189 A | 11/1992 | Farhadieh et al. |
| 5,254,346 A | 10/1993 | Tucker et al. |
| 5,290,561 A | 3/1994 | Farhadieh et al. |
| 5,336,168 A | 8/1994 | Sibalis |
| 5,352,456 A | 10/1994 | Fallon et al. |
| 5,403,841 A | 4/1995 | Lang et al. |
| 5,407,713 A | 4/1995 | Wilfong et al. |
| 5,521,222 A | 5/1996 | Ali et al. |
| 5,698,219 A | 12/1997 | Valdivia et al. |
| 5,776,445 A | 7/1998 | Cohen et al. |
| 5,800,807 A | 9/1998 | Hu et al. |
| 6,056,950 A | 5/2000 | Saettone et al. |
| 6,197,934 B1 | 3/2001 | DeVore et al. |
| 6,261,547 B1 | 7/2001 | Bawa et al. |
| 7,169,801 B2 | 1/2007 | Bressi et al. |
| 7,314,936 B2 | 1/2008 | Daun et al. |
| 7,855,202 B2 | 12/2010 | Vidal Juan et al. |
| 8,188,131 B2 | 5/2012 | Edge et al. |
| 8,188,282 B2 | 5/2012 | Alonso et al. |
| 8,629,147 B2 * | 1/2014 | Anikin ................ C07D 401/04 514/253.09 |
| 8,735,586 B2 | 5/2014 | Alonso et al. |
| 9,382,226 B2 | 7/2016 | Hoyt et al. |
| 10,085,984 B2 | 10/2018 | Sparks et al. |
| 10,538,511 B2 | 1/2020 | Sparks et al. |
| 11,040,034 B2 | 6/2021 | Sparks et al. |
| 11,136,309 B2 | 10/2021 | Sparks et al. |
| 2008/0027044 A1 | 1/2008 | Lewis et al. |
| 2008/0255085 A1 | 10/2008 | Arvidsson et al. |
| 2008/0312175 A1 | 12/2008 | Yao et al. |
| 2009/0010566 A1 | 1/2009 | Meijers |
| 2009/0105266 A1 | 4/2009 | Glatthar et al. |

(Continued)

FOREIGN PATENT DOCUMENTS

| | | |
|---|---|---|
| CN | 101321753 A | 12/2008 |
| CN | 102076665 A | 5/2011 |

(Continued)

OTHER PUBLICATIONS

A. M. Simonov and V. N. Komissarov, Translated from Khimiya Geterotsiklicheskikh Soedinenii, No. 6, pp. 826-828, Jun. 1975. Original article submitted May 27, 1974. (Year: 1975).*
Danupat Beukeaw, Kwanchanok Udomsasporn, and Sirilata Yotphan, J. Org. Chem. 2015, 80, 3447-3454) (Year: 2015).*
Deng et.al., J. Org. Chem. 2011, 76, 8262-8269 (Year: 2011).*
[Author Unknown], Auto-Immune Diseases. MedlinePlus. Jul. 21, 2014. http://www.nlm.nih.gov/medlineplus/autoimmunedisease.html [last accessed Oct. 29, 2018], 5 pages.
[Author Unknown], "Cancer", Medline Plus, Retrieved on Jul. 6, 2007, [Online] Retrieved from the Internet, http://www.nlm.nih.gov/medlineplus/cancer.html, 12 pages.
[Author Unknown], Compound Summary for CID 45792664. PubChem, NIH, U.S. National Library of Medicine, National Center for Biotechnology Information. Jun. 21, 2010. https://pubchem.ncbi.nlm.nih.gov/compound/45792664 [last accessed Apr. 24, 2018], 11 pages.

(Continued)

*Primary Examiner* — Valerie Rodriguez-Garcia
*Assistant Examiner* — Izabela Schmidt
(74) *Attorney, Agent, or Firm* — Choate, Hall & Stewart LLP; Charles E. Lyon; Kristen C. Buteau

(57) ABSTRACT

Provided are compounds having metalloenzyme modulating activity, and methods of treating diseases, disorders or symptoms thereof mediated by such metalloenzymes.

20 Claims, No Drawings

(56) References Cited

U.S. PATENT DOCUMENTS

| | | | |
|---|---|---|---|
| 2011/0236307 | A1 | 9/2011 | Jones |
| 2016/0074367 | A1 | 3/2016 | Rogers et al. |
| 2016/0207926 | A1* | 7/2016 | Achab .................. C07D 473/34 |
| 2018/0185362 | A1 | 7/2018 | Sparks et al. |
| 2018/0186773 | A1 | 7/2018 | Sparks et al. |
| 2019/0008861 | A1 | 1/2019 | Sparks et al. |
| 2020/0392112 | A1 | 12/2020 | Sparks et al. |
| 2021/0322409 | A1 | 10/2021 | Sparks et al. |
| 2022/0009907 | A1 | 1/2022 | Sparks et al. |

FOREIGN PATENT DOCUMENTS

| | | | |
|---|---|---|---|
| CN | 103626783 | A | 3/2014 |
| EP | 1604988 | A1 | 12/2005 |
| EP | 2624832 | B1 | 9/2017 |
| JP | 2011525894 | A | 9/2011 |
| RU | 2380368 | C2 | 1/2010 |
| WO | WO-0078761 | A1 * | 12/2000 ........... C07D 403/04 |
| WO | WO-03035065 | A1 | 5/2003 |
| WO | WO-2005111018 | A1 | 11/2005 |
| WO | WO-2006080821 | A1 | 8/2006 |
| WO | WO-2008009348 | A1 | 1/2008 |
| WO | WO-2009000413 | A1 | 12/2008 |
| WO | WO-2009045385 | A1 | 4/2009 |
| WO | WO-2009100438 | A2 | 8/2009 |
| WO | WO-2009156462 | A2 | 12/2009 |
| WO | WO-2010130796 | A1 | 11/2010 |
| WO | WO-2011061168 | A1 | 5/2011 |
| WO | WO-2012012478 | A1 | 1/2012 |
| WO | WO-2012177852 | A1 | 12/2012 |
| WO | WO-2013034047 | A1 | 3/2013 |
| WO | WO-2015163427 | A1 | 10/2015 |
| WO | WO-2015188369 | A1 | 12/2015 |
| WO | WO-2018118781 | A1 | 6/2018 |
| WO | WO-2018125799 | A2 | 7/2018 |
| WO | WO-2018125800 | A2 | 7/2018 |
| WO | WO-2020146532 | A1 * | 7/2020 ............. A61K 45/06 |

OTHER PUBLICATIONS

[Author Unknown], Compound Summary for CID 71940203. PubChem, NIH, U.S. National Library of Medicine, National Center for Biotechnology Information. Nov. 29, 2013. https://pubchem.ncbi.nlm.nih.gov/compound/71940203 [last accessed Apr. 24, 2018], 10 pages.

[Author Unknown], Definition of Cancer. MedicineNet.com. Sep. 18, 2004. http://www.medterms.com [last accessed Oct. 29, 2018], 1 page.

[Author Unknown], Infections: MedlinePlus. Jul. 6, 2016. https://medlineplus.gov/infections.html [last accessed Oct. 29, 2018], 10 pages.

[Author Unknown], Myeloproliferative disorders. University of Maryland Medical Center. Feb. 2, 2016. http://umm.edu/health/medical/altmed/condition/myeloproliferative-disorders [last accessed Oct. 29, 2018], 8 pages.

[Author Unknown], Neurological Disorders. Sep. 26, 2016. UCSF Medical Center https://www.ucsfhealth.org/conditions/neurological_disorders/ [last accessed Oct. 29, 2018], 1 page.

[Author Unknown], Search Results. Aurora Fine Chemicals. Date unknown. http://online.aurorafinechemicals.com/navigate.asp?pgNo=1 [last accessed Apr. 24, 2018], 25 pages.

[Author Unknown], Search Results. ChemSpace. Date unknown. https://chem-space.com/search/5ac4e53b-7bf084-266f2302-fbfd7af?currency=usd&per_page=48&uom=g [last accessed Apr. 24, 2018], 3 pages.

Azizi, Michel, et al. "Aldosterone synthase inhibition in humans", Nephrology Dialysis Transplantation (2013); 28(1): 36-43.

Beukeaw, Danupat, et al. "Iodine-catalyzed oxidative cross-coupling of indoles and azoles: regioselective synthesis of N-linked 2-(azol-1-yl) indole derivatives", The Journal of Organic Chemistry (2015); 8(7): 3447-3454.

Brown, Nancy J., "Contribution of aldosterone to cardiovascular and renal inflammation and fibrosis", Nature Reviews Nephrology (2013); 9(8): 459-469.

Database STN, CAS Registry No. 1913832-83-3, "1H-Benzimidazole-4-carbonitrile, 2-(3-ethyl-6-methyl-4-pyridazinyl)-1-methyl-", Chemical Abstracts Service, American Chemical Society; entered May 19, 2016; retrieved Oct. 14, 2022; 1 page.

Database STN, CAS Registry No. 1209120-48-8, "1H-Benzimidazole, 2-(3-chloro-6-methyl-4-pyridazinyl)-1-methyl-", Chemical Abstracts Service, American Chemical Society; entered Mar. 12, 2010; retrieved Oct. 14, 2022; 1 page.

Database STN, CAS Registry No. 1355233-87-2, "3-Pyridazinecarboxylic acid, 6-chloro-5-(1-methyl-1H-benzimidazol-2-yl)-", Chemical Abstracts Service, American Chemical Society; entered Feb. 3, 2012; retrieved Oct. 14, 2022; 1 page.

Database STN, CAS Registry No. 1912610-81-1, "1H-Benzimidazole-5-carbonitrile, 1-ethyl-2-(4-pyridazinyl)-", Chemical Abstracts Service, American Chemical Society; entered May 18, 2016; retrieved Oct. 14, 2022; 1 page.

Database STN, CAS Registry No. 1912610-84-4, "1H-Benzimidazole-5-carbonitrile, 1-propyl-2-(4-pyridazinyl)-", Chemical Abstracts Service, American Chemical Society; entered May 18, 2016; retrieved Oct. 14, 2022; 1 page.

Database STN, CAS Registry No. 1915555-78-0, "1H-Benzimidazole-5-carboxylic acid, 2-(3,6-dimethyl-4-pyridazinyl)-1-methyl-", Chemical Abstracts Service, American Chemical Society; entered May 22, 2016; retrieved Oct. 14, 2022; 1 page.

Database STN, CAS Registry No. 1915618-52-8, "1H-Benzimidazole-5-carbonitrile, 2-(3-ethyl-6-methyl-4-pyridazinyl)-1-methyl-", Chemical Abstracts Service, American Chemical Society; entered May 22, 2016; retrieved Oct. 14, 2022; 1 page.

Database STN, CAS Registry No. 1915618-64-2, "1H-Benzimidazole-5-carbonitrile, 1-(2-methylpropyl)-2-(4-pyridazinyl)-", Chemical Abstracts Service, American Chemical Society; entered May 22, 2016; retrieved Oct. 14, 2022; 1 page.

Database STN, CAS Registry No. 1917511-16-0, "1H-Benzimidazole-5-carbonitrile, 1-methyl-2-(4-pyridazinyl)-", Chemical Abstracts Service, American Chemical Society; entered May 25, 2016; retrieved Oct. 14, 2022; 1 page.

Database STN, CAS Registry No. 1917621-66-9, "1H-Benzimidazole-6-carbonitrile, 2-(3-ethyl-6-methyl-4-pyridazinyl)-1-methyl-", Chemical Abstracts Service, American Chemical Society; entered May 25, 2016; retrieved Sep. 24, 2021; 1 page.

Database STN, CAS Registry No. 1917959-75-1, "1H-Benzimidazole-6-carbonitrile, 1-methyl-2-(4-pyridazinyl)-", Chemical Abstracts Service, American Chemical Society; entered May 25, 2016; retrieved Oct. 14, 2022; 1 page.

Database STN, CAS Registry No. 1918181-17-5, "1H-Benzimidazole-4-carbonitrile, 2-(3,6-dimethyl-4-pyridazinyl)-1-methyl-", Chemical Abstracts Service, American Chemical Society; entered May 25, 2016; retrieved Oct. 14, 2022; 1 page.

Database STN, CAS Registry No. 1918800-31-3, "1H-Benzimidazole-5-carbonitrile, 2-(3,6-dimethyl-4-pyridazinyl)-1-ethyl-", Chemical Abstracts Service, American Chemical Society; entered May 26, 2016; retrieved Oct. 14, 2022; 1 page.

Database STN, CAS Registry No. 1919678-76-4, "1H-Benzimidazole-5-carbonitrile, 1-(1-methylethyl)-2-(4-pyridazinyl)", Chemical Abstracts Service, American Chemical Society; entered May 27, 2016; retrieved Oct. 14, 2022; 1 page.

Database STN, CAS Registry No. 1919763-04-4, "1H-Benzimidazole-6-carbonitrile, 2-(3,6-dimethyl-4-pyridazinyl)-1-methyl-", Chemical Abstracts Service, American Chemical Society; entered May 27, 2016; retrieved Oct. 14, 2022; 1 page.

Database STN, CAS Registry No. 1920995-91-0, "1H-Benzimidazole-5-carboxylic acid, 1-methyl-2-(4-pyridazinyl)-", Chemical Abstracts Service, American Chemical Society; entered May 30, 2016; retrieved Oct. 14, 2022; 1 page.

Database STN, CAS Registry No. 1921020-29-2, "1H-Benzimidazole-5-carbonitrile, 1-cyclopropyl-2-(4-pyridazinyl)-", Chemical Abstracts Service, American Chemical Society; entered May 30, 2016; retrieved Oct. 14, 2022; 1 page.

(56) References Cited

OTHER PUBLICATIONS

Database STN, CAS Registry No. 1921435-96-2, " 1H-Benzimidazole-1-acetic acid, 2-(3,6-dimethyl-4-pyridazinyl)", Chemical Abstracts Service, American Chemical Society; entered May 31, 2016; retrieved Oct. 14, 2022; 1 page.
Database STN, CAS Registry No. 1921438-70-1, "1H-Benzimidazole-5-carbonitrile, 2-(3,6-dimethyl-4-pyridazinyl)-1-methyl-", Chemical Abstracts Service, American Chemical Society; entered May 31, 2016; retrieved Oct. 14, 2022; 1 page.
Database STN, CAS Registry No. 1921449-39-9, "1H-Benzimidazole-6-carbonitrile, 2-(3,6-dimethyl-4-pyridazinyl)-", Chemical Abstracts Service, American Chemical Society; entered May 31, 2016; retrieved Oct. 14, 2022; 1 page.
Database STN, CAS Registry No. 1990187-60-4, "1H-Benzimidazole-4-carbonitrile, 1-methyl-2-(4-pyridazinyl)-", Chemical Abstracts Service, American Chemical Society; entered Sep. 9, 2016; retrieved Oct. 14, 2022; 1 page.
Deliyanti et al., "Neovascularization is attenuated with aldosterone synthase inhibition in rats with retinopathy", Hypertension (2012); 59: 607-13.
Deng, Xiaohu, et al., "Direct, metal-free amination of heterocyclic amides/ureas with NH-heterocycles and N-substituted anilines in POCl3", The Journal of Organic Chemistry (2011); 76(20): 8262-8269.
D'Ydewalle et al., "HDAC6 inhibitors reverse axonal loss in a mouse model of mutant HSPBI-induced Charcot-Marie-Tooth disease", Nat Med. (2011); 17(8): 968-74.
Escher, et al., "High aldosterone-to-renin variants of CYP11B2 and pregnancy outcome", Nephrol Dial Transplant (2009); 24(6): 1870-5.
European Patent Application No. 17887556.3, Office Action mailed Aug. 4, 2021; 4 pages.
Extended European Search Report, dated Jul. 24, 2020 for European Application No. 17887556.3.
Extended European Search Report, dated May 17, 2022 for European Application No. 20738530.3, 10 pages.
Extended European Search Report, dated May 28, 2020 for European Application No. 17886279.3.
Goeker, Hakan, et al., "Synthesis and potent antifungal activity against Candida species of some novel 1H-benzimidazoles", Journal of Heterocyclic Chemistry (2009); 46(5): 936-948.
Golub, et al., "Molecular classification of cancer: class discovery and class prediction by gene expression monitoring", Science, 1991, 286, 531-537.
Haggerty et al., "Domain-selective small-molecule inhibitor of histone deacetylase 6 (HDAC6)-mediated tubulin deacetylation", Proc Natl Acad Sci USA (2003); 100(8): 4389-94.
Houlden et al., "Mutations in the HSP27 (HSPBI) gene cause dominant, recessive, and sporadic distal HMN/CMT type 2", Neurology (2008); 71(21): 1660-8.
Hoyt et al., "Discovery of Benzimidazole CYP11B2 Inhibitors with in Vivo Activity in Rhesus Monkeys", ACS Med Chem Lett. (2015); 6(5): 573-8.
International Application No. PCT/US2017/068180; International Preliminary Report On Patentability mailed Jul. 2, 2019, 10 pages.
International Application No. PCT/US2017/068180; International Search Report and Written Opinion mailed Jul. 6, 2018, 16 pages.
International Application No. PCT/US2017/068190; International Preliminary Report On Patentability mailed Jul. 2, 2019, 7 pages.
International Application No. PCT/US2017/068190; International Search Report and Written Opinion mailed Jun. 29, 2018, 16 pages.
International Application No. PCT/US2020/012786; International Preliminary Report On Patentability mailed Jun. 16, 2021, 6 pages.
International Application No. PCT/US2020/012786; International Search Report and Written Opinion mailed May 20, 2020, 11 pages.
Kijima et al., "Small heat shock protein 27 mutation in a Japanese patient with distal hereditary motor neuropathy", J Hum Genet. (2005); 50(9): 473-6.
Lala et al., "Role of nitric oxide in tumor progression: Lessons from experimental tumors", Cancer and Metastasis Reviews (1998), 17: 91-106.
Li et al., "CYP11B2 expression in HSCs and its effect on hepatic fibrogenesis", World J Gastroenterol. (2000); 6(6): 885-7.
Li et al., "Novel mutations in the CYP11B2 gene causing aldosterone synthase deficiency", Mol Med Rep (2016); 13(4): 3127-32.
Meredith et al., "Discovery and in Vivo Evaluation of Potent Dual CY11B2 (Aldosterone Synthase) and CYP11B1 Inhibitors", ACS Medicinal Chemistry Letters (2013); 4: 1203-1207.
Milokhov et al., "Reaction of 2-Hetaryl-2-(tetrahydro-2-furanyliden)acetonitriles with 1,3-N,N-Binucleophiles", Synlett (2012); 23: 2063-2068.
Namsolleck, Pawel et al., "Aldosterone synthase inhibitors in cardiovascular and renal diseases", Nephrology Dialysis Transplantation (2014); 29(1): i62-i68.
Pacurari et al., "The Renin-Angiotensin-aldosterone system in vascular inflammation and remodeling", Int J Inflam (2014); 2014: 689360.
Papillon et al., "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem. (2015); 58: 9382-9394.
Pindur et al., "Cyclization reactions of 2,2'-bis-N-methylindolyl to potential protein kinase C inhibitors", Heterocycles (1994); 38(10): 2267-2276.
PubChem CID 3368479, Create Date: Sep. 7, 2005 (Sep. 7, 2005).
PubChem CID 91479648, Create Date: Mar. 17, 2015 (Mar. 17, 2015).
Rouffet, Matthieu, et al., "From sensors to silencers: Quinoline-and benzimidazole-sulfonamides as inhibitors for zinc proteases", Journal of the American Chemical Society (2010); 132(24): 8232-8233.
Sajith et al., "Design, synthesis and structure-activity relationship (SAR) studies of imidazo[4,5-b]pyridine derived purine isosteres and their potential as cytotoxic agents", European Journal of Medicinal Chemistry (2015); 89: 21-31.
Sajith et al., "Microwave enhanced Suzuki coupling: a diversity-oriented approach to the synthesis of highly functionalised 3-substituted-2-aryl/heteroaryl imidazo[4,5-b]pyridines," Tetrahedron Letters, (2012), 53: 1036-1041.
Savitha et al., "Palladium-Catalyzed Suzuki Cross-Coupling of 2-Halo-Deazapurines with Potassium Organotrifluoroborate Salts in the Regioselective Synthesis of Imidazo[4,5-b]pyridine Analogues", Aust. J. Chem (2016); 69: 618-630.
Supuran, Claudiu T., "Carbonic anhydrases: novel therapeutic applications for inhibitors and activators", Nature Reviews Drug discovery (2008); 7(2): 168-181.
WebMD, "Inherited Metabolic Disorders.: Types, Causes, Symptoms and Treatments," 2014, retrieved from http://www.webmd.com/a-to-z-guides/inherited-metabolic-disorder-types-and-treatments?page-2, 5 pages.
Xue et al., "Cu(i) recognition via cation-TT and methionine interactions in CusF", Nature Chemical Biology (2008); 4(2): 107-109.
Yang, Yang, et al., "Metalloprotein inhibitors for the treatment of human diseases", Current Topics in Medicinal Chemistry (2016); 16(4): 384-396.
Kolodyazhnaya, S. N. et al., Nitrogen-Containing Bisheterocyclic Systems, Chemistry of Heterocyclic Compounds, 6(2):224-227 (1970).

* cited by examiner

METALLOENZYME INHIBITOR COMPOUNDS

CROSS-REFERENCE TO RELATED APPLICATIONS

The present application is a U.S. National Phase of PCT/US2020/012786, filed Jan. 8, 2020 which claims priority under 35 U.S.C. § 119 (e) to U.S. Provisional Patent Application Ser. No. 62/789,832, filed Jan. 8, 2019. The contents of each of which are hereby incorporated by reference in their entireties.

BACKGROUND

Aldosterone is a steroid hormone secreted from the adrenal gland which binds and activates the mineralocorticoid receptor (MR). In the primary cells of the distal tubules and collecting ducts of the kidney, MR activation leads to sodium and water retention with excretion of potassium resulting in plasma volume expansion leading to increased blood pressure (BP). Excess aldosterone measured in circulation is termed primary aldosteronism (PA) and occurs when aldosterone production is dysregulated by the renin-angiotensin-aldosterone system (RAAS). PA was initially identified in patients with adrenal adenomas with recent evidence suggesting an increase in prevalence associated with obesity. PA is a common cause of secondary hypertension with the prevalence of PA ranging from 14-21% in patients with resistant hypertension (RHTN), a condition defined as BP remaining above goal despite the concurrent use of 3 antihypertensive agents of different classes including a diuretic agent. Recent studies have shown an association between excess aldosterone, RHTN, and obstructive sleep apnea (OSA) which is worsened by aldosterone-mediated fluid retention.

Local overproduction of aldosterone has been noted in several severe disease states even when no significant plasma elevation is observed. In patients with chronic congestive heart failure (CHF), aldosterone levels in failing heart tissue is higher than in peripheral plasma. In animal models of kidney disease, local production of aldosterone in the renal cortex is postulated to contribute to disease progression. In both these states, local elevated aldosterone levels contribute to harmful effects via both MR-dependent and MR-independent mechanisms including the generation of reactive oxygen species and endothelial dysfunction leading to inflammation and stimulation of cell growth and proliferation with upregulated collagen deposition leading to fibrosis.

Antagonists of MR, including spironolactone and eplerenone, have been extensively used to block the effects of aldosterone binding to MR. Significant reductions in morbidity and mortality in patients with heart failure or myocardial infarction have been demonstrated with these agents in combination with angiotensin-converting enzyme (ACE) inhibitors and diuretics (RALES & EPHESUS trials). Side effects including hyperkalemia are seen with both agents with the nonselective spironolactone also eliciting gynaecomastia via nonselective modulation of the progesterone and androgen receptors. Additionally, elevations of renin and aldosterone result from MR antagonism and thus the MR-independent (non-genomic) effects of aldosterone are exacerbated.

In contrast to MR antagonists, inhibition of CYP11B2 (aldosterone synthase), the key enzyme in aldosterone biosynthesis, should afford the beneficial effects of MR antagonism without the deleterious buildup of aldosterone leading to activation of MR-independent inflammatory and fibrotic states. CYP11B2 is a mitochondrial cytochrome P450 enzyme which converts 11-deoxycorticosterone to aldosterone. Selective inhibition of CYP11B2 represents a promising treatment for aldosterone related diseases.

The highly homologous metalloenzyme CYP11B1 (11-β-steroid-hydroxylase) catalyzes the formation of the primary glucocorticoid cortisol from 11-deoxycortisol. Given the high degree of homology between CYP11B2 and CYP11B1 (93%), the development of selective CYP11B2 inhibitors has been a significant challenge. The inhibitor Osilodrostat (LCI-699) was developed as a CYP11B2 inhibitor for the treatment of hypertension but was abandoned due to its potent inhibition of CYP11B1. Selective compounds which block the production of aldosterone via CYP11B2 without inhibition of cortisol production via CYP11B1 are described herein.

Living organisms have developed tightly regulated processes that specifically import metals, transport them to intracellular storage sites and ultimately transport them to sites of use. One of the most important functions of metals such as zinc and iron in biological systems is to enable the activity of metalloenzymes. Metalloenzymes are enzymes that incorporate metal ions into the enzyme active site and utilize the metal as a part of the catalytic process. More than one-third of all characterized enzymes are metalloenzymes.

The function of metalloenzymes is highly dependent on the presence of the metal ion in the active site of the enzyme. It is well recognized that agents which bind to and inactivate the active site metal ion dramatically decrease the activity of the enzyme. Nature employs this same strategy to decrease the activity of certain metalloenzymes during periods in which the enzymatic activity is undesirable. For example, the protein TIMP (tissue inhibitor of metalloproteases) binds to the zinc ion in the active site of various matrix metalloprotease enzymes and thereby arrests the enzymatic activity. The pharmaceutical industry has used the same strategy in the design of therapeutic agents. For example, the azole antifungal agents fluconazole and voriconazole contain a 1-(1,2,4-triazole) group that binds to the heme iron present in the active site of the target enzyme lanosterol demethylase and thereby inactivates the enzyme. Another example includes the zinc-binding hydroxamic acid group that has been incorporated into most published inhibitors of matrix metalloproteinases and histone deacetylases. Another example is the zinc-binding carboxylic acid group that has been incorporated into most published angiotensin-converting enzyme inhibitors.

In the design of clinically safe and effective metalloenzyme inhibitors, use of the most appropriate metal-binding group for the particular target and clinical indication is critical. If a weakly binding metal-binding group is utilized, potency may be suboptimal. On the other hand, if a very tightly binding metal-binding group is utilized, selectivity for the target enzyme versus related metalloenzymes may be suboptimal. The lack of optimal selectivity can be a cause for clinical toxicity due to unintended inhibition of these off-target metalloenzymes. One example of such clinical toxicity is the unintended inhibition of human drug metabolizing enzymes such as CYP2C9, CYP2C19 and CYP3A4 by the currently-available azole antifungal agents such as fluconazole and voriconazole. It is believed that this off-target inhibition is caused primarily by the indiscriminate binding of the currently utilized 1-(1,2,4-triazole) to iron in the active site of CYP2C9, CYP2C19 and CYP3A4. Another example of this is the joint pain that has been observed in many clinical trials of matrix metalloproteinase inhibitors. This toxicity is considered to be related to inhibition of off-target metalloenzymes due to indiscriminate binding of the hydroxamic acid group to zinc in the off-target active sites.

Therefore, the search for metal-binding groups that can achieve a better balance of potency and selectivity remains an important goal and would be significant in the realization of therapeutic agents and methods to address currently unmet needs in treating and preventing diseases, disorders and symptoms thereof.

BRIEF SUMMARY OF THE INVENTION

The invention is directed towards compounds (e.g., any of those delineated herein), methods of modulating activity of metalloenzymes, and methods of treating diseases, disorders or symptoms thereof. The methods can comprise the compounds herein.

It is understood that the embodiments of the invention discussed below with respect to the preferred variable selections can be taken alone or in combination with one or more embodiments, or preferred variable selections, of the invention, as if each combination were explicitly listed herein.

In one aspect, provided are compounds of Formula I:

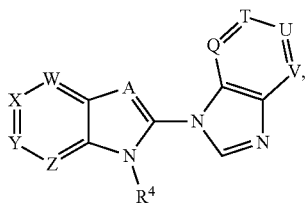

I or pharmaceutically acceptable salts, co-crystals, tautomers, stereoisomers, solvates, hydrates, polymorphs, isotopically enriched derivatives, or prodrugs thereof, wherein:

W, X, Y, and Z are each independently N or $CR^1$;
Q, T, U, and V are each independently N or $CR^2$;
A is N or $CR^3$;
provided that no more than two of W, X, Y, and Z are N; and no more than two of Q, T, U, and V are N;
each $R^1$ is independently hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, $(CR^eR^f)_nNR^aR^b$, $(CR^eR^f)_nNR^eS(O_2)R^d$, $(CR^eR^f)_nNR^eCO_2R^d$, $CO_2R^e$, $COR^f$, or $(CR^eR^f)_nOR^f$; wherein any $R^1$ can be optionally substituted with 1-3 independent substituents $R^7$;
each $R^2$ is independently hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, $(CR^eR^f)_nNR^aR^b$, $(CR^eR^f)_nNR^eS(O_2)R^d$, $(CR^eR^f)_nNR^eCO_2R^d$, $N(S(O_2)R^d)_2$, $CO_2R^e$, $COR^f$, or $(CR^eR^f)_nOR^f$; wherein any $R^2$ can be optionally substituted with 1-3 independent substituents $R^7$;
$R^3$ is hydrogen, cyano, alkyl, haloalkyl, heteroalkyl, or cycloalkyl;
$R^4$ is hydrogen, alkyl, cycloalkyl, haloalkyl, or heteroalkyl;

each n is independently 0, 1, 2, 3, 4, 5, 6, 7, 8, 9, or 10;
each occurrence of $R^7$ is, independently, halogen, alkyl, alkoxy, haloalkyl, carboxyl, aryl, aryl substituted with 1-3 independent halogen, $—(CR^eR^f)_nC(O)NR^aR^b$, $—S(O)_2R^d$, $—CO_2R^e$, or $NR^aR^b$; and
each occurrence of $R^a$, $R^b$, $R^c$, $R^d$, $R^e$, and $R^f$ are, independently, hydrogen, acyl, alkyl, alkenyl, alkynyl, heteroalkyl, haloalkyl, cycloalkyl, heterocycloalkyl, aryl, heteroaryl, alkoxyalkyl, $C(O)OC_{1-6}$ alkyl, $C(O)OH$, $C(O)C_{1-6}$ alkyl, $S(O_2)C_{1-6}$ alkyl, $S(O_2)aryl$, $S(O_2)heteroaryl$, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or $R^c$ and $R^d$ together with the atoms to which they are attached form a heterocycloalkyl ring.

In certain embodiments, no more than one of W, X, Y, and Z is N.

In certain embodiments, W, X, Y, and Z are each $CR^1$.
In certain embodiments, W and Y are each $CR^1$.
In certain embodiments, Z is N. In certain embodiments, Z is $CR^1$.
In certain embodiments, X is N. In certain embodiments, X is $CR^1$.
In certain embodiments, W, X, and Y are each $CR^1$; and Z is N.

In certain embodiments, no more than one of Q, T, U, and V is N.
In certain embodiments, at least one of Q, T, U, and V is N.
In certain embodiments, Q, T, U, and V are each $CR^2$.
In certain embodiments, Q and V are each $CR^2$.
In certain embodiments, T and U are each $CR^2$.
In certain embodiments, T is N; and U is $CR^2$. In certain embodiments, U is N; and T is $CR^2$.
In certain embodiments, one of T and U is N and the other is $CR^2$.
In certain embodiments, Q and V are each $CR^2$, one of T and U is N and the other is $CR^2$.
In certain embodiments, T is N.
In certain embodiments, U is N.
In certain embodiments, Q, U, and V are each $CR^2$; and T is N.
In certain embodiments, Q, T, and V are each $CR^2$; and U is N.
In certain embodiments, W, X, Y, and Z are each $CR^1$; Q and V are each $CR^2$; and one of T and U is N and the other is $CR^2$. In certain embodiments, W, X, Y, and Z are each $CR^1$; Q, U, and V are each $CR^2$; and T is N. In certain embodiments, W, X, Y, and Z are each $CR^1$; Q, T, and V are each $CR^2$; and U is N.

In certain embodiments, W, X, and Y are each $CR^1$; Z is N; Q and V are each $CR^2$; and one of T and U is N and the other is $CR^2$. In certain embodiments, W, X, and Y are each $CR^1$; Z is N; Q, U, and V are each $CR^2$; and T is N. In certain embodiments, W, X, and Y are each $CR^1$; Z is N; Q, T, and V are each $CR^2$; and U is N.

In certain embodiments, W, X, Y, and Z are each $CR^1$; and Q, T, U, and V are each $CR^2$.

In certain embodiments, A is $CR^3$ and $R^3$ is hydrogen, $C_{1-4}$ alkyl, or $C_{3-5}$ cycloalkyl.

In certain embodiments, A is N.

In certain embodiments, each $R^1$ is independently hydrogen, halogen, cyano, alkyl, alkoxy, haloalkyl, or haloalkoxy.

In certain embodiments, each $R^1$ is independently hydrogen, halogen, or cyano.

In certain embodiments, each $R^1$ is independently hydrogen, fluoro, chloro, or cyano.

In certain embodiments, each $R^1$ is independently hydrogen or cyano. In certain embodiments, each $R^1$ is independently hydrogen or halogen. In certain embodiments, each $R^1$ is independently hydrogen or chloro. In certain embodiments, each $R^1$ is independently hydrogen or fluoro.

In certain embodiments, at least one $R^1$ is halogen or cyano. In certain embodiments, at least one $R^1$ is fluoro, chloro, or cyano. In certain embodiments, at least one $R^1$ is chloro or cyano. In certain embodiments, at least one $R^1$ is fluoro or cyano. In certain embodiments, at least one $R^1$ is halogen. In certain embodiments, at least one $R^1$ is fluoro or chloro. In certain embodiments, at least one $R^1$ is fluoro. In certain embodiments, at least one $R^1$ is chloro. In certain embodiments, at least one $R^1$ is cyano.

In certain embodiments, each $R^2$ is independently hydrogen, halogen, cyano, acyl, alkyl, alkenyl, alkynyl, haloalkyl, alkoxy, haloalkoxy, cycloalkyl, cycloalkoxy, $(CR^eR^f)_nNR^aR^b$, $(CR^eR^f)_nNR^eS(O_2)R^d$, $(CR^eR^f)_nNR^eCO_2R^d$, $CO_2R^e$, $COR^f$, or $(CR^eR^f)_nOR^f$.

In certain embodiments, each $R^2$ is independently hydrogen, halogen, cyano, alkyl, haloalkyl, alkoxy, haloalkoxy, $(CR^eR^f)_nNR^eS(O_2)R^d$, or $CO_2R^e$.

In certain embodiments, each $R^2$ is independently hydrogen, halogen, cyano, alkyl, haloalkyl, alkoxy, haloalkoxy, or $(CR^eR^f)_nNR^eS(O_2)R^d$.

In certain embodiments, each $R^2$ is independently hydrogen, haloalkyl, or $NHS(O_2)R^d$; and $R^d$ is alkyl.

In certain embodiments, each $R^2$ is independently hydrogen, halogen, $C_{1-3}$ alkoxy, cyano, $C_{1-3}$ alkyl, $N(S(O_2)C_{1-3}$ alkyl$)_2$, $NHS(O_2)C_{1-3}$ alkyl, $CO_2H$, $C_{1-3}$ haloalkyl, or $C_{1-3}$ haloalkoxy. In certain embodiments, each $R^2$ is independently hydrogen, halogen, $C_{1-3}$ alkoxy, cyano, $C_{1-3}$ alkyl, $NHS(O_2)C_{1-3}$ alkyl, $C_{1-3}$ haloalkyl, or $C_{1-3}$ haloalkoxy. In certain embodiments, each $R^2$ is independently hydrogen, $NHS(O_2)C_{1-3}$ alkyl, or $C_{1-3}$ haloalkyl.

In certain embodiments, each $R^2$ is independently hydrogen, fluoro, $C_{1-3}$ alkoxy, cyano, $C_{1-3}$ alkyl, $NHS(O_2)Me$, $N(S(O_2)Me)_2$, $CO_2H$, $C_{1-3}$ haloalkyl, or $C_{1-3}$ haloalkoxy. In certain embodiments, each $R^2$ is independently hydrogen, fluoro, $C_{1-3}$ alkoxy, cyano, $C_{1-3}$ alkyl, $NHS(O_2)Me$, $C_{1-3}$ haloalkyl, or $C_{1-3}$ haloalkoxy. In certain embodiments, each $R^2$ is independently hydrogen, $NHS(O_2)Me$, or $C_{1-3}$ haloalkyl.

In certain embodiments, each $R^2$ is independently hydrogen, fluoro, methoxy, cyano, methyl, ethyl, $NHS(O_2)Me$, $N(S(O_2)Me)_2$, $CO_2H$, difluoromethyl, trifluoromethyl, trifluoromethoxy, or difluoromethoxy. In certain embodiments, each $R^2$ is independently hydrogen, fluoro, methoxy, cyano, methyl, ethyl, $NHS(O_2)Me$, $CO_2H$, difluoromethyl, trifluoromethyl, trifluoromethoxy, or difluoromethoxy. In certain embodiments, each $R^2$ is independently hydrogen, $NHS(O_2)Me$, or difluoromethyl.

In certain embodiments, at least one $R^2$ is hydrogen, halogen, cyano, alkyl, haloalkyl, alkoxy, haloalkoxy, or $(CR^eR^f)_nNR^eS(O_2)R^d$. In certain embodiments, at least one $R^2$ is halogen, cyano, alkyl, haloalkyl, alkoxy, haloalkoxy, or $(CR^eR^f)_nNR^eS(O_2)R^d$. In certain embodiments, at least one $R^2$ is hydrogen, halogen, cyano, $C_{1-3}$ alkyl, $C_{1-3}$ haloalkyl, $C_{1-3}$ alkoxy, $C_{1-3}$ haloalkoxy, or $NHS(O_2)C_{1-3}$ alkyl. In certain embodiments, at least one $R^2$ is halogen, cyano, $C_{1-3}$ alkyl, $C_{1-3}$ haloalkyl, $C_{1-3}$ alkoxy, $C_{1-3}$ haloalkoxy, or $NHS(O_2)C_{1-3}$ alkyl. In certain embodiments, at least one $R^2$ is hydrogen, fluoro, cyano, methyl, ethyl, methoxy, difluoromethyl, trifluoromethyl, trifluoromethoxy, difluoromethoxy, or $NHS(O_2)Me$. In certain embodiments, at least one $R^2$ is fluoro, cyano, methyl, ethyl, methoxy, difluoromethyl, trifluoromethyl, trifluoromethoxy, difluoromethoxy, or $NHS(O_2)Me$. In certain embodiments, at least one $R^2$ is hydrogen, fluoro, cyano, ethyl, methoxy, trifluoromethyl, difluoromethoxy, or $NHS(O_2)Me$. In certain embodiments, at least one $R^2$ is fluoro, cyano, ethyl, methoxy, trifluoromethyl, difluoromethoxy, or $NHS(O_2)Me$. In certain embodiments, at least one $R^2$ is hydrogen, difluoromethoxy, or $NHS(O_2)Me$. In certain embodiments, at least one $R^2$ is difluoromethoxy or $NHS(O_2)Me$.

In certain embodiments, $R^3$ is hydrogen, cyano, alkyl, haloalkyl, heteroalkyl, or cycloalkyl. In certain embodiments, $R^3$ is hydrogen, alkyl, haloalkyl, heteroalkyl, or cycloalkyl. In certain embodiments, $R^3$ is alkyl, haloalkyl, heteroalkyl, or cycloalkyl. In certain embodiments, $R^3$ is alkyl, haloalkyl, or cycloalkyl. In certain embodiments, $R^3$ is alkyl or cycloalkyl. In certain embodiments, $R^3$ is alkyl. In certain embodiments, $R^3$ is alkyl or cycloalkyl. In certain embodiments, $R^3$ is $C_{1-3}$ alkyl or $C_{3-5}$ cycloalkyl.

In certain embodiments, $R^4$ is alkyl or cycloalkyl. In certain embodiments, $R^4$ is $C_{1-4}$ alkyl or $C_{3-5}$ cycloalkyl. In certain embodiments, $R^4$ is ethyl or cyclopropyl. In certain embodiments, $R^4$ is $C_{1-4}$ alkyl. In certain embodiments, $R^4$ is $C_{3-5}$ cycloalkyl.

In certain embodiments, $R^4$ is cyclopentyl. In certain embodiments, $R^4$ is cyclobutyl. In certain embodiments, $R^4$ is cyclopropyl.

In certain embodiments, $R^4$ is $C_{1-4}$ alkyl. In certain embodiments, $R^4$ is methyl. In certain embodiments, $R^4$ is ethyl. In certain embodiments, $R^4$ is n-propyl. In certain embodiments, $R^4$ is i-propyl. In certain embodiments, $R^4$ is n-butyl. In certain embodiments, $R^4$ is i-butyl. In certain embodiments, $R^4$ is t-butyl.

In certain embodiments, each $R^1$ is independently hydrogen, halogen, or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, each $R^1$ is independently hydrogen or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, each $R^1$ is independently hydrogen or halogen; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, each $R^1$ is independently halogen; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, each $R^1$ is independently hydrogen, chloro, fluoro, or cyano; each $R^2$ is independently hydrogen, chloro, fluoro, cyano, methyl, trifluoromethyl, difluromethylmethoxy, trifluoromethoxy, difluoromethoxy, or $NHS(O_2)CH_3$; and $R^4$ is cyclopropyl.

In certain embodiments, each $R^1$ is independently hydrogen or cyano; each $R^2$ is independently hydrogen, chloro, fluoro, cyano, methyl, trifluoromethyl, difluoromethylmethoxy, trifluoromethoxy, difluoromethoxy, or $NHS(O_2)CH_3$; and $R^4$ is cyclopropyl.

In certain embodiments, each $R^1$ is independently hydrogen, chloro, or fluoro; each $R^2$ is independently hydrogen, chloro, fluoro, cyano, methyl, trifluoromethyl, difluromethylmethoxy, trifluoromethoxy, difluoromethoxy, or $NHS(O_2)CH_3$; and $R^4$ is cyclopropyl.

In certain embodiments, the compound of Formula I is a compound of Formula I-a:

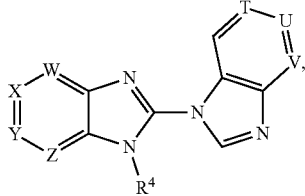

I-a or a pharmaceutically acceptable salt, co-crystal, tautomer, stereoisomer, solvate, hydrate, polymorph, isotopically enriched derivative, or prodrug thereof, wherein $R^4$, W, X, Y, Z, T, U, and V are as defined herein.

In certain embodiments, the compound of Formula I is a compound of Formula I-b:

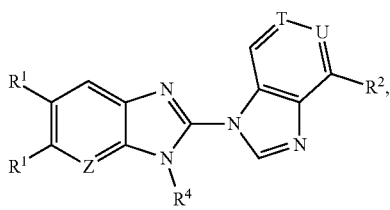

I-b or a pharmaceutically acceptable salt, co-crystal, tautomer, stereoisomer, solvate, hydrate, polymorph, isotopically enriched derivative, or prodrug thereof, wherein $R^1$, $R^2$, $R^4$, Z, T, and U are as defined herein.

In certain embodiments, the compound of Formula I is a compound of Formula I-c:

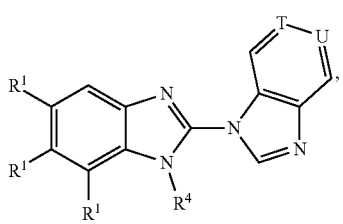

I-c or a pharmaceutically acceptable salt, co-crystal, tautomer, stereoisomer, solvate, hydrate, polymorph, isotopically enriched derivative, or prodrug thereof, wherein $R^1$, $R^4$, T, and U are as defined herein.

In certain embodiments, the compound of Formula I is a compound of Formula I-d:

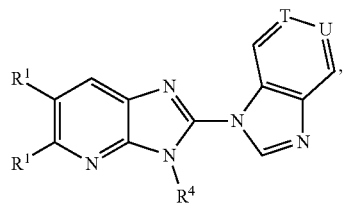

I-d or a pharmaceutically acceptable salt, co-crystal, tautomer, stereoisomer, solvate, hydrate, polymorph, isotopically enriched derivative, or prodrug thereof, wherein $R^1$, $R^4$, T, and U are as defined herein.

In certain embodiments, the compound of Formula I is a compound of Formula I-e:

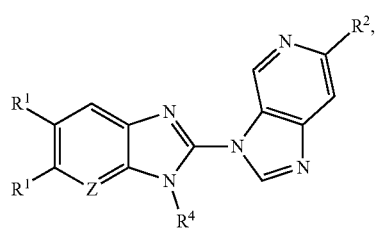

I-e or a pharmaceutically acceptable salt, co-crystal, tautomer, stereoisomer, solvate, hydrate, polymorph, isotopically enriched derivative, or prodrug thereof, wherein $R^1$, $R^2$, $R^4$, and Z are as defined herein.

In certain embodiments of the compounds of formula I-e, Z is $CR^1$ or N; each $R^1$ is independently hydrogen, halogen, or cyano; $R^2$ is hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments of the compounds of formula I-e, Z is $CR^1$; each $R^1$ is independently hydrogen, halogen, or cyano; $R^2$ is hydrogen or haloalkyl; and $R^4$ is cyclopropyl.

In certain embodiments of the compounds of formula I-e, Z is N; each $R^1$ is independently hydrogen, halogen, or cyano; $R^2$ is hydrogen or haloalkyl; and $R^4$ is cyclopropyl.

In certain embodiments, the compound of Formula I is a compound of Formula I-f:

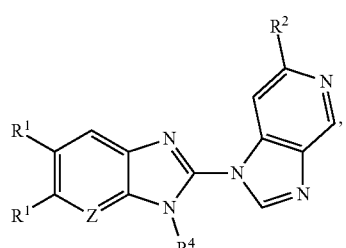

I-f or a pharmaceutically acceptable salt, co-crystal, tautomer, stereoisomer, solvate, hydrate, polymorph, isotopically enriched derivative, or prodrug thereof, wherein $R^1$, $R^2$, $R^4$, and Z are as defined herein.

In certain embodiments of the compounds of formula I-f, Z is $CR^1$ or N; each $R^1$ is independently hydrogen, halogen, or cyano; $R^2$ is hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments of the compounds of formula I-f, Z is $CR^1$; each $R^1$ is independently hydrogen, halogen, or cyano; $R^2$ is hydrogen, or haloalkyl; and $R^4$ is cyclopropyl.

In certain embodiments of the compounds of formula I-f, Z is N; each $R^1$ is independently hydrogen, halogen, or cyano; $R^2$ is hydrogen or haloalkyl; and $R^4$ is cyclopropyl.

In certain embodiments, the compound of Formula I is a compound of Formula I-g:

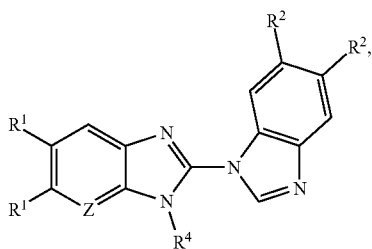

I-g or a pharmaceutically acceptable salt, co-crystal, tautomer, stereoisomer, solvate, hydrate, polymorph, isotopically enriched derivative, or prodrug thereof, wherein $R^1$, $R^2$, $R^4$, and Z are as defined herein.

In certain embodiments of the compounds of formula I-g, Z is $CR^1$ or N; each $R^1$ is independently hydrogen, halogen, or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments of the compounds of formula I-g, Z is $CR^1$; each $R^1$ is independently hydrogen, halogen, or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, the compound of Formula I is a compound of Formula I-h:

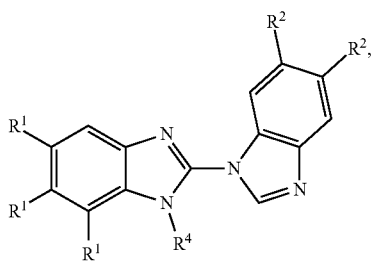

I-h or a pharmaceutically acceptable salt, co-crystal, tautomer, stereoisomer, solvate, hydrate, polymorph, isotopically enriched derivative, or prodrug thereof, wherein $R^1$, $R^2$, and $R^4$ are as defined herein.

In certain embodiments of the compounds of formula I-h, each $R^1$ is independently hydrogen, halogen, or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, the compound of Formula I is a compound of Formula I-i:

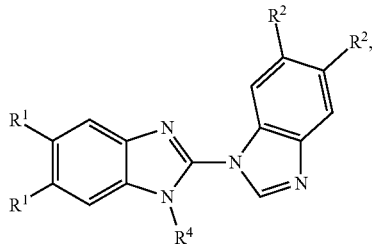

I-i or a pharmaceutically acceptable salt, co-crystal, tautomer, stereoisomer, solvate, hydrate, polymorph, isotopically enriched derivative, or prodrug thereof, wherein $R^1$, $R^2$, and $R^4$ are as defined herein.

In certain embodiments of the compounds of formula I-i, each $R^1$ is independently hydrogen, halogen, or cyano; each $R^2$ is independently hydrogen, halogen, cyano, alkyl, haloalkyl, alkoxy, haloalkoxy, or $(CR^eR^f)_nNR^eS(O_2)R^d$; and $R^4$ is cyclopropyl.

In certain embodiments, the compound of Formula I is a compound of Formula I-j:

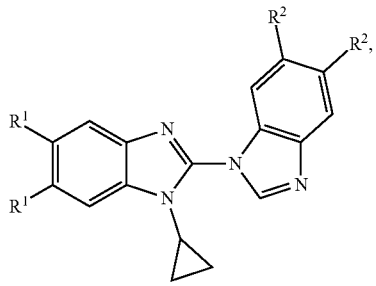

I-j or a pharmaceutically acceptable salt, co-crystal, tautomer, stereoisomer, solvate, hydrate, polymorph, isotopically enriched derivative, or prodrug thereof, wherein $R^1$ and $R^2$ are as defined herein.

In certain embodiments of the compounds of formula I-j, each $R^1$ is independently hydrogen, halogen, or cyano; and each $R^2$ is independently hydrogen, halogen, cyano, alkyl, haloalkyl, alkoxy, haloalkoxy, or $(CR^eR^f)_nNR^eS(O_2)R^d$.

In certain embodiments, the compound of Formula I is a compound selected from the group consisting of:

1'-Cyclopropyl-6'-fluoro-1'H-1,2'-bibenzo[d]imidazole (1);

1'-Cyclopropyl-6',7'-difluoro-1'H-1,2'-bibenzo[d]imidazole (2);

1'-Cyclopropyl-4,5,6'-trifluoro-1'H-1,2'-bibenzo[d]imidazole (3);

1'-Cyclopropyl-5,6,6'-trifluoro-1'H-1,2'-bibenzo[d]imidazole (4);

1'-Cyclopropyl-6'-fluoro-5,6-dimethoxy-1'H-1,2'-bibenzo[d]imidazole (5);

1'-Cyclopropyl-6'-fluoro-1'H-[1,2'-bibenzo[d]imidazole]-5-carbonitrile (6);

1'-Cyclopropyl-6'-fluoro-1'H-[1,2'-bibenzo[d]imidazole]-6-carbonitrile (7);

1'-Cyclopropyl-6'-fluoro-5-methyl-1'H-1,2'-bibenzo[d]imidazole (8);

1'-Cyclopropyl-6'-fluoro-6-methyl-1'H-1,2'-bibenzo[d]imidazole (9);

1'-Cyclopropyl-5-ethyl-6'-fluoro-1'H-1,2'-bibenzo[d]imidazole (10);
1'-Cyclopropyl-6-ethyl-6'-fluoro-1'H-1,2'-bibenzo[d]imidazole (11);
1'-Cyclopropyl-6'-fluoro-5-methoxy-1'H-1,2'-bibenzo[d]imidazole (12);
1'-Cyclopropyl-6'-fluoro-6-methoxy-1'H-1,2'-bibenzo[d]imidazole (13);
1'-Cyclopropyl-6'-fluoro-4-methyl-1'H-1,2'-bibenzo[d]imidazole (14);
1'-Cyclopropyl-5,6,6',7'-tetrafluoro-1'H-1,2'-bibenzo[d]imidazole (15);
1'-Cyclopropyl-5',6'-difluoro-1'H-1,2'-bibenzo[d]imidazole (16);
1'-Cyclopropyl-5,5',6,6'-tetrafluoro-1'H-1,2'-bibenzo[d]imidazole (17);
1'-Cyclopropyl-5,6-difluoro-1'H-1,2'-bibenzo[d]imidazole (18);
1'-Cyclopropyl-6,6'-difluoro-1'H-1,2'-bibenzo[d]imidazole (19);
1'-Cyclopropyl-6'-fluoro-5-(trifluoromethyl)-1'H-1,2'-bibenzo[d]imidazole (20);
1'-Cyclopropyl-6'-fluoro-6-(trifluoromethyl)-1'H-1,2'-bibenzo[d]imidazole (21);
1'-ethyl-5,6-difluoro-1'H-[1,2'-bibenzo[d]imidazole]-6'-carbonitrile (22);
1'-Cyclopropyl-5',6'-difluoro-1'H-[1,2'-bibenzo[d]imidazole]-5-carbonitrile (23);
1'-Cyclopropyl-5',6'-difluoro-1'H-[1,2'-bibenzo[d]imidazole]-6-carbonitrile (24);
1'-Cyclopropyl-5,6-difluoro-1'H-[1,2'-bibenzo[d]imidazole]-6'-carbonitrile (25);
6'-Chloro-1'-cyclopropyl-5,6-difluoro-1'H-1,2'-bibenzo[d]imidazole (26);
1'-Cyclopropyl-6'-fluoro-5-(trifluoromethoxy)-1'H-1,2'-bibenzo[d]imidazole (27);
1'-Cyclopropyl-6'-fluoro-6-(trifluoromethoxy)-1'H-1,2'-bibenzo[d]imidazole (28);
5-Chloro-3-cyclopropyl-2-(5,6-difluoro-1H-benzo[d]imidazol-1-yl)-3H-imidazo[4,5-b]pyridine (29);
N-(1'-cyclopropyl-6',7'-difluoro-1'H-[1,2'-bibenzo[d]imidazol]-5-yl)-N-(methylsulfonyl) methanesulfonamide (30);
N-(1'-cyclopropyl-6',7'-difluoro-1'H-[1,2'-bibenzo[d]imidazol]-5-yl)methanesulfonamide (31);
3-Cyclopropyl-2-(5,6-difluoro-1H-benzo[d]imidazol-1-yl)-3H-imidaz[4,5-b]pyridine-5-carbonitrile (32);
N-(1'-cyclopropyl-6',7'-difluoro-1'H-[1,2'-bibenzo[d]imidazol]-6-yl)methanesulfonamide (33);
1-(1-Cyclopropyl-5,6-difluoro-1H-benzo[d]imidazol-2-yl)-1H-imidazo[4,5-b]pyridine (34);
1-(1-Cyclopropyl-5,6-difluoro-1H-benzo[d]imidazol-2-yl)-1H-imidazo[4,5-c]pyridine (35);
3-(1-Cyclopropyl-5,6-difluoro-1H-benzo[d]imidazol-2-yl)-3H-imidazo[4,5-c]pyridine (36);
3-cyclopropyl-2-(3H-imidazo[4,5-c]pyridin-3-yl)-3H-imidazo[4,5-b]pyridine-5-carbonitrile (37);
3-cyclopropyl-2-(1H-imidazo[4,5-c]pyridin-1-yl)-3H-imidazo[4,5-b]pyridine-5-carbonitrile (38);
1-(1-Cyclopropyl-5,6-difluoro-1H-benzo[d]imidazol-2-yl)-1H-imidazo[4,5-c]pyridine-6-carboxylic acid (39);
1-(1-Cyclopropyl-5,6-difluoro-1H-benzo[d]imidazol-2-yl)-6-(difluoromethyl)-1H-imidazo[4,5-c]pyridine (40);
3-(1-Cyclopropyl-5,6-difluoro-1H-benzo[d]imidazol-2-yl)-6-(difluoromethyl)-3H-imidazo[4,5-c]pyridine (41);
1-Cyclopropyl-2-(3H-imidazo[4,5-c]pyridin-3-yl)-1H-benzo[d]imidazole-6-carbonitrile (42);
1-Cyclopropyl-2-(1H-imidazo[4,5-c]pyridin-1-yl)-1H-benzo[d]imidazole-6-carbonitrile (43);
1'-Cyclopropyl-5',6'-difluoro-1'H-[1,2'-bibenzo[d]imidazole]-5-carboxylic acid (Ex. 44);
N-(1'-Cyclopropyl-5',6'-difluoro-1'H-[1,2'-bibenzo[d]imidazol]-6-yl)methanesulfonamide (45);
N-(1'-Cyclopropyl-5',6'-difluoro-1'H-[1,2'-bibenzo[d]imidazol]-5-yl) methanesulfonamide (46);
N-(6'-Cyano-1'-cyclopropyl-1'H-[1,2'-bibenzo[d]imidazol]-5-yl)methanesulfonamide (47);
N-(6'-Cyano-1'-cyclopropyl-1'H-[1,2'-bibenzo[d]imidazol]-6-yl)methanesulfonamide (48);
1'-Cyclopropyl-5-(difluoromethoxy)-1'H-[1,2'-bibenzo[d]imidazole]-6'-carbonitrile (49);
1'-Cyclopropyl-6-(difluoromethoxy)-1'H-[1,2'-bibenzo[d]imidazole]-6'-carbonitrile (50);
1'-Cyclopropyl-5',6'-difluoro-1'H-[1,2'-bibenzo[d]imidazole]-6-carboxylic acid (51);
1'-Cyclopropyl-5-(difluoromethoxy)-5',6'-difluoro-1'H-1,2'-bibenzo[d]imidazole (52);
1'-Cyclopropyl-6-(difluoromethoxy)-5',6'-difluoro-1'H-1,2'-bibenzo[d]imidazole (53); and pharmaceutically acceptable salts, co-crystals, tautomers, stereoisomers, solvates, hydrates, polymorphs, isotopically enriched derivatives, and prodrugs thereof.

In one aspect, the compound of Formula I is that wherein the compound inhibits (or is identified to inhibit) aldosterone synthase (CYP11B2).

The compounds herein include those wherein the compound is identified as attaining affinity, at least in part, for a metalloenzyme by formation of one or more of the following types of chemical interactions or bonds to a metal: sigma bonds, covalent bonds, coordinate-covalent bonds, ionic bonds, pi bonds, delta bonds, or backbonding interactions. The compounds can also attain affinity through weaker interactions with the metal such as van der Waals interactions, pi cation interactions, pi-anion interactions, dipole-dipole interactions, ion-dipole interactions. In one aspect, the compound is identified as having a bonding interaction with the metal via the pyrimidine moiety.

Methods for assessing metal-ligand binding interactions are known in the art as exemplified in references including, for example, "Principles of Bioinorganic Chemistry" by Lippard and Berg, University Science Books, (1994); "Mechanisms of Inorganic Reactions" by Basolo and Pearson John Wiley & Sons Inc; 2nd edition (September 1967); "Biological Inorganic Chemistry" by Ivano Bertini, Harry Gray, Ed Stiefel, Joan Valentine, University Science Books (2007); Xue et al. "Nature Chemical Biology", vol. 4, no. 2, 107-109 (2008).

In another aspect, provided are pharmaceutical compositions comprising the compound of Formula I and a pharmaceutically acceptable carrier.

In another aspect, provided are methods of modulating metalloenzyme activity in a subject, comprising contacting the subject with a compound of Formula I, in an amount and under conditions sufficient to modulate metalloenzyme activity.

In another aspect, provided are methods of treating a subject suffering from or susceptible to a disorder or disease, wherein the subject has been identified as in need of treatment for the disorder or disease, comprising administering to said subject in need thereof, an effective amount of a compound or pharmaceutical composition of Formula I, such that said subject is treated for said disorder.

In another aspect the subject is an animal other than a human.

In another aspect, provided are methods of treating a subject suffering from or susceptible to a metalloenzyme-related disorder or disease, comprising administering to the subject an effective amount of a compound or pharmaceutical composition of Formula I.

In another aspect, provided are methods of treating a subject suffering from or susceptible to a metalloenzyme-related disorder or disease, wherein the subject has been identified as in need of treatment for a metalloenzyme-related disorder or disease, comprising administering to said subject in need thereof, an effective amount of a compound or pharmaceutical composition of Formula I, such that said subject is treated for said disorder.

In another aspect, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of Formula I, such that metalloenzyme activity in said subject is modulated (e.g., down regulated, inhibited).

The methods herein include those wherein the disease or disorder is mediated by any of aromatase (CYP19), a member of the cyclooxygenase family, lanosterol demethylase (CYP51), a member of the nitric oxide synthase family, thromboxane synthase (CYP5a), thyroid peroxidase, 17-alpha hydroxylase/17,20-lyase (CYP17), cytochrome P450 2A6 (CYP2A6), heme oxygenase, indoleamine 2,3-dioxygenase, retinoic acid hydroxylase (CYP26), vitamin D hydroxylase (CYP24), sterol 27-hydroxylase (CYP27), cytochrome P450 3A5 (CYP3A5), cholesterol 24-hydroxylase (CYP46), cytochrome P450 4F2 (CYP4F2), myeloperoxidase, or 11-beta-hydroxylase (CYP11B1).

The methods herein include those wherein the disease or disorder is cancer, cardiovascular disease, inflammatory disease, infectious disease, metabolic disease, ophthalmologic disease, central nervous system (CNS) disease, urologic disease, or gastrointestinal disease.

The methods herein include those wherein the disease or disorder is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

DETAILED DESCRIPTION

Definitions

In order that the invention may be more readily understood, certain terms are first defined here for convenience.

As used herein, the term "treating" a disorder encompasses preventing, ameliorating, mitigating and/or managing the disorder and/or conditions that may cause the disorder. The terms "treating" and "treatment" refer to a method of alleviating or abating a disease and/or its attendant symptoms. In accordance with the present disclosure "treating" includes preventing, blocking, inhibiting, attenuating, protecting against, modulating, reversing the effects of and reducing the occurrence of e.g., the harmful effects of a disorder.

As used herein, "inhibiting" encompasses preventing, reducing and halting progression. Note that "enzyme inhibition" (e.g., metalloenzyme inhibition) is distinguished and described below.

The term "modulate" refers to increases or decreases in the activity of an enzyme in response to exposure to a compound of the present disclosure.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 µg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 µM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 µg/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branched or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the present disclosure are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Use of the word "inhibitor" herein is meant to mean a molecule that exhibits activity for inhibiting a metalloenzyme. By "inhibit" herein is meant to decrease the activity of metalloenzyme, as compared to the activity of metalloenzyme in the absence of the inhibitor. In some embodiments, the term "inhibit" means a decrease in metalloenzyme activity of at least about 5%, at least about 10%, at least about 20%, at least about 25%, at least about 50%, at least about 60%, at least about 70%, at least about 80%, at least about 90%, or at least about 95%. In other embodiments, inhibit means a decrease in metalloenzyme activity of about 5% to about 25%, about 25% to about 50%, about 50% to about 75%, or about 75% to 100%. In some embodiments, inhibit means a decrease in metalloenzyme activity of about 95% to 100%, e.g., a decrease in activity of 95%, 96%, 97%, 98%, 99%, or 100%. Such decreases can be measured using a variety of techniques that would be recognizable by one of skill in the art. Particular assays for measuring individual activity are described below.

Furthermore, the compounds of the present disclosure include olefins having either geometry: "Z" refers to what is referred to as a "cis" (same side) configuration whereas "E" refers to what is referred to as a "trans" (opposite side) configuration. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a $C_1$-$C_6$ alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "arylalkenyl" refers to an unsaturated hydrocarbon chain that may be a straight chain or branched chain, containing 2 to 12 carbon atoms and at least one carbon-carbon double bond wherein one or more of the sp$^2$ hybridized carbons of the alkenyl unit attaches to an aryl moiety. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The sp$^2$ or sp carbons of an alkenyl group and an alkynyl group, respectively, may optionally be the point of attachment of the alkenyl or alkynyl groups.

The term "alkoxy" refers to an —O-alkyl substituent.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation.

Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —S(O)$_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroarylalkyl" refers to an -alkyl-heteroaryl substituent.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent.

The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiirenyl, and the like.

The term "heterocycloalkylalkyl" refers to an -alkyl-heterocycloalkyl substituent.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)CF$_3$), sulfonates (e.g., mesyl, tosyl), acetamides (e.g., —NHC(O)Me), carbamates (e.g., N(Me)C(O)Ot-Bu), phosphonates (e.g., —OP(O)(OEt)$_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carboxamido, carbamido, carbamyl, thioureido, thiocyanato, sulfoamido, sulfonylalkyl, sulfonylaryl, mercaptoalkoxy, N-hydroxyamidinyl, or N'-aryl, N"-hydroxyamidinyl.

Compounds of the present disclosure can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis, 2$^{nd}$ Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present disclosure.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present disclosure. The compounds herein may also be represented in multiple tautomeric forms, in such instances, the present disclosure expressly includes all tautomeric forms of the compounds described herein, even though only a single tautomeric form may be represented. All such isomeric forms of such compounds herein are expressly included in the present disclosure. All crystal forms and polymorphs of the compounds described herein are expressly included in the present disclosure. Also embodied are extracts and fractions comprising compounds of the present disclosure. The term isomers is intended to include diastereoisomers, enantiomers, regioisomers, structural isomers, rotational isomers, tautomers, and the like. For compounds which contain one or more stereogenic centers, e.g., chiral compounds, the methods of the present disclosure may be carried out with an enantiomerically enriched compound, a racemate, or a mixture of diastereomers.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the present disclosure is administered to cells or a subject.

Methods of Treatment

In one aspect, provided are methods of treating a subject suffering from or susceptible to a disorder or disease, comprising administering to the subject an effective amount of a compound or pharmaceutical composition of Formula I.

In other aspects, provided are methods of treating a subject suffering from or susceptible to a disorder or disease, wherein the subject has been identified as in need of treatment for a metalloenzyme-mediated disorder or disease, comprising administering to said subject in need thereof, an effective amount of a compound or pharmaceutical composition of Formula I, such that said subject is treated for said disorder.

In one aspect, provided are methods of modulating the metalloenzyme activity of a cell in a subject, comprising contacting the subject with a compound of Formula I, in an amount and under conditions sufficient to modulate metalloenzyme activity.

In one embodiment, the modulation is inhibition.

In another aspect, provided are methods of treating a subject suffering from or susceptible to a metalloenzyme-mediated disorder or disease, comprising administering to the subject an effective amount of a compound or pharmaceutical composition of Formula I.

In other aspects, provided are methods of treating a subject suffering from or susceptible to a metalloenzyme-mediated disorder or disease, wherein the subject has been identified as in need of treatment for a metalloenzyme-mediated disorder or disease, comprising administering to said subject in need thereof, an effective amount of a compound or pharmaceutical composition of Formula I, such that said subject is treated for said disorder.

In certain embodiments, provided are methods of treating a disease, disorder or symptom thereof, wherein the disorder is cancer, cardiovascular disease, endocrinologic disease, inflammatory disease, infectious disease, gynecologic disease, metabolic disease, ophthalmologic disease, central nervous system (CNS) disease, urologic disease, or gastrointestinal disease. In certain embodiments the disease is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

In certain embodiments, the subject is a mammal, preferably a primate or human.

In another embodiment, provided are methods as described above, wherein the effective amount of the compound of Formula I is as described above.

In another embodiment, provided are methods as described above, wherein the compound of Formula I is administered intravenously, intramuscularly, subcutaneously, intracerebroventricularly, orally or topically.

In another embodiment, provided are methods as described herein wherein the compound of Formula I demonstrates selectivity for an activity range against a target enzyme (e.g., aldosterone synthase (CYP11B2) $IC_{50} < 1.0$ µM).

In other embodiments, provided are methods as described above, wherein the compound of Formula I is administered alone or in combination with one or more other therapeutics. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In certain embodiments, the additional therapeutic agent is an agent for the treatment of hypertension, agent for the treatment of primary aldosteronism, agent for the treatment of kidney disease, agent for the treatment of congestive heart failure, agent for the treatment of atherosclerotic conditions, agent for the treatment of diabetes, agent for the treatment of obesity, or agent for the treatment of metabolic disease.

Exemplary additional therapeutic agents include, but are not limited to, renin inhibitors, angiotensin converting enzyme (ACE) inhibitors, dual inhibitors of angiotensin converting enzyme (ACE) and neutral endopeptidase (NEP), angiotensin II receptor blockers (ARB), mineralocorticoid receptor antagonists (MRA), neutral endopeptidase inhibitors (NEP), neprilysin inhibitors, calcium channel blockers, alpha-adrenergic blockers, beta-adrenergic blockers, diuretics (including loop diuretics), potassium channel activators, endothelin receptor antagonists, endothelin 1 receptor agonists, soluble guanylate cyclase stimulators, vasodilators, HMG-CoA reductase inhibitors, niacin and niacin receptor agonists, Niemann-Pick Cl-like 1 (NPC1L1) inhibitors, insulin or insulin analogs, biguanides (e.g., metformin), sulfonylureas, peroxisome proliferator-activated receptor (PPAR) agonists and partial agonists including PPARγ agonists and other PPAR ligands, dipeptidyl peptidase-4 (DPP4) inhibitors, glucagon-like peptide 1 (GLP-1), GLP-1 receptor agonists, and sodium-glucose co-transporter 2 (SGLT2) inhibitors.

Another object of the present disclosure is the use of a compound as described herein (e.g., a compound of Formula I) in the manufacture of a medicament for use in the treatment of a metalloenzyme-mediated disorder or disease. Another object of the present disclosure is the use of a compound as described herein (e.g., a compound of Formula I) for use in the treatment of a metalloenzyme-mediated disorder or disease. Another object of the present disclosure is the use of a compound as described herein (e.g., a compound of Formula I) in the manufacture of an agricultural composition for use in the treatment or prevention of a metalloenzyme-mediated disorder or disease in agricultural or agrarian settings.

Pharmaceutical Compositions

In one aspect, provided are pharmaceutical compositions comprising the compound of Formula I and a pharmaceutically acceptable carrier.

In another embodiment, provided are pharmaceutical compositions further comprising an additional therapeutic agent. In a further embodiment, the additional therapeutic agent is an anti-cancer agent, antifungal agent, cardiovascular agent, anti-inflammatory agent, chemotherapeutic agent, an anti-angiogenesis agent, cytotoxic agent, an anti-proliferation agent, metabolic disease agent, ophthalmologic disease agent, central nervous system (CNS) disease agent, urologic disease agent, or gastrointestinal disease agent.

In certain embodiments, the additional therapeutic agent is an agent for the treatment of hypertension, agent for the treatment of primary aldosteronism, agent for the treatment of kidney disease, agent for the treatment of congestive heart failure, agent for the treatment of atherosclerotic conditions, agent for the treatment of diabetes, agent for the treatment of obesity, or agent for the treatment of metabolic disease.

Exemplary additional therapeutic agents include, but are not limited to, renin inhibitors, angiotensin converting enzyme (ACE) inhibitors, dual inhibitors of angiotensin converting enzyme (ACE) and neutral endopeptidase (NEP), angiotensin II receptor blockers (ARB), mineralocorticoid receptor antagonists (MRA), neutral endopeptidase inhibitors (NEP), neprilysin inhibitors, calcium channel blockers, alpha-adrenergic blockers, beta-adrenergic blockers, diuretics (including loop diuretics), potassium channel activators, endothelin receptor antagonists, endothelin 1 receptor agonists, soluble guanylate cyclase stimulators, vasodilators, HMG-CoA reductase inhibitors, niacin and niacin receptor agonists, Niemann-Pick Cl-like 1 (NPC1L1) inhibitors, insulin or insulin analogs, biguanides (e.g., metformin), sulfonylureas, peroxisome proliferator-activated receptor (PPAR) agonists and partial agonists including PPARγ agonists and other PPAR ligands, dipeptidyl peptidase-4 (DPP4) inhibitors, glucagon-like peptide 1 (GLP-1), GLP-1 receptor agonists, and sodium-glucose co-transporter 2 (SGLT2) inhibitors.

In one aspect, provided are kits comprising an effective amount of a compound of Formula I, in unit dosage form, together with instructions for administering the compound to a subject suffering from or susceptible to a metalloenzyme-mediated disease or disorder, including cancer, cardiovascular disease, endocrinologic disease, inflammatory disease, infectious disease, gynecologic disease, metabolic disease, ophthalmologic disease, central nervous system (CNS) disease, urologic disease, or gastrointestinal disease. In other embodiments, the disease, disorder or symptom thereof is hypertension, resistant hypertension, morbidities associated with primary or secondary hyperaldosteronism and adrenal hyperplasia, pulmonary arterial hypertension, heart failure, diastolic dysfunction, left ventricular diastolic dysfunction, diastolic heart failure, systolic dysfunction, systolic heart failure, hypokalemia, renal failure, chronic renal failure, restenosis, nephropathy, post-myocardial infarction, coronary heart disease, fibrosis, diseases characterized by increased collagen formation, fibrosis and matrix remodeling following hypertension, fibrosis and matrix remodeling following endothelial cell dysfunction, cardiovascular diseases such as atherosclerosis, atrial fibrillation, renal dysfunction, liver diseases, non-alcoholic steatohepatitis, vascular diseases, retinopathy, neuropathy, insulinopathy, endothelial dysfunction, myocardial fibrosis, vascular fibrosis, myocardial necrotic lesions, vascular damage, myocardial infarction, left ventricular hypertrophy, vascular wall hypertrophy, endothelial thickening, fibrinoid necrosis of the arteries, kidney diseases, diabetic nephropathy, glomerulosclerosis, glomerulonephritis, nephritic syndrome, polycystic kidney disease, diabetes mellitus, metabolic syndrome, insulin resistance, sleep apnea, obstructive sleep apnea, muscular dystrophy, liver cirrhosis, non-alcoholic fatty liver disease, renal disorders, diabetic renal disorders, or stroke.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present disclosure contain both basic and acidic functionalities that allow the compounds to be converted into either base or acid addition salts. Other pharmaceutically acceptable carriers known to those of skill in the art are suitable for the present disclosure.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In addition to salt forms, the present disclosure provides compounds which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

The present disclosure also provides a pharmaceutical composition, comprising an effective amount a compound described herein and a pharmaceutically acceptable carrier. In an embodiment, a compound of Formula I is administered to a subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of the disclosure may be varied so as to obtain an amount of the active ingredient which is effective to achieve the desired therapeutic response for a particular patient, composition, and mode of administration, without being toxic (or unacceptably toxic) to the patient.

In use, at least one compound according to the present disclosure is administered in a pharmaceutically effective amount to a subject in need thereof in a pharmaceutical carrier by intravenous, intramuscular, subcutaneous, or intracerebroventricular injection or by oral administration or topical application. In accordance with the present disclosure, a compound of the disclosure may be administered alone or in conjunction with a second, different therapeutic. By "in conjunction with" is meant together, substantially simultaneously or sequentially. In one embodiment, a compound of the disclosure is administered acutely. The compound of the disclosure may therefore be administered for a short course of treatment, such as for about 1 day to about 1 week. In another embodiment, the compound of the disclosure may be administered over a longer period of time to ameliorate chronic disorders, such as, for example, for about one week to several months depending upon the condition to be treated.

By "pharmaceutically effective amount" as used herein is meant an amount of a compound of the disclosure, high enough to significantly positively modify the condition to be treated but low enough to avoid serious side effects (at a reasonable benefit/risk ratio), within the scope of sound medical judgment. A pharmaceutically effective amount of a compound of the disclosure will vary with the particular goal to be achieved, the age and physical condition of the patient being treated, the severity of the underlying disease, the duration of treatment, the nature of concurrent therapy and the specific compound employed. For example, a therapeutically effective amount of a compound of the disclosure administered to a child or a neonate will be reduced proportionately in accordance with sound medical judgment. The effective amount of a compound of the disclosure will thus be the minimum amount which will provide the desired effect.

A decided practical advantage of the present disclosure is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the disclosure may be required to be coated in a material to protect the compound from the action of enzymes, acids and other natural conditions which may inactivate the compound. In order to administer a compound of the disclosure by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

Some examples of substances which can serve as pharmaceutical carriers are sugars, such as lactose, glucose and sucrose; starches such as corn starch and potato starch; cellulose and its derivatives such as sodium carboxymethycellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of theobroma; polyols such as propylene glycol, glycerine, sorbitol, mannitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and echinacea, for example. Wetting agents and lubricants such as sodium lauryl sulfate, as well as coloring agents, flavoring agents, lubricants, excipients, tableting agents, stabilizers, anti-oxidants and preservatives, can also be present. Solubilizing agents, including for example, cremaphore and beta-cyclodextrins can also used in the pharmaceutical compositions herein.

Pharmaceutical compositions comprising the active compounds of the present disclosure (or prodrugs thereof) can be manufactured by means of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries which facilitate processing of the active compounds into preparations which can be used pharmaceutically.

Pharmaceutical compositions of the present disclosure subject matter can take a form suitable for virtually any mode of administration, including, for example, topical, ocular, oral, buccal, systemic, nasal, injection, transdermal, rectal, vaginal, and the like, or a form suitable for administration by inhalation or insufflation.

For topical administration, the active compound(s) or prodrug(s) can be formulated as solutions, gels, ointments, creams, suspensions, and the like.

Systemic formulations include those designed for administration by injection, e.g., subcutaneous, intravenous, intramuscular, intrathecal or intraperitoneal injection, as well as those designed for transdermal, transmucosal, oral, or pulmonary administration.

Useful injectable preparations include sterile suspensions, solutions or emulsions of the active compound(s) in aqueous or oily vehicles. The compositions also can contain formulating agents, such as suspending, stabilizing and/or dispersing agent. The formulations for injection can be presented in unit dosage form (e.g., in ampules or in multidose containers) and can contain added preservatives.

Alternatively, the injectable formulation can be provided in powder form for reconstitution with a suitable vehicle, including but not limited to sterile pyrogen free water, buffer, dextrose solution, and the like, before use. To this end, the active compound(s) can be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions can take the form of, for example, lozenges, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p-hydroxybenzoates or sorbic acid). The preparations also can contain buffer salts, preservatives, flavoring, coloring and sweetening agents as appropriate.

Preparations for oral administration can be suitably formulated to give controlled release of the active compound or prodrug, as is well known.

For buccal administration, the compositions can take the form of tablets or lozenges formulated in a conventional manner.

For rectal and vaginal routes of administration, the active compound(s) can be formulated as solutions (for retention enemas), suppositories, or ointments containing conventional suppository bases, such as cocoa butter or other glycerides.

For nasal administration or administration by inhalation or insufflation, the active compound(s) or prodrug(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5-20 mg/ml); benzalkonium chloride (0.1-0.2 mg/mL); polysorbate 80 (TWEEN® 80; 0.5-5 mg/ml); carboxymethylcellulose sodium or microcrystalline cellulose (1-15 mg/ml); phenylethanol (1-4 mg/ml); and dextrose (20-50 mg/ml). The pH of the final suspension can be adjusted to range from about pH5 to pH7, with a pH of about pH 5.5 being typical.

For ocular administration, the active compound(s) or prodrug(s) can be formulated as a solution, emulsion, suspension, and the like, suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, each of which is incorporated herein by reference in its entirety.

For prolonged delivery, the active compound(s) or prodrug(s) can be formulated as a depot preparation for administration by implantation or intramuscular injection. The active ingredient can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption can be used. To this end, permeation enhancers can be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, each of which is incorporated herein by reference in its entirety.

Alternatively, other pharmaceutical delivery systems can be employed. Liposomes and emulsions are well-known examples of delivery vehicles that can be used to deliver active compound(s) or prodrug(s). Certain organic solvents such as dimethylsulfoxide (DMSO) also can be employed.

The pharmaceutical compositions can, if desired, be presented in a pack or dispenser device which can contain one or more unit dosage forms containing the active compound(s). The pack can, for example, comprise metal or plastic foil, such as a blister pack. The pack or dispenser device can be accompanied by instructions for administration.

The active compound(s) or prodrug(s) of the present disclosure, or compositions thereof, will generally be used in an amount effective to achieve the intended result, for example in an amount effective to treat or prevent the particular disease being treated. The compound(s) can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit also includes halting or slowing the progression of the disease, regardless of whether improvement is realized.

For prophylactic administration, the compound can be administered to a patient at risk of developing one of the previously described diseases. A patient at risk of developing a disease can be a patient having characteristics placing the patient in a designated group of at risk patients, as defined by an appropriate medical professional or group. A patient at risk may also be a patient that is commonly or routinely in a setting where development of the underlying disease that may be treated by administration of a metalloenzyme inhibitor according to the present disclosure could occur. In other words, the at risk patient is one who is commonly or routinely exposed to the disease or illness causing conditions or may be acutely exposed for a limited time. Alternatively, prophylactic administration can be applied to avoid the onset of symptoms in a patient diagnosed with the underlying disorder.

The amount of compound administered will depend upon a variety of factors, including, for example, the particular indication being treated, the mode of administration, whether the desired benefit is prophylactic or therapeutic, the severity of the indication being treated and the age and weight of the patient, the bioavailability of the particular active compound, and the like. Determination of an effective dosage is well within the capabilities of those skilled in the art.

Effective dosages can be estimated initially from in vitro assays. For example, an initial dosage for use in animals can be formulated to achieve a circulating blood or serum concentration of active compound that is at or above an IC50 of the particular compound as measured in as in vitro assay, such as the in vitro fungal MIC or MFC and other in vitro assays described in the Examples section. Calculating dosages to achieve such circulating blood or serum concentrations taking into account the bioavailability of the particular compound is well within the capabilities of skilled artisans. For guidance, see Fingl & Woodbury, "General Principles," In: *Goodman and Gilman's The Pharmaceutical Basis of Therapeutics*, Chapter 1, pp. 1-46, latest edition, Pagamonon Press, and the references cited therein, which are incorporated herein by reference.

Initial dosages also can be estimated from in vivo data, such as animal models. Animal models useful for testing the efficacy of compounds to treat or prevent the various diseases described above are well-known in the art.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. In cases of local administration or selective uptake, such as local topical administration, the effective local concentration of active compound(s) cannot be related to plasma concentration. Skilled artisans will be able to optimize effective local dosages without undue experimentation.

The compound(s) can be administered once per day, a few or several times per day, or even multiple times per day, depending upon, among other things, the indication being treated and the judgment of the prescribing physician.

Preferably, the compound(s) will provide therapeutic or prophylactic benefit without causing substantial toxicity. Toxicity of the compound(s) can be determined using standard pharmaceutical procedures. The dose ratio between toxic and therapeutic (or prophylactic) effect is the therapeutic index. Compounds(s) that exhibit high therapeutic indices are preferred.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

In order that the invention described herein may be more fully understood, the following examples are set forth. The examples described in this application are offered to illustrate the compounds, pharmaceutical compositions, and methods provided herein and are not to be construed in any way as limiting their scope.

General Experimental Procedures

Definitions of variables in the structures in schemes herein are commensurate with those of corresponding positions in the formulae delineated herein. The example compounds listed in Table 2 were characterized by the HPLC and LCMS methods described in Table 1.

TABLE 1

| | HPLC and LCMS methods | |
|---|---|---|
| | HPLC | LCMS |
| a | Column: ZORBAX-SCB-C18 (150 × 4.6 mm, 3.5μ); ACN: 0.05% Aq TFA; 1.0 mL/min | Column: X-Select CSH C-18 (50 × 3.0 mm, 2.5 μm); 2.5 mM $NH_4OOCH$ in water: 5% ACN; ACN: 5% 2.5 mM $NH_4OOCH$ in water: 0.80 mL/min |
| b | Column: X-Select-CSH-C18 (150 × 4.6 mm, 3.5 μm); 0.05% TFA + 5% ACN: ACN + 5% 0.05% TFA; 1.0 mL/min | Column: Kinotex EVO C-18 (50 × 3.0 mm, 2.6 μm); 2.5 mM $NH_4OOCH$ in water: 5% ACN; ACN: 5% 2.5 mM $NH_4OOCH$ in water: 0.80 mL/min |
| c | Column: X-Select-CSH-C18 (150 × 4.6 mm, 3.5 μm); 5 mM $NH_4OAc$: ACN; 1.0 mL/min. | Column: Ascentis Express C-18 (50 × 3.0 mm, 2.7 μm); 0.025% Aq TFA + 5% ACN: ACN: 5% 0.025% Aq TFA: 1.2 mL/min |
| d | Column: X-Select-CSH-C18 (150 × 4.6 mm, 3.5 μm); 5 mM $NH_4CO_3$: ACN; 1.0 mL/min. | Column: X-Select CSH C-18 (50 × 3.0 mm, 2.5 μm); 2.5 mM Aq $NH_4OAc$: ACN; 0.80 mL/min |
| e | Column: Atlantis-T3 (150 × 4.6 mm, 3.0 μm); 5 mM $NH_4OAc$: ACN; 1.0 mL/min. | Column: Kinotex EVO C-18 (50 × 3.0 mm, 2.6 μm); 2.5 mM Aq $NH_4OAc$: ACN; 0.80 mL/m |

Common Abbreviations

ACN acetonitrile
br broad
d doublet
dd doublet of doublets
dba dibenzylideneacetone
DIPEA diisopropylethylamine
dppf 1,1'-ferrocenediyl-bis(diphenylphosphine)
h hour(s)
HRMS high resolution mass spectrometry
HPLC high performance liquid chromatography
LCMS liquid chromatography and mass spectrometry
MS mass spectrometry
MW microwave
m multiplet
min minutes
mL milliliter(s)
m/z mass to charge ratio
NMR nuclear magnetic resonance
ppm parts per million
rt or RT room temperature
s singlet
t triplet
TLC thin layer chromatography

Preparation of Int-1

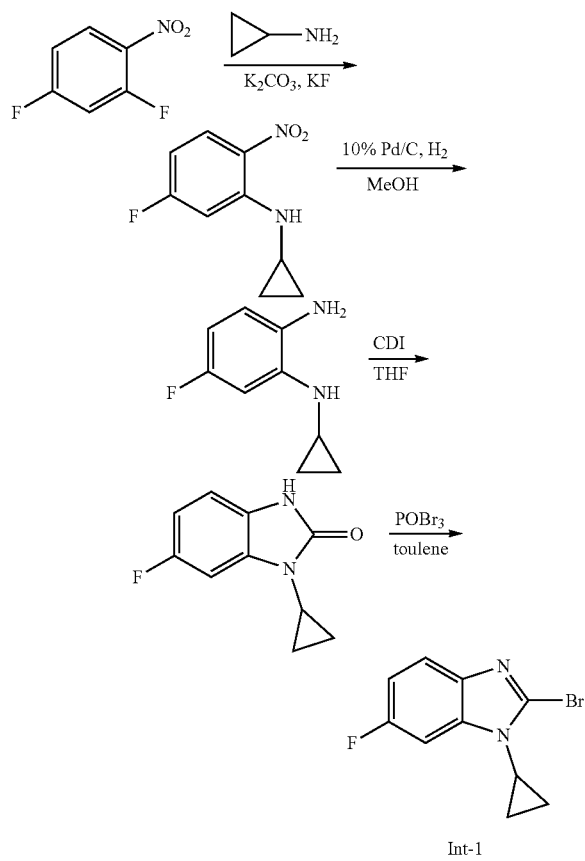

Int-1

N-cyclopropyl-5-fluoro-2-nitroaniline

To 2,4-difluoro-1-nitrobenzene (25 g, 157.23 mmol) was added potassium fluoride (9.12 g, 157.23 mmol) and potassium carbonate (21.7 g, 157.23 mmol) followed by cyclopropanamine (10.75 g, 188.68 mmol) drop wise at room temperature under an inert atmosphere and the reaction was stirred for 2 h. After consumption of starting material (by TLC), the reaction mixture was diluted with water (200 mL) and extracted with EtOAc (2×200 mL). The combined organic extracts were dried over anhydrous $Na_2SO_4$ and concentrated under reduced pressure. The crude material was purified by silica gel column chromatography (eluent: 5% EtOAc/hexane) to afford N-cyclopropyl-5-fluoro-2-nitroaniline 2 (26 g, 132.65 mmol, 84%) as a yellow solid.

$^1$H NMR (500 MHz, CDCl$_3$): δ 8.20 (dd, J=9.3, 6.1 Hz, 1H), 6.95 (dd, J=11.4, 2.7 Hz, 1H), 6.45-6.39 (m, 1H), 2.59-2.53 (m, 1H), 0.97-0.92 (m, 2H), 0.71-0.65 (m, 2H)

N$^1$-cyclopropyl-5-fluorobenzene-1,2-diamine

To a stirred solution of N-cyclopropyl-5-fluoro-2-nitroaniline (24 g, 122.45 mmol) in methanol (300 mL) was added 10% Pd/C (50% wet, 2.4 g) at room temperature under an inert atmosphere. The reaction mixture was stirred at room temperature under hydrogen atmosphere (balloon pressure) for 8 h. After consumption of starting material (by TLC), the reaction mixture was filtered through a pad of Celite and washed with methanol (100 mL). The filtrate was concentrated under reduced pressure to afford N$^1$-cyclopropyl-5-fluorobenzene-1,2-diamine (18 g, 108.43 mmol, 88%) as a brown syrup.

$^1$H NMR (400 MHz, DMSO-d$_6$): δ 6.52 (dd, J=11.6, 2.8 Hz, 1H), 6.45 (dd, J=8.4, 6.0 Hz, 1H), 6.18 (td, J=8.5, 2.9 Hz, 1H), 5.28 (s, 1H), 4.30 (brs, 2H), 2.36-2.28 (m, 1H), 0.74-0.68 (m, 2H), 0.42-0.37 (m, 2H)

LC-MS: m/z 166.8 [M+H]$^+$ at 1.64 RT (72.46% purity)

1-cyclopropyl-6-fluoro-1,3-dihydro-2H-benzo[d]imidazol-2-one

To a stirred solution of N$^1$-cyclopropyl-5-fluorobenzene-1,2-diamine (1 g, 6.02 mmol) in THF (20 mL) was added 1,1'-carbonyldiimidazole (1.46 g, 9.04 mmol) at room temperature under an inert atmosphere and the reaction mixture was stirred for 16 h. After consumption of starting material (by TLC), the reaction mixture was diluted with EtOAc (60 mL) and washed with 1 N HCl (10 mL). The organic layer was separated, dried over anhydrous Na$_2$SO$_4$ and concentrated under reduced pressure to afford 1-cyclopropyl-6-fluoro-1,3-dihydro-2H-benzo[d]imidazol-2-one (1 g) as a black solid. The crude material was taken to the next step without further purification.

$^1$H NMR (400 MHz, CDCl$_3$): δ 9.75 (brs, 1H), 7.00-6.93 (m, 2H), 6.81-6.74 (m, 1H), 2.92-2.84 (m, 1H), 1.16-1.12 (m, 2H), 1.06-1.01 (m, 2H)

2-bromo-1-cyclopropyl-6-fluoro-1H-benzo[d]imidazole (Int-1)

To a stirred solution of 1-cyclopropyl-6-fluoro-1,3-dihydro-2H-benzo[d]imidazol-2-one (1 g, crude) in toluene (30 mL) was added phosphoryl bromide (5.97 g, 20.83 mmol) at room temperature under an inert atmosphere. The reaction mixture was heated to 110° C. and stirred for 16 h. After consumption of starting material (by TLC), the reaction mixture was diluted with CH$_2$Cl$_2$ (50 mL), warm water (50 mL) and stirred for 30 min. Then the reaction mixture was basified using aqueous Na$_2$CO$_3$ solution to pH~10 and extracted with CH$_2$Cl$_2$ (2×50 mL). The combined organic extracts were washed with water (30 mL), dried over anhydrous Na$_2$SO$_4$ and concentrated under reduced pressure. The crude material was purified by silica gel column chromatography (eluent: 30% EtOAc/hexane) to afford 2-bromo-1-cyclopropyl-6-fluoro-1H-benzo[d]imidazole Int-1 (600 mg, 2.35 mmol, 39% for two steps) as a pale yellow syrup.

$^1$H NMR (500 MHz, CDCl$_3$): δ 7.60 (dd, J=8.7, 4.9 Hz, 1H), 7.22 (dd, J=8.7, 2.3 Hz, 1H), 7.00 (td, J=9.3, 2.6 Hz, 1H), 3.25-3.18 (m, 1H), 1.33-1.28 (m, 2H), 1.18-1.13 (m, 2H) LC-MS: m/z 254.9 [M+H]$^+$ at 2.49 RT (95.00% purity)

Preparation of Int-2

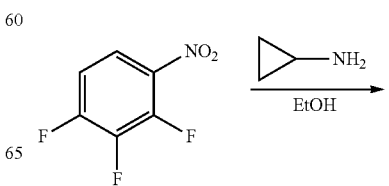

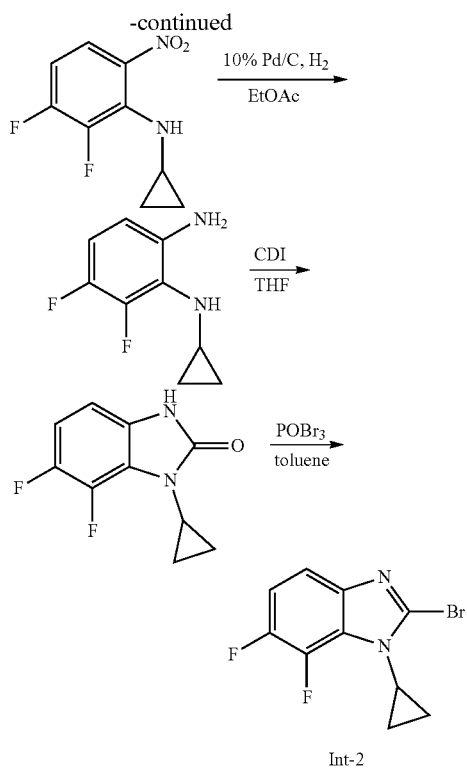

N-cyclopropyl-2,3-difluoro-6-nitroaniline

To a stirred solution of 1,2,3-trifluoro-4-nitrobenzene (10 g, 56.5 mmol) in ethanol (200 mL) was added cyclopropanamine (3.22 g, 56.5 mmol) drop wise at room temperature under an inert atmosphere and stirred for 16 h. After consumption of starting material (by TLC), the volatiles were removed under reduced pressure to obtain the crude material. The crude material was purified by silica gel column chromatography (eluent: 10% EtOAc/hexane) to afford N-cyclopropyl-2,3-difluoro-6-nitroaniline (8 g, 37.38 mmol, 66%) as a pale yellow viscous syrup. $^1$H NMR (500 MHz, DMSO-$d_6$): δ 7.96-7.91 (m, 1H), 7.75 (brs, 1H), 6.87-6.80 (m, 1H), 3.03-2.97 (m, 1H), 0.78-0.72 (m, 2H), 0.68-0.63 (m, 2H)

$N^1$-cyclopropyl-5,6-difluorobenzene-1,2-diamine

To a stirred solution of N-cyclopropyl-2,3-difluoro-6-nitroaniline (8 g, 37.38 mmol) in ethylacetate (200 mL) was added 10% Pd/C (50% wet, 2 g) at room temperature under an inert atmosphere. The reaction mixture was stirred at room temperature under hydrogen atmosphere (balloon pressure) for 6 h. After consumption of starting material (by TLC), the reaction mixture was filtered through a pad of Celite and washed with methanol (60 mL). The filtrate was concentrated under reduced pressure. The crude material was purified by silica gel column chromatography (eluent: 10% EtOAc/hexane) to afford $N^1$-cyclopropyl-5,6-difluorobenzene-1,2-diamine (4.3 g, 23.37 mmol, 62%) as a brown viscous syrup.
$^1$H NMR (400 MHz, DMSO-$d_6$): δ 6.55-6.46 (m, 1H), 6.32-6.26 (m, 1H), 4.69 (s, 2H), 4.54 (brs, 1H), 2.73-2.65 (m, 1H), 0.58-0.52 (m, 2H), 0.48-0.42 (m, 2H)
LC-MS: m/z 185.0 [M+H]$^+$ at 2.97 RT (61.14% purity)

1-cyclopropyl-67-difluoro-1,3-dihydro-2H-benzo[d]imidazol-2-one

To a stirred solution of $N^1$-cyclopropyl-5,6-difluorobenzene-1,2-diamine (500 mg, 2.72 mmol) in THF (10 mL) was added 1,1'-carbonyldiimidazole (660 mg, 4.08 mmol) at room temperature under an inert atmosphere and stirred for 16 h. After consumption of starting material (by TLC), the reaction mixture was diluted with water (30 mL) and extracted with EtOAc (2×30 mL). The combined organic extracts were dried over anhydrous Na$_2$SO$_4$ and concentrated under reduced pressure to afford 1-cyclopropyl-6,7-difluoro-1,3-dihydro-2H-benzo[d]imidazol-2-one (600 mg) as a brown viscous syrup. The crude material was taken to the next step without further purification.
LC-MS: m/z 208.9 [M−H]$^−$ at 2.80 RT (47.16% purity) & m/z 208.9 [M−H]$^−$ at 4.05 RT (33.71% purity)

2-bromo-1-cyclopropyl-6,7-difluoro-1H-benzo[d]imidazole (Int-2)

To a stirred solution of 1-cyclopropyl-6,7-difluoro-1,3-dihydro-2H-benzo[d]imidazol-2-one (600 mg, crude) in toluene (10 mL) was added phosphoryl bromide (3.29 g, 11.43 mmol) at room temperature under an inert atmosphere. The reaction mixture was heated to 100° C. and stirred for 16 h. After consumption of starting material (by TLC), the reaction mixture was quenched with saturated NaHCO$_3$ to pH~8 and extracted with EtOAc (2×30 mL). The combined organic extracts were dried over anhydrous Na$_2$SO$_4$ and concentrated under reduced pressure. The crude material was purified by silica gel column chromatography (eluent: 10% EtOAc/hexane) to afford 2-bromo-1-cyclopropyl-6,7-difluoro-1H-benzo[d]imidazole Int-2 (100 mg, 0.37 mmol, 13% for two steps) as an off white solid.
$^1$H NMR (500 MHz, DMSO-$d_6$): δ 7.42 (dd, J=8.8, 3.6 Hz, 1H), 7.32-7.24 (m, 1H), 3.56-3.50 (m, 1H), 1.28-1.16 (m, 4H)
LC-MS: m/z 272.8 [M+H]$^+$ at 3.30 RT (73.30% purity)

Preparation of Int-3

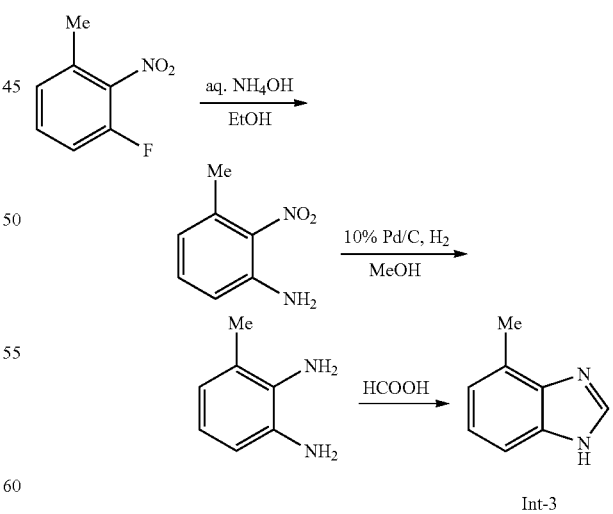

3-methyl-2-nitroaniline

To a stirred solution of 1-fluoro-3-methyl-2-nitrobenzene (1 g, 6.45 mmol) in ethanol (10 mL) was added aqueous ammonium hydroxide (30%, 10 mL) in a sealed tube at 0° C. The reaction mixture was heated to 80° C. and stirred for 24 h. After consumption of starting material (by TLC), the reaction mixture was diluted with water (40 mL) and extracted with Et$_2$O (2×40 mL). The combined organic extracts were dried over anhydrous Na$_2$SO$_4$ and concentrated under reduced pressure to afford 3-methyl-2-nitroaniline (1.2 g) as a pale yellow solid. The crude material was taken to the next step without further purification.

LC-MS: m/z 153.0 [M+H]$^+$ at 2.15 RT (36.85% purity)

3-methylbenzene-1,2-diamine

To a stirred solution of 3-methyl-2-nitroaniline (1.2 g, crude) in methanol (15 mL) was added 10% Pd/C (50% wet, 150 mg) at room temperature under an inert atmosphere. The reaction mixture was stirred at room temperature under hydrogen atmosphere (balloon pressure) for 2 h. After consumption of starting material (by TLC), the reaction mixture was filtered through a pad of Celite and washed with methanol (40 mL). The filtrate was concentrated under reduced pressure to afford 3-methylbenzene-1,2-diamine (900 mg) as a brown solid. The crude material was taken to the next step without further purification.

4-methyl-1H-benzo[d]imidazole (Int-3)

A solution of 3-methylbenzene-1,2-diamine (900 mg, crude) in formic acid (5 mL) under an inert atmosphere was heated to 90° C. and stirred for 16 h. After consumption of starting material (by TLC), the reaction mixture was basified with saturated Na$_2$CO$_3$ solution to pH~8 and extracted with EtOAc (2×40 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 4-methyl-1H-benzo[d]imidazole Int-3 (120 mg, 0.91 mmol, 14%, overall yield in three steps) as a pale yellow solid.

$^1$H NMR (400 MHz, CD$_3$OD): δ 8.12 (s, 1H), 7.45-7.39 (m, 1H), 7.15 (t, J=7.7 Hz, 1H), 7.05 (d, J=7.3 Hz, 1H), 2.57 (s, 3H)

Preparation of Int-4

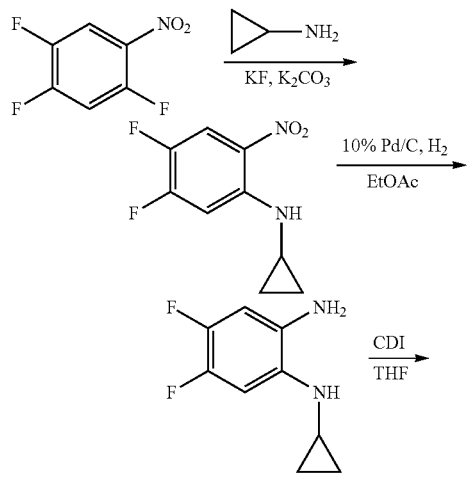

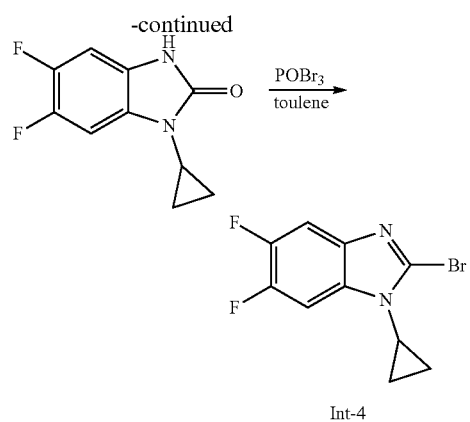

N-cyclopropyl-4,5-difluoro-2-nitroaniline

To a mixture of 1,2,4-trifluoro-5-nitrobenzene (500 mg, 2.82 mmol) in potassium fluoride (164 mg, 2.82 mmol) was added potassium carbonate (390 mg, 2.82 mmol) and cyclopropanamine (0.23 mL, 3.39 mmol) drop wise at 0° C. under an inert atmosphere. The reaction mixture was stirred at 0° C. for 30 min. After consumption of starting material (by TLC), the reaction mixture was diluted with water (20 mL) and extracted with EtOAc (2×20 mL). The combined organic extracts were dried over anhydrous Na$_2$SO$_4$ and concentrated under reduced pressure to afford N-cyclopropyl-4,5-difluoro-2-nitroaniline (320 mg) as a pale yellow solid. The crude material was taken to the next step without further purification.

LC-MS: m/z 215.4 [M+H]$^+$ at 4.43 RT (69.03% purity)

N$^1$-cyclopropyl-4,5-difluorobenzene-1,2-diamine

To a stirred solution of N-cyclopropyl-4,5-difluoro-2-nitroaniline (300 mg, crude) in ethylacetate (10 mL) was added 10% Pd/C (50% wet, 30 mg) at room temperature under an inert atmosphere. The reaction mixture was stirred at room temperature under hydrogen atmosphere (balloon pressure) for 4 h. After consumption of starting material (by TLC), the reaction mixture was filtered through a pad of Celite and washed with methanol (15 mL) and EtOAc (10 mL). The filtrate was concentrated under reduced pressure to afford N$^1$-cyclopropyl-4,5-difluorobenzene-1,2-diamine (100 mg) as a brown viscous syrup. The crude material was taken to the next step without further purification.

LC-MS: m/z 184.9 [M+H]$^+$ at 2.12 RT (83.53% purity)

1-cyclopropyl-5,6-difluoro-1,3-dihydro-2H-benzo[d] imidazol-2-one

To a stirred solution of N$^1$-cyclopropyl-4,5-difluorobenzene-1,2-diamine (500 mg, crude) in THF (10 mL) was added 1,1'-carbonyldiimidazole (430 mg, 2.64 mmol) at room temperature under an inert atmosphere and stirred for 16 h. After consumption of starting material (by TLC), the reaction mixture was diluted with EtOAc (60 mL) and washed with 1 N HCl (10 mL). The organic layer was separated, dried over anhydrous Na$_2$SO$_4$ and concentrated under reduced pressure to afford 1-cyclopropyl-5,6-difluoro-1,3-dihydro-2H-benzo[d]imidazol-2-one (500 mg, crude) as a black solid. The crude material was taken to the next step without further purification.

2-bromo-1-cyclopropyl-5,6-difluoro-1H-benzo[d] imidazole (Int-4)

To a stirred solution of 1-cyclopropyl-5,6-difluoro-1,3-dihydro-2H-benzo[d]imidazol-2-one (500 mg, crude) in toluene (20 mL) was added phosphoryl bromide (2.73 g, 9.52 mmol) at room temperature under an inert atmosphere. The reaction mixture was heated to 80° C. and stirred for 16 h. After consumption of starting material (by TLC), the reaction mixture was diluted with water (20 mL), heated to 40° C. and stirred for 30 min. The mixture was basified using saturated $Na_2CO_3$ solution (30 mL) and extracted with $CH_2Cl_2$ (2×30 mL). The combined organic extracts were dried over anhydrous $Na_2SO_4$ and concentrated under reduced pressure. The crude material was purified by silica gel column chromatography (eluent: 10% EtOAc/hexane) to afford 2-bromo-1-cyclopropyl-5,6-difluoro-1H-benzo[d] imidazole Int-4 (300 mg, 1.09 mmol, 46% for two steps) as a brown solid.

$^1$H NMR (400 MHz, DMSO-$d_6$): δ 7.13-7.69 (m, 2H), 3.38-3.33 (m, 1H), 1.29-1.21 (m, 2H), 1.11-1.03 (m, 2H)

Preparation of Int-5

Scheme:

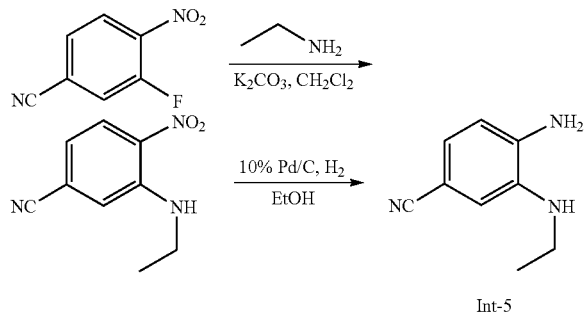

3-(ethylamino)-4-nitrobenzonitrile

To a stirred solution of 3-fluoro-4-nitrobenzonitrile (2 g, 12.05 mmol) in $CH_2Cl_2$ (250 mL) was added potassium carbonate (3.32 g, 24.09 mmol) and ethylamine (Aq. 70%, 2.17 g, 48.19 mmol) at room temperature under an inert atmosphere. The reaction mixture was stirred at room temperature for 6 h. After consumption of starting material (by TLC), the reaction mixture was quenched with water (60 mL) and extracted with EtOAc (2×60 mL). The combined organic extracts were dried over anhydrous $Na_2SO_4$ and concentrated under reduced pressure to afford 3-(ethylamino)-4-nitrobenzonitrile (1.9 g) as a yellow solid. The crude material was taken to the next step without further purification.

$^1$H NMR (500 MHz, DMSO-$d_6$): δ 8.22-8.10 (m, 2H), 7.58 (brs, 1H), 7.00 (d, J=8.7 Hz, 1H), 3.48-3.38 (m, 2H), 1.21 (t, J=6.9 Hz, 3H)

LC-MS: m/z 192.1 $[M+H]^+$ at 4.10 RT (98.96% purity)

4-amino-3-(ethylamino) benzonitrile (Int-5)

To a stirred of solution of 3-(ethylamino)-4-nitrobenzonitrile (1.9 g, crude) in ethanol (20 mL) was added 10% Pd/C (50% wet, 190 mg) at room temperature under an inert atmosphere. The reaction mixture was stirred at room temperature under hydrogen atmosphere (balloon pressure) for 5 h. After consumption of starting material (by TLC), the reaction mixture was filtered through a pad of Celite and washed with methanol (50 mL) and EtOAc (30 mL). The filtrate was concentrated under reduced pressure to obtain 4-amino-3-(ethylamino) benzonitrile Int-5 (1.5 g) as an off white solid. The crude material was taken to the next step without further purification.

LC-MS: m/z 161.9 $[M+H]^+$ at 2.11 RT (60.88% purity)

Preparation of Int-6

Scheme:

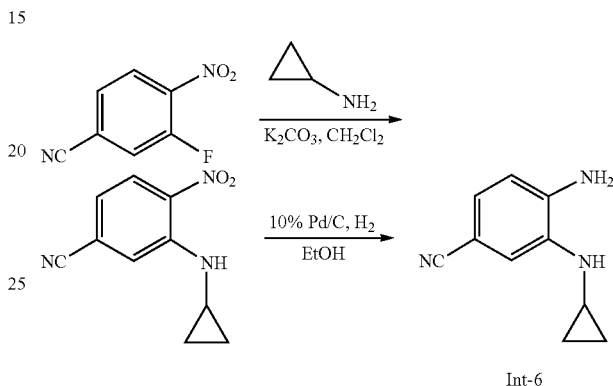

3-(cyclopropylamino)-4-nitrobenzonitrile

To a stirred solution of 3-fluoro-4-nitrobenzonitrile (1 g, 6.02 mmol) in $CH_2Cl_2$ (5 mL) was added potassium carbonate (1.66 g, 12.05 mmol) and cyclopropanamine (3.33 mL, 48.19 mmol) drop wise at room temperature under an inert atmosphere. The reaction mixture was stirred at room temperature for 4 h. After consumption of starting material (by TLC), the reaction mixture was diluted with water (30 mL) and extracted with EtOAc (2×40 mL). The combined organic extracts were dried over anhydrous $Na_2SO_4$ and concentrated under reduced pressure to obtain 3-(cyclopropylamino)-4-nitrobenzonitrile (900 mg) as a yellow solid. The crude material was taken to next step without further purification.

$^1$H NMR (400 MHz, CDCl$_3$): δ 8.24 (d, J=8.7 Hz, 1H), 8.07 (brs, 1H), 7.64 (d, J=1.7 Hz, 1H), 6.93 (dd, J=8.7, 1.7 Hz, 1H), 2.62-2.57 (m, 1H), 1.03-0.97 (m, 2H), 0.72-0.67 (m, 2H)

LC-MS: m/z 201.9 $[M-H]^-$ at 3.25 RT (99.61% purity)

4-amino-3-(cyclopropylamino)benzonitrile (Int-6)

To a stirred of solution of 3-(cyclopropylamino)-4-nitrobenzonitrile (900 mg, crude) in ethanol (10 mL) was added 10% Pd/C (50% wet, 500 mg) at room temperature under an inert atmosphere. The reaction mixture was stirred at room temperature under hydrogen atmosphere (balloon pressure) for 5 h. After consumption of starting material (by TLC), the reaction mixture was filtered through a pad of Celite and washed with EtOAc (30 mL). The filtrate was concentrated under reduced pressure. The crude material was purified by silica gel column chromatography (eluent: 20% EtOAc/hexane) to afford 4-amino-3-(cyclopropylamino)benzonitrile Int-6 (500 mg, 2.89 mmol, 48% for two steps) as an off white solid.

$^1$H NMR (400 MHz, DMSO-$d_6$): δ 6.93 (d, J=1.9 Hz, 1H), 6.87 (dd, J=8.0, 1.9 Hz, 1H), 6.55 (d, J=8.0 Hz, 1H), 5.49 (s, 2H), 5.43 (s, 1H), 2.40-2.34 (m, 1H), 0.77-0.71 (m, 2H), 0.42-0.37 (m, 2H)

Preparation of Int-7

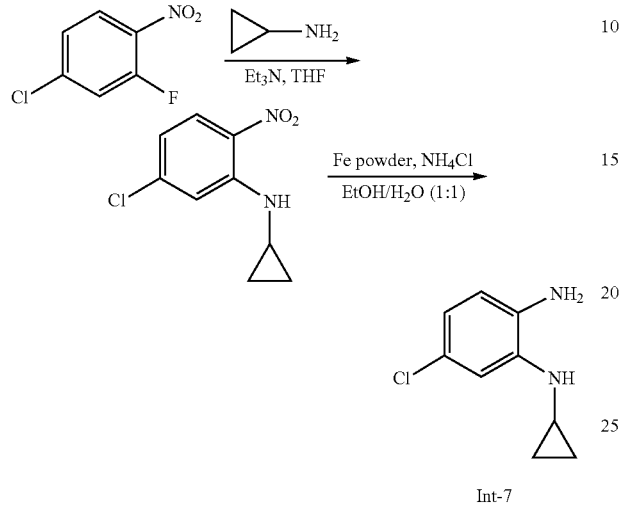

Int-7

5-chloro-N-cyclopropyl-2-nitroaniline

To a stirred solution of 4-chloro-2-fluoro-1-nitrobenzene (1 g, 5.7 mmol) in THF (20 mL) was added triethylamine (2.38 mL, 17.09 mmol) and cyclopropanamine (0.43 mL, 6.27 mmol) at room temperature under an inert atmosphere. The reaction mixture was heated to 80° C. and stirred for 16 h. After consumption of starting material (by TLC), the reaction mixture was diluted with ice cold water (40 mL) and extracted with EtOAc (2×40 mL). The combined organic extracts were dried over anhydrous Na$_2$SO$_4$ and concentrated under reduced pressure. The crude material was purified by silica gel column chromatography (eluent: 2% EtOAc/hexane) to afford 5-chloro-N-cyclopropyl-2-nitroaniline (1 g, 4.72 mmol, 83%) as a yellow solid.

$^1$H NMR (400 MHz, DMSO-$d_6$): δ 8.08 (d, J=9.2 Hz, 2H), 7.37 (d, J=2.3 Hz, 1H), 6.79 (dd, J=9.2, 2.3 Hz, 1H), 2.69-2.63 (m, 1H), 0.92-0.86 (m, 2H), 0.68-0.61 (m, 2H)

LC-MS: m/z 213.2 [M+H]$^+$ at 4.68 RT (97.21% purity)

5-chloro-N$^1$-cyclopropylbenzene-1,2-diamine (Int-7)

To a stirred of solution of 5-chloro-N-cyclopropyl-2-nitroaniline (250 mg, 1.27 mmol) in a mixture of ethanol/water (1:1, 10 mL) was added Iron powder (356 mg, 6.38 mmol) and ammonium chloride (341 mg, 6.38 mmol) at room temperature. The reaction mixture was heated to 80° C. and stirred for 5 h. After consumption of starting material (by TLC), the reaction mixture was filtered through a pad of Celite and washed with ethanol (30 mL). The filtrate was concentrated under reduced pressure to afford 5-chloro-N$^1$-cyclopropylbenzene-1,2-diamine Int-7 (200 mg) as brown syrup. The crude material was taken to the next step without further purification.

$^1$H NMR (500 MHz, DMSO-$d_6$): δ 6.69 (d, J=2.3 Hz, 1H), 6.50-6.40 (m, 2H), 5.28 (brs, 1H), 4.64 (brs, 2H), 2.37-2.30 (m, 1H), 0.75-0.69 (m, 2H), 0.42-0.37 (m, 2H)

LC-MS: m/z 182.9 [M+H]$^+$ at 2.85 RT (86.58% purity)

Preparation of Int-8

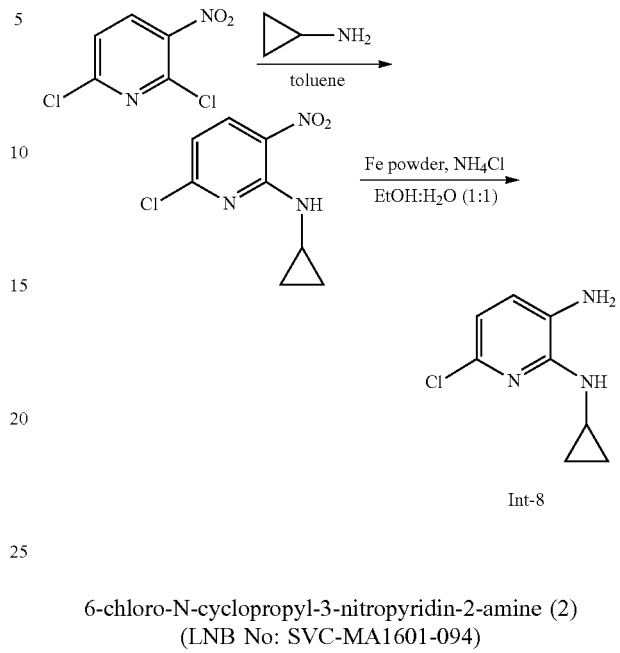

Int-8

6-chloro-N-cyclopropyl-3-nitropyridin-2-amine (2) (LNB No: SVC-MA1601-094)

To a stirred solution of 2,6-dichloro-3-nitropyridine (5 g, 26.04 mmol) in toluene (25 mL) was added cyclopropyl amine (3.7 mL, 52.08 mmol) at 0° C. under an inert atmosphere. The reaction mixture was stirred at 0° C. for 1 h. The reaction mixture was warmed to room temperature and stirred for 2 h. After consumption of starting material (by TLC), the reaction mixture was diluted with water (50 mL) and extracted with EtOAc (2×50 mL). The combined organic extracts were washed with brine (20 mL), dried over anhydrous Na$_2$SO$_4$ and concentrated under reduced pressure. The crude material was purified by silica gel column chromatography (eluent: 10% EtOAc/hexane) to afford 6-chloro-N-cyclopropyl-3-nitropyridin-2-amine (4 g, 18.77 mmol, 72%) as a pale yellow solid.

$^1$H NMR (500 MHz, CDCl$_3$): δ 8.34 (d, J=8.7 Hz, 2H), 6.66 (d, J=8.7 Hz, 1H), 3.10-3.05 (m, 1H), 0.97-0.93 (m, 2H), 0.67-0.64 (m, 2H)

6-chloro-N$^2$-cyclopropylpyridine-2,3-diamine (Int-8)

To a stirred solution of 6-chloro-N-cyclopropyl-3-nitropyridin-2-amine (1 g, 4.69 mmol) in ethanol/water (1:1, 10 mL) was added iron powder (1.3 g, 23.47 mmol) and ammonium chloride (1.2 g, 23.47 mmol) at room temperature. The reaction mixture was heated to 80° C. for 1 h. After consumption of starting material (by TLC), the reaction mixture was diluted with water (20 mL) and extracted with EtOAc (2×20 mL). The combined organic extracts were washed with brine (20 mL), dried over anhydrous Na$_2$SO$_4$ and concentrated under reduced pressure to obtain 6-chloro-N$^2$-cyclopropylpyridine-2,3-diamine Int-8 (700 mg, crude) as a pale yellow solid. The crude material was taken to the next step without further purification.

LC-MS: m/z 183.9 [M+H]$^+$ at 2.07 RT (58.13% purity)

Example 1

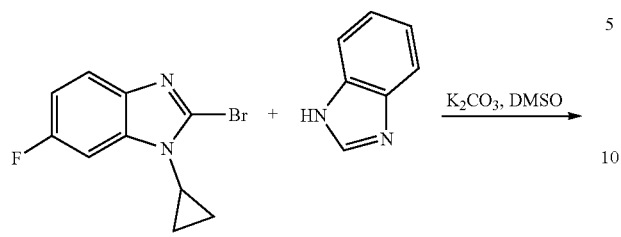

Int-1

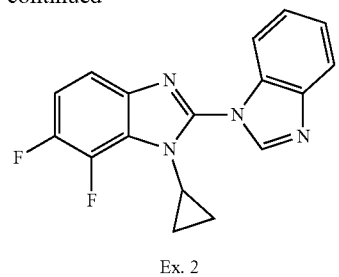

Ex. 2

1'-cyclopropyl-6',7'-difluoro-1'H-1,2'-bibenzo[d]imidazole (Ex. 2)

To a stirred solution of 2-bromo-1-cyclopropyl-6,7-difluoro-1H-benzo[d]imidazole Int-2 (100 mg, 0.37 mmol) in DMSO (2 mL) was added potassium carbonate (152 mg, 1.1 mmol) and 1H-benzo[d]imidazole (87 mg, 0.73 mmol) at room temperature under an inert atmosphere. The reaction mixture was heated to 100° C. and stirred for 16 h. After consumption of starting material (by TLC), the reaction mixture was diluted with water (15 mL) and extracted with $CH_2Cl_2$ (2×20 mL). The combined organic extracts were dried over anhydrous $Na_2SO_4$ and concentrated under reduced pressure. The crude material was purified by silica gel column chromatography (eluent: 30% EtOAc/hexane) to afford 1'-cyclopropyl-6',7'-difluoro-1'H-1,2'-bibenzo[d]imidazole Ex. 2 (20 mg, 0.06 mmol, 17%) as a white solid.

$^1$H NMR (500 MHz, DMSO-$d_6$): δ 8.88 (s, 1H), 7.89-7.82 (m, 2H), 7.58 (dd, J=8.8, 3.3 Hz, 1H), 7.44-7.35 (m, 3H), 3.94-3.87 (m, 1H), 0.97-0.92 (m, 2H), 0.74-0.70 (m, 2H)

LC-MS: m/z 310.9 [M+H]$^+$ at 3.21 RT (97.98% purity)
HPLC: 92.97%

Ex. 1

1'-cyclopropyl-6'-fluoro-1'H-1,2'-bibenzo[d]imidazole (Ex. 1)

To a stirred solution of 2-bromo-1-cyclopropyl-6-fluoro-1H-benzo[d]imidazole Int-1 (150 mg, 0.59 mmol) in DMSO (5 mL) was added 1H-benzo[d]imidazole (139 mg, 1.18 mmol) and potassium carbonate (243 mg, 1.76 mmol) at room temperature under an inert atmosphere. The reaction mixture was heated to 100° C. and stirred for 16 h. After consumption of starting material (by TLC), the reaction mixture was diluted with ice cold water (20 mL) and extracted with EtOAc (2×30 mL). The combined organic extracts were dried over anhydrous $Na_2SO_4$ and concentrated under reduced pressure. The crude material was purified by silica gel column chromatography (eluent: 30% EtOAc/hexane) to afford 1'-cyclopropyl-6'-fluoro-1'H-1,2'-bibenzo[d]imidazole Ex. 1 (90 mg, 0.31 mmol, 52%) as an off white solid.

$^1$H NMR (500 MHz, DMSO-$d_6$): δ 8.90 (s, 1H), 7.87-7.82 (m, 2H), 7.77 (dd, J=8.8, 4.8 Hz, 1H), 7.55 (dd, J=9.0, 2.6 Hz, 1H), 7.43-7.36 (m, 2H), 7.23-7.17 (m, 1H), 3.73-3.68 (m, 1H), 1.02-0.96 (m, 2H), 0.65-0.61 (m, 2H)

LC-MS: m/z 292.9 [M+H]$^+$ at 2.96 RT (99.33% purity)
HPLC: 99.03%

Example 2

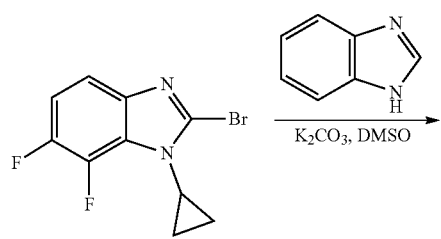

Int-2

Example 3

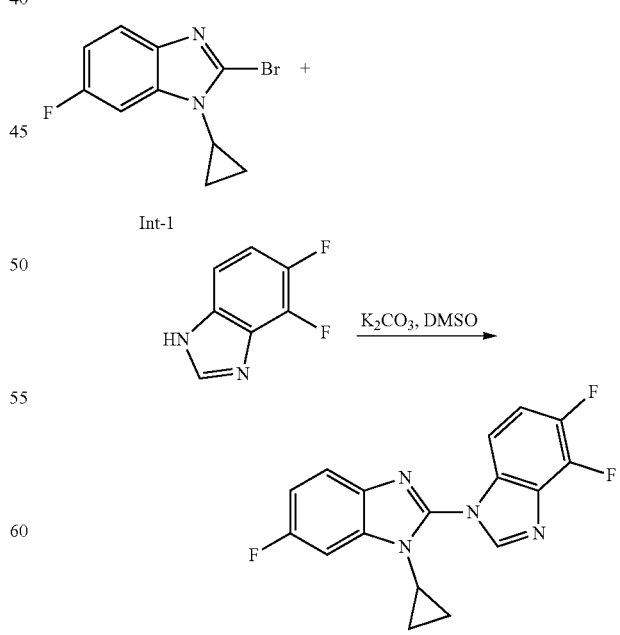

Ex. 3

1'-cyclopropyl-4,5,6'-trifluoro-1'H-1,2'-bibenzo[d]imidazole (Ex. 3)

To a stirred solution of 4,5-difluoro-1H-benzo[d]imidazole (241 mg, 1.57 mmol) in DMSO (5 mL) was added potassium carbonate (325 mg, 2.35 mmol) at room temperature under an inert atmosphere and stirred for 15 min. 2-Bromo-1-cyclopropyl-6-fluoro-1H-benzo[d] imidazole Int-1 (200 mg, 0.78 mmol) was added at room temperature and the reaction mixture was heated to 100° C. and stirred for 16 h. After consumption of starting material (by TLC), the reaction mixture was diluted with ice cold water (25 mL). The precipitated solid was filtered and dried under vacuum to obtain the crude. The crude material was purified by silica gel column chromatography (eluent: 20% EtOAc/hexane) to afford 1'-cyclopropyl-4,5,6'-trifluoro-1'H-1,2'-bibenzo[d]imidazole Ex. 3 (120 mg, 0.36 mmol, 47%) as an off white solid. The structure was further confirmed by 2 D NMR (NOESY, DQFCOSY).

$^1$H NMR (400 MHz, DMSO-$d_6$): δ 9.03 (s, 1H), 7.78 (dd, J=8.8, 4.8 Hz, 1H), 7.73-7.67 (m, 1H), 7.57 (dd, J=9.0, 2.4 Hz, 1H), 7.53-7.44 (m, 1H), 7.25-7.18 (m, 1H), 3.73-3.65 (m, 1H), 1.04-0.98 (m, 2H), 0.69-0.63 (m, 2H)

LC-MS: m/z 328.9 [M+H]$^+$ at 3.31 RT (99.92% purity)
HPLC: 99.82%

Example 4

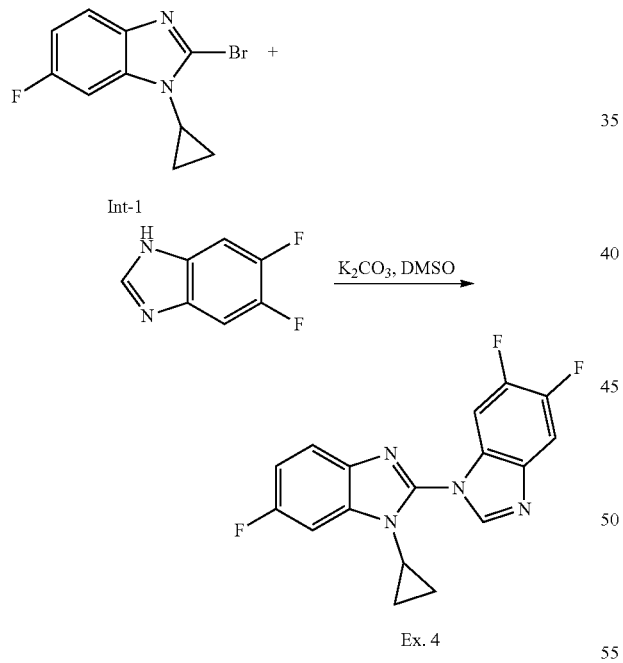

Ex. 4

1'-cyclopropyl-5,6,6'-trifluoro-1'H-1,2'-bibenzo[d]imidazole (Ex. 4)

To a stirred solution of 5,6-difluoro-1H-benzo[d]imidazole (241 mg, 1.57 mmol) in DMSO (5 mL) was added potassium carbonate (325 mg, 2.35 mmol) at room temperature under an inert atmosphere and stirred for 15 min. Then 2-bromo-1-cyclopropyl-6-fluoro-1H-benzo[d]imidazole Int-1 (200 mg, 0.78 mmol) was added at room temperature and the reaction mixture was heated to 100° C. and stirred for 16 h. After consumption of starting material (by TLC), the reaction mixture was diluted with ice cold water (30 mL). The precipitated solid was filtered and dried under vacuum to obtain the crude. The crude material was purified by silica gel column chromatography (eluent: 20% EtOAc/hexane) to afford 1'-cyclopropyl-5,6,6'-trifluoro-1'H-1,2'-bibenzo[d]imidazole Ex. 4 (120 mg, 0.36 mmol, 47%) as a white solid.

$^1$H NMR (400 MHz, DMSO-$d_6$): δ 8.98 (s, 1H), 7.98-7.92 (m, 2H), 7.78 (dd, J=8.8, 4.9 Hz, 1H), 7.56 (dd, J=9.0, 2.4 Hz, 1H), 7.23-7.18 (m, 1H), 3.72-3.67 (m, 1H), 1.03-0.97 (m, 2H), 0.69-0.64 (m, 2H)

LC-MS: m/z 328.9 [M+H]$^+$ at 3.09 RT (99.22% purity)
HPLC: 99.79%

Example 5

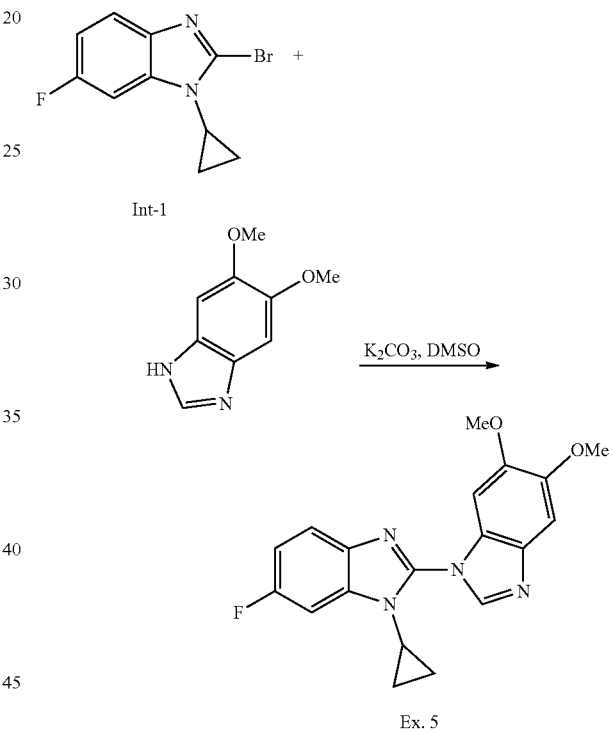

Ex. 5

1'-cyclopropyl-6'-fluoro-5,6-dimethoxy-1'H-1,2'-bibenzo[d]imidazole (Ex. 5)

To a stirred solution of 2-bromo-1-cyclopropyl-6-fluoro-1H-benzo[d]imidazole Int-1 (100 mg, 0.39 mmol) in DMSO (2 mL) was added potassium carbonate (164 mg, 1.18 mmol) and 5,6-dimethoxy-1H-benzo[d]imidazole (70 mg, 0.39 mmol) at room temperature under an inert atmosphere. The reaction mixture was heated to 80° C. and stirred for 16 h. After consumption of starting material (by TLC), the reaction mixture was diluted with water (25 mL) and extracted with EtOAc (2×20 mL). The combined organic extracts were dried over anhydrous Na$_2$SO$_4$ and concentrated under reduced pressure. The crude material was purified by silica gel column chromatography (eluent: 40% EtOAc/hexane) to afford 1'-cyclopropyl-6'-fluoro-5,6-dimethoxy-1'H-1,2'-bibenzo[d]imidazole Ex. 5 (100 mg, 0.28 mmol, 72%) as an off white solid.

¹H NMR (500 MHz, DMSO-d₆): δ 8.64 (s, 1H), 7.77 (dd, J=8.7, 4.9 Hz, 1H), 7.54 (dd, J=9.0, 2.3 Hz, 1H), 7.36 (d, J=2.6 Hz, 2H), 7.22-7.16 (m, 1H), 3.85 (s, 3H), 3.78 (s, 3H), 3.69-3.65 (m, 1H), 0.99-0.93 (m, 2H), 0.63-0.58 (m, 2H)

LC-MS: m/z 353.0 [M+H]⁺ at 2.13 RT (98.91% purity) HPLC: 98.37%

Example 6 & Example 7

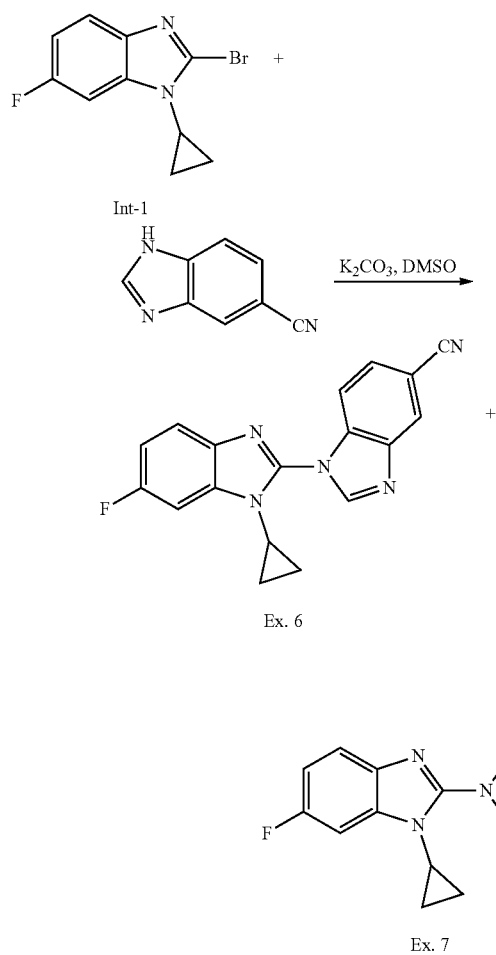

Ex. 6

Ex. 7

1'-cyclopropyl-6'-fluoro-1'H-[1,2'-bibenzo[d]imidazole]-5-carbonitrile (Ex. 6) & 1'-cyclopropyl-6'-fluoro-1'H-[1,2'-bibenzo[d]imidazole]-6-carbonitrile (Ex. 7)

To a stirred solution of 1H-benzo[d]imidazole-5-carbonitrile (111 mg, 0.78 mmol) in DMSO (5 mL) was added potassium carbonate (162 mg, 1.18 mmol) and 2-bromo-1-cyclopropyl-6-fluoro-1H-benzo[d]imidazole Int-1 (100 mg, 0.39 mmol) at room temperature under an inert atmosphere. The reaction mixture was heated to 100° C. and stirred for 16 h. After consumption of starting material (by TLC), the reaction mixture was diluted with ice cold water (25 mL) and extracted with EtOAc (2×25 mL). The combined organic extracts were dried over anhydrous Na₂SO₄ and concentrated under reduced pressure. The crude material was purified by silica gel column chromatography (eluent: 2% MeOH/CH₂Cl₂) followed by preparative HPLC to afford 1'-cyclopropyl-6'-fluoro-1'H-[1,2'-bibenzo[d]imidazole]-5-carbonitrile Ex. 6 (30 mg, 0.09 mmol, 24%) and 1'-cyclopropyl-6'-fluoro-1'H-[1,2'-bibenzo[d]imidazole]-6-carbonitrile Ex. 7 (30 mg, 0.09 mmol, 24%) as off white solids respectively. The two structures were confirmed by 2 D NMR (NOESY, DQFCOSY) studies.

Analytical Data of Ex. 6:

¹H NMR (400 MHz, CD₃OD): δ 8.96 (s, 1H), 8.28 (s, 1H), 7.97 (d, J=8.4 Hz, 1H), 7.80-7.72 (m, 2H), 7.52 (dd, J=8.7, 2.4 Hz, 1H), 7.19 (td, J=9.3, 2.1 Hz, 1H), 3.67-3.60 (m, 1H), 1.07-1.00 (m, 2H), 0.72-0.66 (m, 2H)

LC-MS: m/z 317.9 [M+H]⁺ at 2.35 RT (99.53% purity) HPLC: 98.79%

Analytical Data of Ex. 7:

¹H NMR (400 MHz, CD₃OD): δ 9.03 (s, 1H), 8.29 (s, 1H), 8.00 (d, J=8.4 Hz, 1H), 7.79-7.73 (m, 2H), 7.51 (dd, J=8.7, 2.5 Hz, 1H), 7.18 (td, J=9.3, 2.4 Hz, 1H), 3.69-3.64 (m, 1H), 1.09-1.04 (m, 2H), 0.73-0.68 (m, 2H)

LC-MS: m/z 317.9 [M+H]⁺ at 2.35 RT (98.07% purity) HPLC: 97.16%

Example 8 & Example 9

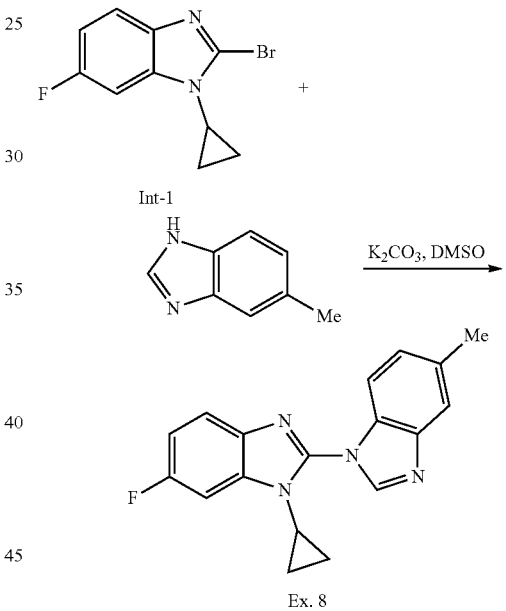

Ex. 8

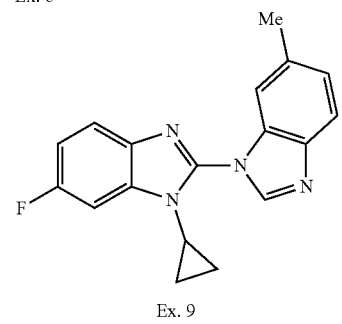

Ex. 9

1'-cyclopropyl-6'-fluoro-5-methyl-1'H-1,2'-bibenzo[d]imidazole (Ex. 8) & 1'-cyclopropyl-6'-fluoro-6-methyl-1'H-1,2'-bibenzo[d]imidazole (Ex. 9)

To a stirred solution of 2-bromo-1-cyclopropyl-6-fluoro-1H-benzo[d]imidazole Int-1 (100 mg, 0.39 mmol) and 5-methyl-1H-benzo[d]imidazole (103 mg, 0.78 mmol) in DMSO (5 mL) was added potassium carbonate (162 mg, 1.18 mmol) and at room temperature under an inert atmosphere. The reaction mixture was heated to 90° C. and stirred for 16 h. After consumption of starting material (by TLC), the reaction mixture was diluted with water (25 mL) and extracted with EtOAc (2×25 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) followed by preparative HPLC to afford 1'-cyclopropyl-6'-fluoro-5-methyl-1'H-1,2'-bibenzo[d]imidazole Ex. 8 (40 mg, 0.13 mmol, 33%) and 1'-cyclopropyl-6'-fluoro-6-methyl-1'H-1,2'-bibenzo[d]imidazole Ex. 9 (40 mg, 0.13 mmol, 33%) as off white solids respectively. The two structures was confirmed by 2 D NMR (NOESY, DQFCOSY).

Analytical Data of Ex. 8:

$^1$H NMR (400 MHz, CD$_3$OD): δ 8.69 (s, 1H), 7.72 (dd, J=8.8, 4.7 Hz, 1H), 7.64-7.60 (m, 2H), 7.50 (dd, J=8.7, 2.4 Hz, 1H), 7.30 (dd, J=8.3, 0.9 Hz, 1H), 7.21-7.13 (m, 1H), 3.64-3.58 (m, 1H), 2.52 (s, 3H), 1.03-0.98 (m, 2H), 0.68-0.63 (m, 2H)

LC-MS: m/z 306.9 [M+H]$^+$ at 2.95 RT (99.99% purity)

HPLC: 99.46%

Analytical Data of Ex. 9:

$^1$H NMR (400 MHz, CD$_3$OD): δ 8.66 (s, 1H), 7.76-7.68 (m, 2H), 7.56-7.49 (m, 2H), 7.28 (dd, J=8.3, 1.1 Hz, 1H), 7.21-7.14 (m, 1H), 3.64-3.58 (m, 1H), 2.50 (s, 3H), 1.05-0.98 (m, 2H), 0.69-0.63 (m, 2H)

LC-MS: m/z 306.9 [M+H]$^+$ at 2.96 RT (99.92% purity)

HPLC: 99.77%

Example 10 & Example 11

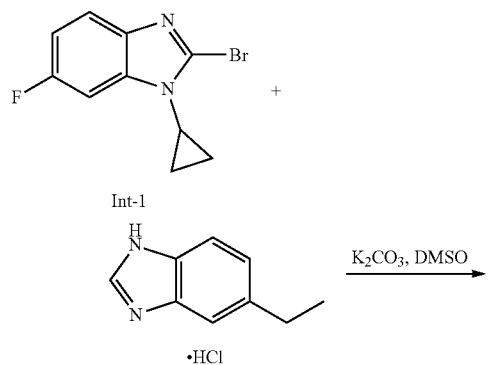

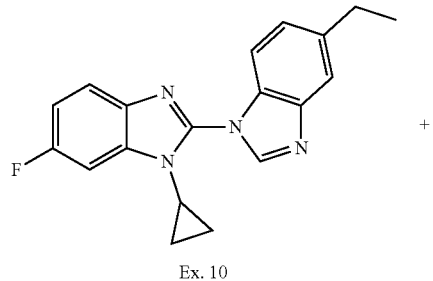

Ex. 10

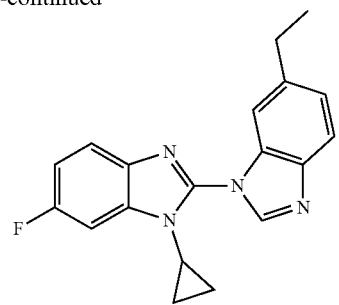

Ex. 11

1'-cyclopropyl-5-ethyl-6'-fluoro-1'H-1,2'-bibenzo[d]imidazole (Ex. 10) & 1'-cyclopropyl-6-ethyl-6'-fluoro-1'H-1,2'-bibenzo[d]imidazole (Ex. 11)

To a stirred solution of 2-bromo-1-cyclopropyl-6-fluoro-1H-benzo[d]imidazole Int-1 (100 mg, 0.39 mmol) in DMSO (5 mL) was added 5-ethyl-1H-benzo[d]imidazole hydrochloride 1 (143 mg, 0.78 mmol) and potassium carbonate (162 mg, 1.18 mmol) at room temperature under an inert atmosphere. The reaction mixture was heated to 90° C. and stirred for 16 h. After consumption of starting material (by TLC), the reaction mixture was diluted with water (25 mL) and extracted with EtOAc (2×25 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) followed by preparative HPLC to afford 1'-cyclopropyl-5-ethyl-6'-fluoro-1'H-1,2'-bibenzo[d]imidazole Ex. 10 (30 mg, 0.09 mmol, 15%) and 1'-cyclopropyl-6-ethyl-6'-fluoro-1'H-1,2'-bibenzo[d]imidazole Ex. 11 (30 mg, 0.09 mmol, 15%) as off white solids respectively. The two structures were confirmed 2 D NMR (NOESY, DQFCOSY).

Analytical Data of Ex. 10:

$^1$H NMR (400 MHz, CD$_3$OD): δ 8.70 (s, 1H), 7.72 (dd, J=8.9, 4.6 Hz, 1H), 7.66-7.63 (m, 2H), 7.50 (dd, J=8.7, 2.3 Hz, 1H), 7.33 (dd, J=8.0, 1.4 Hz, 1H), 7.21-7.13 (m, 1H), 3.64-3.58 (m, 1H), 2.83 (q, J=7.5 Hz, 2H), 1.33 (t, J=7.6 Hz, 3H), 1.04-0.98 (m, 2H), 0.70-0.63 (m, 2H)

LC-MS: m/z 320.9 [M+H]$^+$ at 3.19 RT (99.96% purity)

HPLC: 99.86%

Analytical Data of Ex. 11:

$^1$H NMR (400 MHz, CD$_3$OD): δ 8.68 (s, 1H), 7.74 (t, J=2.3 Hz, 1H), 7.72 (t, J=2.3 Hz, 1H), 7.56 (s, 1H), 7.51 (dd, J=8.7, 2.4 Hz, 1H), 7.32 (dd, J=8.3, 1.3 Hz, 1H), 7.21-7.14 (m, 1H), 3.64-3.58 (m, 1H), 2.80 (q, J=7.7 Hz, 2H), 1.28 (t, J=7.6 Hz, 3H), 1.05-0.98 (m, 2H), 0.70-0.63 (m, 2H)

LC-MS: m/z 321.0 [M+H]$^+$ at 3.16 RT (99.97% purity)

HPLC: 99.83%

Example 12 & Example 13

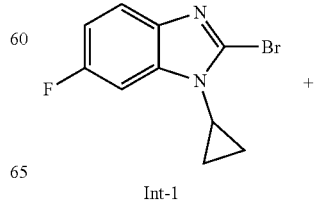

Int-1

-continued

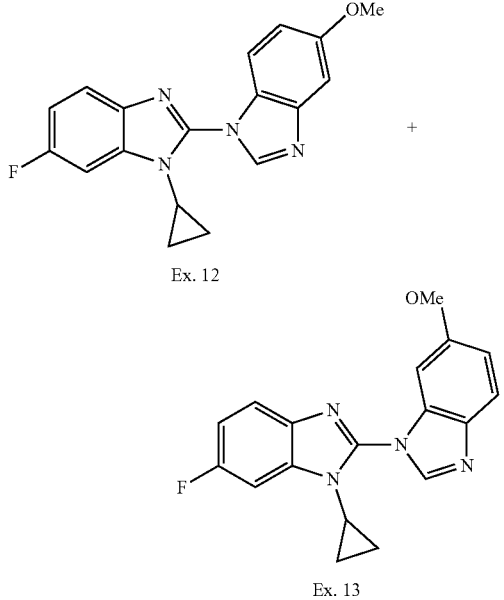

Ex. 12

Ex. 13

1'-cyclopropyl-6'-fluoro-5-methoxy-1'H-1,2'-bibenzo[d]imidazole (Ex. 12) & 1'-cyclopropyl-6'-fluoro-6-methoxy-1'H-1,2'-bibenzo[d]imidazole (Ex. 13) (LNB No: SVC-MA1530-065)

To a stirred solution of 5-methoxy-1H-benzo[d]imidazole (116 mg, 0.78 mmol) in DMSO (2.5 mL) was added potassium carbonate (162 mg, 1.18 mmol) at room temperature under an inert atmosphere and the mixture was stirred for 15 min. 2-Bromo-1-cyclopropyl-6-fluoro-1H-benzo[d]imidazole Int-1 (100 mg, 0.39 mmol) was added at room temperature and the reaction mixture was heated to 100° C. and stirred for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 5% MeOH/$CH_2Cl_2$) followed by preparative HPLC to afford 1'-cyclopropyl-6'-fluoro-5-methoxy-1'H-1,2'-bibenzo[d]imidazole Ex. 12 (20 mg, 0.06 mmol, 15%) and 1'-cyclopropyl-6'-fluoro-6-methoxy-1'H-1,2'-bibenzo[d]imidazole Ex. 13 (40 mg, 0.12 mmol, 30%) as white solids respectively. The two structures were confirmed by 2 D NMR (NOESY, DQFCOSY).

Analytical Data of Ex. 12:
$^1$H NMR (400 MHz, $CD_3OD$): δ 8.69 (s, 1H), 7.71 (dd, J=9.0, 4.6 Hz, 1H), 7.67-7.62 (m, 1H), 7.49 (dd, J=8.8, 2.3 Hz, 1H), 7.33 (d, J=2.4 Hz, 1H), 7.20-7.15 (m, 1H), 7.08 (dd, J=9.0, 2.4 Hz, 1H), 3.90 (s, 3H), 3.64-3.59 (m, 1H), 1.06-1.00 (m, 2H), 0.69-0.64 (m, 2H)

LC-MS: m/z 323.1 [M+H]$^+$ at 2.32 RT (98.58% purity)
HPLC: 98.16%

Analytical Data of Ex. 13:
$^1$H NMR (400 MHz, $CD_3OD$): δ 8.62 (s, 1H), 7.76-7.68 (m, 2H), 7.51 (dd, J=8.7, 2.3 Hz, 1H), 7.24 (d, J=2.3 Hz, 1H), 7.21-7.14 (m, 1H), 7.06 (dd, J=8.9, 2.4 Hz, 1H), 3.84 (s, 3H), 3.64-3.59 (m, 1H), 1.06-1.00 (m, 2H), 0.70-0.65 (m, 2H)

LC-MS: m/z 323.0 [M+H]$^+$ at 2.29 RT (98.70% purity)
HPLC: 99.58%

Example 14

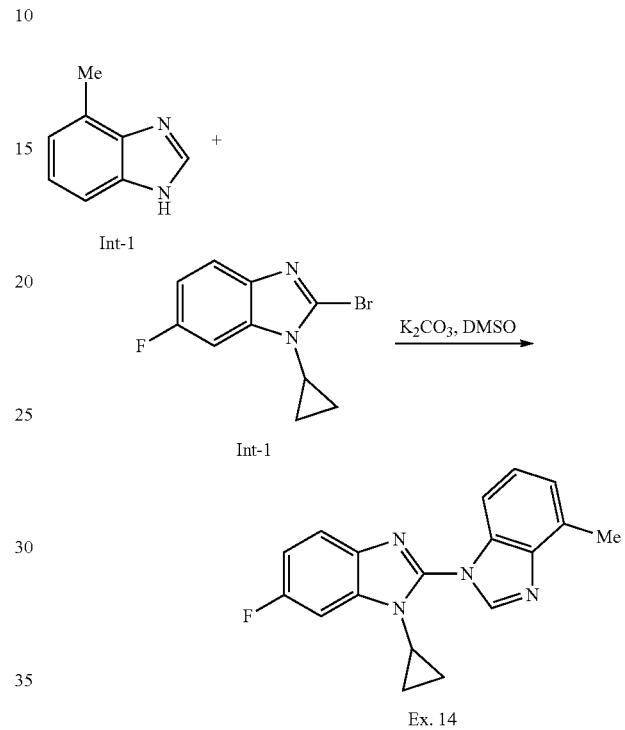

Ex. 14

1'-cyclopropyl-6'-fluoro-4-methyl-1'H-1,2'-bibenzo[d]imidazole (Ex. 14)

To a stirred solution of 2-bromo-1-cyclopropyl-6-fluoro-1H-benzo[d]imidazole Int-1 (120 mg, 0.47 mmol) and 4-methyl-1H-benzo[d]imidazole Int-3 (74 mg, 0.56 mmol) in DMSO (5 mL) was added potassium carbonate (195 mg, 1.41 mmol) at room temperature under an inert atmosphere. The reaction mixture was heated to 110° C. and stirred for 16 h. After consumption of starting material (by TLC), the reaction mixture was diluted with water (20 mL) and extracted with EtOAc (2×20 mL). The combined organic extracts were dried over anhydrous $Na_2SO_4$ and concentrated under reduced pressure. The crude material was purified by silica gel column chromatography (eluent: 50% EtOAc/hexane) to afford 1'-cyclopropyl-6'-fluoro-4-methyl-1'H-1,2'-bibenzo[d]imidazole Ex. 14 (60 mg, 0.2 mmol, 41%) as a pale yellow solid. The structure was confirmed by 2 D NMR (NOESY, DQFCOSY).

$^1$H NMR (500 MHz, $CD_3OD$): δ 8.70 (s, 1H), 7.72 (dd, J=8.7, 4.8 Hz, 1H), 7.56-7.48 (m, 2H), 7.33 (t, J=7.8 Hz, 1H), 7.24 (d, J=7.3 Hz, 1H), 7.17 (td, J=9.3, 2.5 Hz, 1H), 3.64-3.57 (m, 1H), 2.70 (s, 3H), 1.02-0.95 (m, 2H), 0.67-0.62 (m, 2H)

LC-MS: m/z 306.9 [M+H]$^+$ at 2.71 RT (98.35% purity)
HPLC: 98.43%

Example 15

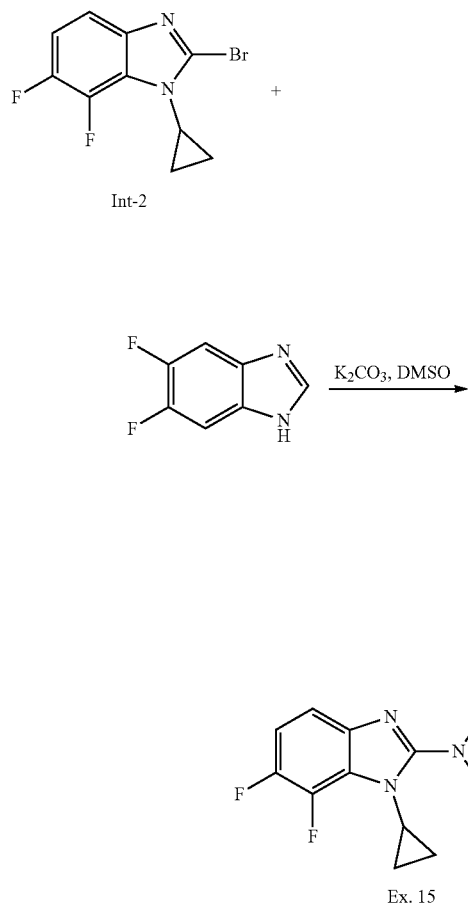

1'-cyclopropyl-5,6,6',7'-tetrafluoro-1'H-1,2'-bibenzo[d]imidazole (Ex. 15)

To a stirred solution of 2-bromo-1-cyclopropyl-6,7-difluoro-1H-benzo[d]imidazole Int-2 (60 mg, 0.22 mmol) and 5,6-difluoro-1H-benzo[d]imidazole (41 mg, 0.26 mmol) in DMSO (2 mL) was added potassium carbonate (91 mg, 0.66 mmol) at room temperature under an inert atmosphere. The reaction mixture was heated to 80° C. and stirred for 16 h. After consumption of starting material (by TLC), the reaction mixture was diluted with water (15 mL) and extracted with EtOAc (2×15 mL). The combined organic extracts were dried over anhydrous Na$_2$SO$_4$ and concentrated under reduced pressure. The crude material was purified by silica gel column chromatography (eluent: 40% EtOAc/hexane) to afford 1'-cyclopropyl-5,6,6',7'-tetrafluoro-1'H-1,2'-bibenzo[d]imidazole Ex. 15 (20 mg, 0.06 mmol, 26%) as a pale yellow solid.

$^1$H NMR (400 MHz, CD$_3$OD): δ 8.84 (s, 1H), 7.83 (dd, J=10.0, 7.1 Hz, 1H), 7.73 (dd, J=10.3, 7.2 Hz, 1H), 7.55-7.49 (m, 1H), 7.33-7.24 (m, 1H), 3.87-3.80 (m, 1H), 1.09-1.02 (m, 2H), 0.80-0.73 (m, 2H)

LC-MS: m/z 347.0 [M+H]$^+$ at 2.65 RT (98.94% purity)
HPLC: 95.27%

Example 16

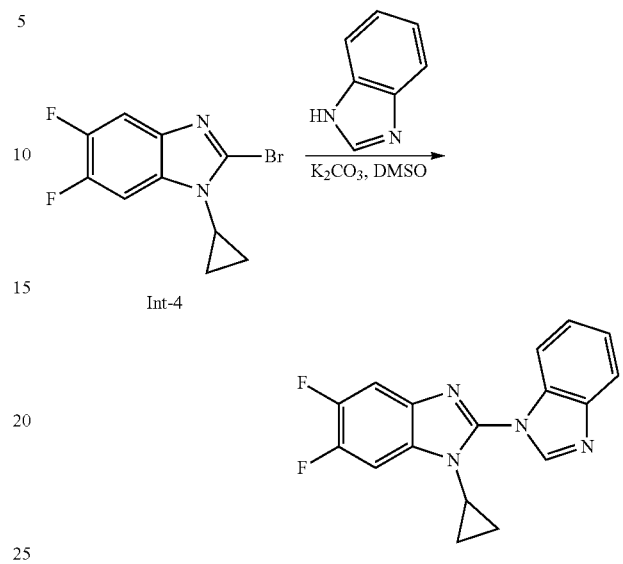

1'-cyclopropyl-5',6'-difluoro-1'H-1,2'-bibenzo[d]imidazole (Ex. 16)

To a stirred solution of 2-bromo-1-cyclopropyl-5,6-difluoro-1H-benzo[d]imidazole Int-4 (100 mg, 0.36 mmol) in DMSO (5 mL) was added potassium carbonate (152 mg, 1.09 mmol) and 1H-benzo[d]imidazole (86.5 mg, 0.73 mmol) at room temperature under an inert atmosphere. The reaction mixture was stirred at 100° C. for 16 h. After consumption of starting material (by TLC), the reaction mixture was diluted with water (15 mL) and extracted with EtOAc (2×20 mL). The combined organic extracts were dried over anhydrous Na$_2$SO$_4$ and concentrated under reduced pressure. The crude material was purified by silica gel column chromatography (eluent: 30% EtOAc/hexane) to afford 1'-cyclopropyl-5',6'-difluoro-1'H-1,2'-bibenzo[d]imidazole Ex. 16 (80 mg, 0.25 mmol, 70%) as a white solid.

$^1$H NMR (400 MHz, DMSO-d$_6$): δ 8.91 (s, 1H), 7.95-7.70 (m, 4H), 7.47-7.30 (m, 2H), 3.75-3.69 (m, 1H), 1.07-0.91 (m, 2H), 0.69-0.58 (m, 2H)

LC-MS: m/z 310.9 [M+H]$^+$ at 2.89 RT (99.83% purity)
HPLC: 98.92%

Example 17

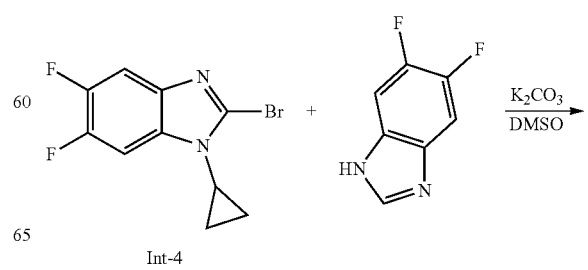

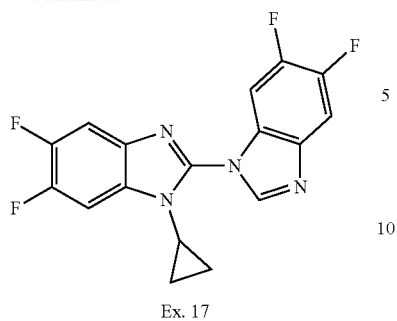

Ex. 17

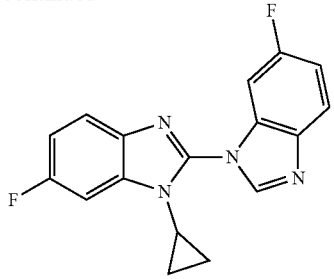

Ex. 19

1'-cyclopropyl-5,5',6,6'-tetrafluoro-1'H-1,2'-bibenzo[d]imidazole (Ex. 17)

To a stirred solution of 2-bromo-1-cyclopropyl-5,6-difluoro-1H-benzo[d]imidazole Int-4 (100 mg, 0.36 mmol) in DMSO (5 mL) was added 5,6-difluoro-1H-benzo[d]imidazole (113 mg, 0.73 mmol) and potassium carbonate (152 mg, 1.09 mmol) at room temperature under an inert atmosphere. The reaction mixture was stirred at 100° C. for 16 h. After consumption of starting material (by TLC), the reaction mixture was diluted with ice cold water (30 mL) and extracted with EtOAc (2×30 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) to afford 1'-cyclopropyl-5,5',6,6'-tetrafluoro-1'H-1,2'-bibenzo[d]imidazole Ex. 17 (80 mg, 0.23 mmol, 63%) as an off white solid.

$^1$H NMR (400 MHz, DMSO-d$_6$): δ 8.98 (s, 1H), 8.00-7.90 (m, 2H), 7.90-7.82 (m, 2H), 3.72-3.70 (m, 1H), 1.04-0.95 (m, 2H), 0.73-0.59 (m, 2H)

LC-MS: m/z 347.0 [M+H]$^+$ at 3.22 RT (98.67% purity)

HPLC: 95.00%

Example 18 & Example 19

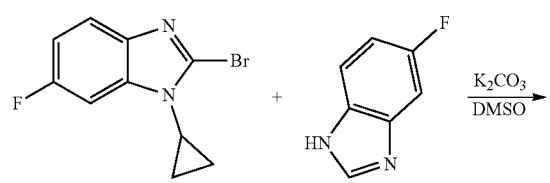

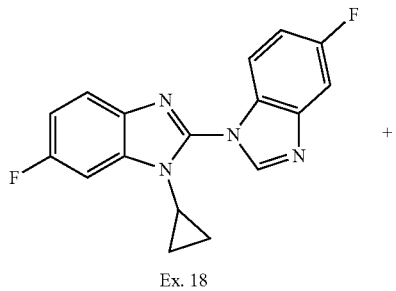

Ex. 18

1'-cyclopropyl-5,6'-difluoro-1'H-1,2'-bibenzo[d]imidazole (Ex. 18) & 1'-cyclopropyl-6,6'-difluoro-1'H-1,2'-bibenzo[d]imidazole (Ex. 19)

To a stirred solution of 2-bromo-1-cyclopropyl-6-fluoro-1H-benzo[d]imidazole Int-1 (150 mg, 0.59 mmol) in DMSO (5 mL) was added 5-fluoro-1H-benzo[d]imidazole (160 mg, 1.17 mmol) and potassium carbonate (244 mg, 1.76 mmol) at room temperature under an inert atmosphere. The reaction mixture was stirred at 100° C. for 16 h. After consumption of starting material (by TLC), the reaction mixture was diluted with ice cold water (30 mL) and extracted with EtOAc (2×30 mL). The combined organic extracts were dried over anhydrous Na$_2$SO$_4$ and concentrated under reduced pressure. The crude material was purified by silica gel column chromatography (eluent: 3% MeOH/CH$_2$Cl$_2$) followed by preparative HPLC to afford 1'-cyclopropyl-5,6'-difluoro-1'H-1,2'-bibenzo[d]imidazole Ex. 18 (60 mg, 0.19 mmol, 33%) and 1'-cyclopropyl-6,6'-difluoro-1'H-1,2'-bibenzo[d]imidazole Ex. 19 (40 mg, 0.13 mmol, 22%) as off white solids respectively. The two structures were confirmed by 2 D NMR (NOESY, COSY).

Analytical Data for Ex. 18

$^1$H NMR (400 MHz, DMSO-d$_6$): δ 8.98 (s, 1H), 7.88 (dd, J=8.9, 4.8 Hz, 1H), 7.77 (dd, J=8.8, 4.9 Hz, 1H), 7.67 (dd, J=9.4, 2.4 Hz, 1H), 7.56 (dd, J=9.0, 2.4 Hz, 1H), 7.30-7.25 (m, 1H), 7.23-7.17 (m, 1H), 3.73-3.68 (m, 1H), 1.09-0.91 (m, 2H), 0.72-0.51 (m, 2H)

LC-MS: m/z 310.9 [M+H]$^+$ at 2.91 RT (99.79% purity)

HPLC: 99.67%

Analytical Data for Ex. 19

$^1$H NMR (400 MHz, DMSO-d$_6$): δ 8.98 (s, 1H), 7.84 (dd, J=8.9, 4.8 Hz, 1H), 7.77 (dd, J=8.8, 4.9 Hz, 1H), 7.67 (dd, J=9.4, 2.4 Hz, 1H), 7.56 (dd, J=9.0, 2.4 Hz, 1H), 7.28-7.15 (m, 2H), 3.73-3.67 (m, 1H), 1.05-0.99 (m, 2H), 0.67-0.62 (m, 2H)

LC-MS: m/z 310.9 [M+H]$^+$ at 2.93 RT (99.87% purity)

HPLC: 99.58%

Example 20 & Example 21

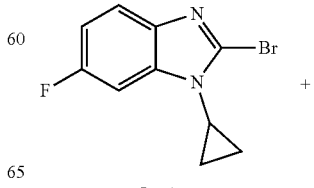

Int-1

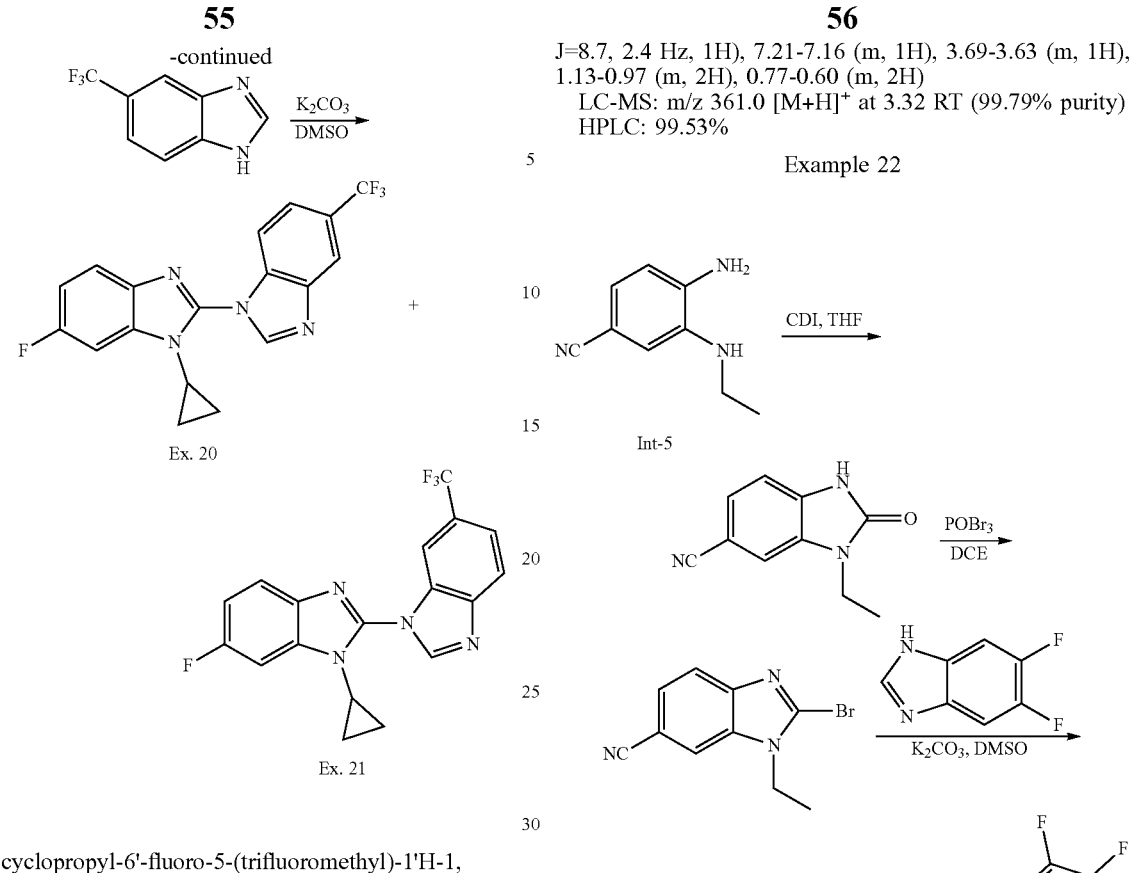

Ex. 20

Ex. 21

1'-cyclopropyl-6'-fluoro-5-(trifluoromethyl)-1'H-1, 2'-bibenzo[d]imidazole (Ex. 20) & 1'-cyclopropyl-6'-fluoro-6-(trifluoromethyl)-1'H-1,2'-bibenzo[d] imidazole (Ex. 21)

To a stirred solution of 2-bromo-1-cyclopropyl-6-fluoro-1H-benzo[d]imidazole Int-1 (150 mg, 0.60 mmol) in DMSO (5 mL) was added 5-(trifluoromethyl)-1H-benzo[d]imidazole (131 mg, 0.70 mmol) and potassium carbonate (243 mg, 1.76 mmol) at room temperature under an inert atmosphere. The reaction mixture was stirred at 90° C. for 16 h. After consumption of starting material (by TLC), the reaction mixture was diluted with ice cold water (50 mL) and extracted with EtOAc (2×50 mL). The combined organic extracts were washed with water (50 mL), brine (50 mL), dried over anhydrous Na$_2$SO$_4$ and concentrated under reduced pressure. The crude material was purified by silica gel column chromatography (eluent: 30% EtOAc/hexane) followed by preparative HPLC to afford 1'-cyclopropyl-6'-fluoro-5-(trifluoromethyl)-1'H-1,2'-bibenzo[d]imidazole B-397 (40 mg, 0.11 mmol, 38%) and 1'-cyclopropyl-6'-fluoro-6-(trifluoromethyl)-1'H-1,2'-bibenzo[d]imidazole B-421 (40 mg, 0.11 mmol, 38%) as off white solids respectively. The two structures were confirmed by 2 D NMR studies (NOESY, DQFCOSY).

Analytical Data for Ex. 20:

$^1$H NMR (400 MHz, CD$_3$OD): δ 8.91 (s, 1H), 8.15 (s, 1H), 7.97 (d, J=8.5 Hz, 1H), 7.77-7.70 (m, 2H), 7.52 (dd, J=8.7, 2.4 Hz, 1H), 7.21-7.16 (m, 1H), 3.67-3.60 (m, 1H), 1.07-1.00 (m, 2H), 0.70-0.65 (m, 2H)

LC-MS: m/z 360.9 [M+H]$^+$ at 3.34 RT (99.60% purity)

HPLC: 99.64%

Analytical Data for Ex. 21:

$^1$H NMR (400 MHz, CD$_3$OD): δ 9.01 (s, 1H), 8.19 (s, 1H), 8.02 (d, J=8.5 Hz, 1H), 7.80-7.71 (m, 2H), 7.52 (dd, J=8.7, 2.4 Hz, 1H), 7.21-7.16 (m, 1H), 3.69-3.63 (m, 1H), 1.13-0.97 (m, 2H), 0.77-0.60 (m, 2H)

LC-MS: m/z 361.0 [M+H]$^+$ at 3.32 RT (99.79% purity)

HPLC: 99.53%

Example 22

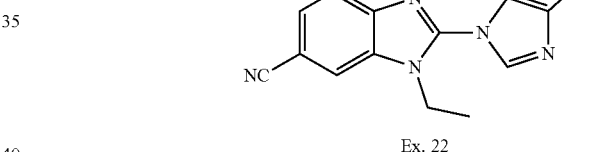

Int-5

Ex. 22

3-ethyl-2-oxo-2,3-dihydro-1H-benzo[d]imidazole-5-carbonitrile

To a stirred solution of 4-amino-3-(ethylamino)benzonitrile Int-5 (500 mg, 3.10 mmol) in THF (10 mL) was added 1,1'-carbonyldiimidazole (750 mg, 4.05 mmol) at 0° C. under an inert atmosphere. The reaction mixture was gradually warmed to room temperature and stirred for 16 h. After consumption of starting material (by TLC), the reaction mixture was diluted with water (20 mL) and extracted with EtOAc (2×20 mL). The combined organic extracts were washed with water (20 mL), dried over anhydrous Na$_2$SO$_4$ and concentrated under reduced pressure. The crude material was purified by silica gel column chromatography (eluent: 50-60% EtOAc/hexane) to afford 3-ethyl-2-oxo-2, 3-dihydro-1H-benzo[d]imidazole-5-carbonitrile (280 mg, 1.49 mmol, 50%) as an off-white solid.

$^1$H NMR (400 MHz, DMSO-d$_6$): δ 11.39 (brs, 1H), 7.69 (s, 1H), 7.44 (dd, J=8.0, 1.5 Hz, 1H), 7.12 (d, J=8.2 Hz, 1H), 3.88-3.82 (m, 2H), 1.19 (t, J=7.2 Hz, 3H)

LC-MS: m/z 188.1 [M+H]$^+$ at 2.87 RT (99.10% purity)

2-bromo-1-ethyl-1H-benzo[d]imidazole-6-carbonitrile

To a stirred solution of phosphoryl bromide (153 mg, 0.53 mmol) in 1,2-dichloroethane (5 mL) was added 3-ethyl-2- oxo-2,3-dihydro-1H-benzo[d]imidazole-5-carbonitrile (50 mg, 0.26 mmol) at room temperature under an inert atmosphere. The reaction mixture was heated to reflux temperature and stirred for 36 h. After consumption of starting material (by TLC), the reaction mixture was diluted with ice cold water (20 mL), neutralized using saturated sodium carbonate solution to pH~7 and extracted with EtOAc (2×20 mL). The combined organic extracts were washed with water (20 mL), dried over anhydrous $Na_2SO_4$ and concentrated under reduced pressure to obtain 2-bromo-1-ethyl-1H-benzo[d]imidazole-6-carbonitrile (65 mg) as an off-white solid. The crude material was taken to the next step without further purification.

LC-MS: m/z 250.2 [M+H]$^+$ at 3.55 RT (50.03% purity)

1'-ethyl-5,6-difluoro-1'H-[1,2'-bibenzo[d]imidazole]-6'-carbonitrile (Ex. 22)

To a stirred solution of 2-bromo-1-ethyl-1H-benzo[d]imidazole-6-carbonitrile (65 mg, crude) in DMSO (2 mL) was added 5,6-difluoro-1H-benzo[d]imidazole (48 mg, 0.31 mmol) and potassium carbonate (107 mg, 0.78 mmol) at room temperature under an inert atmosphere. The reaction mixture was heated to 80° C. and stirred for 6 h. After consumption of starting material (by TLC), the reaction mixture was diluted with ice cold water (20 mL) and extracted with EtOAc (2×20 mL). The combined organic extracts were washed with water (20 mL), brine (20 mL), dried over anhydrous $Na_2SO_4$ and concentrated under reduced pressure. The crude material was purified by silica gel column chromatography (eluent: 50-60% EtOAc/hexane) which was further triturated with $CH_3CN$ (2×20 mL) to afford 1'-ethyl-5,6-difluoro-1'H-[1,2'-bibenzo[d]imidazole]-6'-carbonitrile Ex. 22 (15 mg, 0.04 mmol, 18%) as an off-white solid.

$^1$H NMR (400 MHz, $CD_3OD$): δ 8.70 (s, 1H), 8.26 (s, 1H), 7.93 (d, J=8.0 Hz, 1H), 7.80-7.70 (m, 2H), 7.66 (dd, J=9.9, 7.0 Hz, 1H), 4.37-4.31 (m, 2H), 1.37 (t, J=7.3 Hz, 3H)

LC-MS: m/z 323.9 [M+H]$^+$ at 2.83 RT (97.05% purity)
HPLC: 99.02%

Example 23 & Example 24

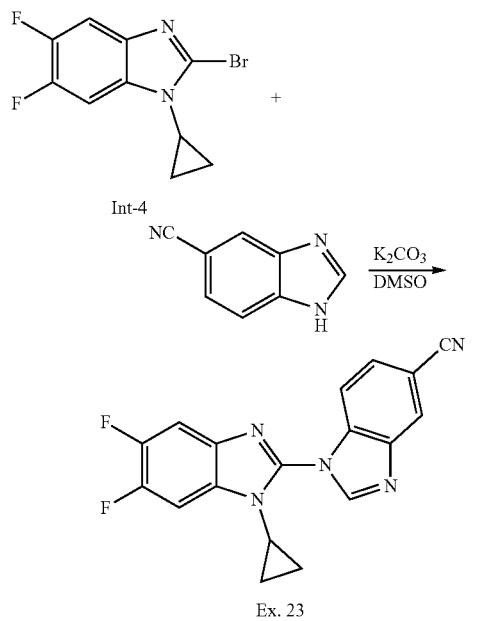

Ex. 23

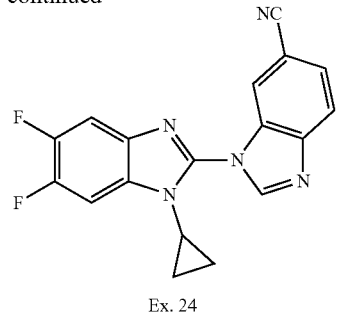

Ex. 24

1'-cyclopropyl-5',6'-difluoro-1'H-[1,2'-bibenzo[d]imidazole]-5-carbonitrile (Ex. 23) & 1'-cyclopropyl-5',6'-difluoro-1'H-[1,2'-bibenzo[d]imidazole]-6-carbonitrile (Ex. 24)

To a stirred solution of 2-bromo-1-cyclopropyl-5,6-difluoro-1H-benzo[d]imidazole Int-4 (125 mg, 0.45 mmol) in DMSO (4 mL) was added 1H-benzo[d]imidazole-5-carbonitrile (98 mg, 0.68 mmol) and potassium carbonate (190 mg, 1.37 mmol) at room temperature under an inert atmosphere. The reaction mixture was heated to 90° C. and stirred for 16 h. After consumption of starting material (by TLC), the reaction mixture was diluted with ice cold water (50 mL) and extracted with EtOAc (2×50 mL). The combined organic extracts were washed with water (50 mL), brine (50 mL), dried over anhydrous $Na_2SO_4$ and concentrated under reduced pressure. The crude material was purified by silica gel column chromatography (eluent: 2% $MeOH/CH_2Cl_2$) followed by preparative HPLC to afford 1'-cyclopropyl-5',6'-difluoro-1'H-[1,2'-bibenzo[d]imidazole]-5-carbonitrile Ex. 23 (40 mg, 0.12 mmol, 26%) and 1'-cyclopropyl-5',6'-difluoro-1'H-[1,2'-bibenzo[d]imidazole]-6-carbonitrile Ex. 24 (40 mg, 0.12 mmol, 26%) as off white solids respectively. The two structures were confirmed by 2 D NMR studies (NOESY, DQFCOSY).

Analytical Data for Ex. 23:
$^1$H NMR (400 MHz, DMSO-$d_6$): δ 9.14 (s, 1H), 8.44 (s, 1H), 8.06 (d, J=8.41 Hz, 1H), 7.93-7.81 (m, 3H), 3.74-3.69 (m, 1H), 1.10-0.96 (m, 2H), 0.75-0.61 (m, 2H)

LC-MS: m/z 336.0 [M+H]$^+$ at 2.93 RT (98.56% purity)
HPLC: 98.26%

Analytical Data for Ex. 24:
$^1$H NMR (400 MHz, DMSO-$d_6$): δ 9.17 (s, 1H), 8.40 (s, 1H), 8.04 (d, J=8.3 Hz, 1H), 7.92 (dd, J=10.9, 7.4 Hz, 1H), 7.87 (dd, J=10.4, 7.3 Hz, 1H), 7.81 (dd, J=8.3, 1.6 Hz, 1H), 3.81-3.68 (m, 1H), 1.09-0.93 (m, 2H), 0.74-0.62 (m, 2H)

LC-MS: m/z 335.9 [M+H]$^+$ at 2.94 RT (96.57% purity)
HPLC: 97.57%

Example 25

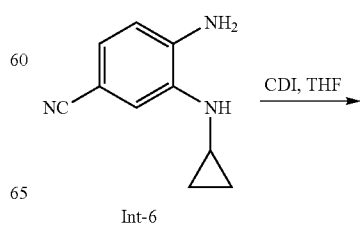

Int-6

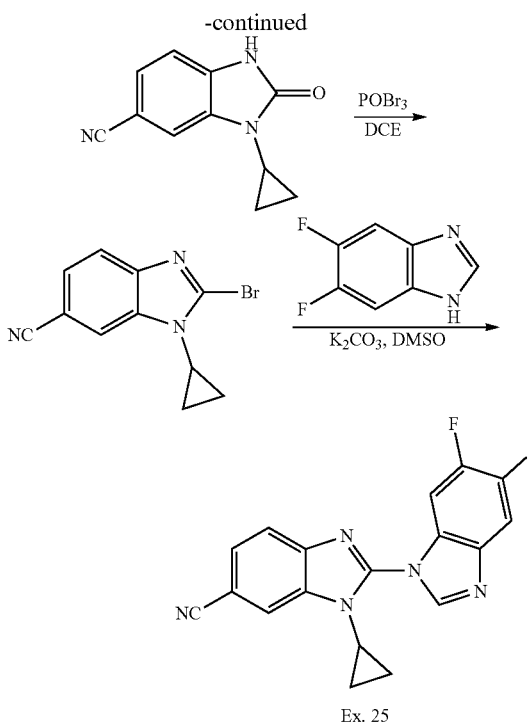

Ex. 25

3-cyclopropyl-2-oxo-2,3-dihydro-1H-benzo[d]imidazole-5-carbonitrile

To a stirred solution of 4-amino-3-(cyclopropylamino) benzonitrile Int-6 (500 mg, 2.89 mmol) in THF (10 mL) was added 1,1'-carbonyldiimidazole (702 mg, 4.33 mmol) at room temperature under an inert atmosphere. The reaction mixture was gradually warmed to room temperature and stirred for 16 h. After consumption of starting material (by TLC), the reaction mixture was diluted with water (20 mL) and extracted with EtOAc (2×20 mL). The combined organic extracts were washed with water (20 mL), dried over anhydrous $Na_2SO_4$ and concentrated under reduced pressure. The crude material was purified by silica gel column chromatography (eluent: 30-40% EtOAc/hexane) to afford 3-cyclopropyl-2-oxo-2,3-dihydro-1H-benzo[d]imidazole-5-carbonitrile (200 mg, 1.00 mmol, 35%) as an off-white solid.

$^1$H NMR (500 MHz, DMSO-$d_6$): δ 11.29 (brs, 1H), 7.55 (s, 1H), 7.45 (dd, J=8.0, 1.3 Hz, 1H), 7.09 (d, J=8.1 Hz, 1H), 2.91-2.85 (m, 1H), 1.05-1.00 (m, 2H), 0.92-0.83 (m, 2H)

2-bromo-1-cyclopropyl-1H-benzo[d]imidazole-6-carbonitrile

To a stirred solution of 3-cyclopropyl-2-oxo-2,3-dihydro-1H-benzo[d]imidazole-5-carbonitrile (200 mg, 1.0 mmol) in 1,2-dichloroethane (4 mL) was added phosphoryl bromide (1.2 g, 4.02 mmol) at room temperature under an inert atmosphere. The reaction mixture was heated to 80° C. and stirred for 16 h. After consumption of starting material (by TLC), the reaction mixture was diluted with water (20 mL), basified using saturated sodium carbonate solution (30 mL) and extracted with $CH_2Cl_2$ (2×30 mL). The combined organic extracts were dried over anhydrous $Na_2SO_4$ and concentrated under reduced pressure to afford 2-bromo-1-cyclopropyl-1H-benzo[d]imidazole-6-carbonitrile (50 mg) as a white solid. The crude material was taken to the next step without further purification.

LC-MS: m/z 261.8 [M-F]$^+$ at 2.52 RT (96.21% purity)

1'-cyclopropyl-5,6-difluoro-1'H-[1,2'-bibenzo[d]imidazole]-6'-carbonitrile (Ex. 25)

To a stirred solution of 2-bromo-1-cyclopropyl-1H-benzo[d]imidazole-6-carbonitrile (100 mg, 0.38 mmol) in DMSO (3 mL) was added potassium carbonate (106 mg, 0.76 mmol) and 5,6-difluoro-1H-benzo[d]imidazole (59 mg, 0.38 mmol) at room temperature under an inert atmosphere. The reaction mixture was heated to 80° C. and stirred for 16 h. After consumption of starting material (by TLC), the reaction mixture was diluted with water (20 mL) and extracted with EtOAc (2×20 mL). The combined organic extracts were washed with water (30 mL), dried over anhydrous $Na_2SO_4$ and concentrated under reduced pressure. The crude material was purified by silica gel column chromatography (eluent: 30-40% EtOAc/hexane) to afford 1'-cyclopropyl-5,6-difluoro-1'H-[1,2'-bibenzo[d]imidazole]-6'-carbonitrile Ex. 25 (20 mg, 0.06 mmol, 16%) as an off-white solid.

$^1$H NMR (400 MHz, CD$_3$OD): δ 8.94 (s, 1H), 8.21 (s, 1H), 7.96-7.89 (m, 2H), 7.75 (dd, J=10.2, 7.2 Hz, 1H), 7.71 (dd, J=8.4, 1.5 Hz, 1H), 3.79-3.73 (m, 1H), 1.23-1.14 (m, 2H), 0.84-0.71 (m, 2H)

LC-MS: m/z 336.0 [M+H]$^+$ at 2.96 RT (97.43% purity)
HPLC: 98.95%

Example 26

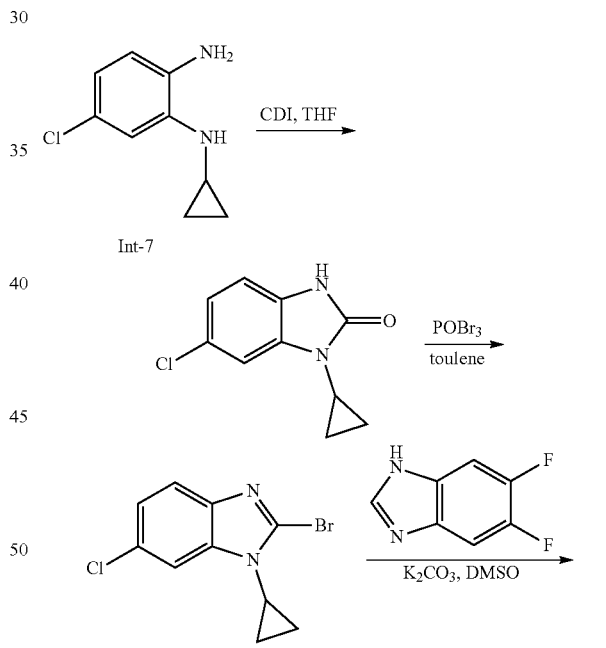

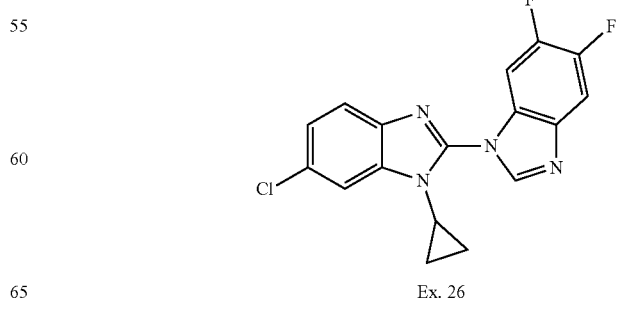

Ex. 26

6-chloro-1-cyclopropyl-1,3-dihydro-2H-benzo[d]imidazol-2-one

To a stirred solution of 5-chloro-N$^1$-cyclopropylbenzene-1,2-diamine Int-7 (200 mg, 1.09 mmol) in THF (10 mL) was added 1,1'-carbonyldiimidazole (267 mg, 1.65 mmol) at room temperature under an inert atmosphere and the mixture was stirred for 16 h. After consumption of starting material (by TLC), the reaction mixture was acidified with 1 N HCl solution (20 mL) and extracted with EtOAc (2×20 mL). The combined organic extracts were dried over anhydrous Na$_2$SO$_4$ and concentrated under reduced pressure to obtain 6-chloro-1-cyclopropyl-1,3-dihydro-2H-benz[d]imidazol-2-one (150 mg) as a brown solid. The crude material was taken to the next step without further purification.

$^1$H NMR (400 MHz, DMSO-d$_6$): δ 7.15 (s, 1H), 7.04-6.99 (m, 1H), 6.96-6.88 (m, 1H), 2.87-2.78 (m, 1H), 1.06-0.96 (m, 2H), 0.88-0.74 (m, 2H)

2-bromo-6-chloro-1-cyclopropyl-1H-benzo[d]imidazole

To a stirred solution of 6-chloro-1-cyclopropyl-1,3-dihydro-2H-benzo[d]imidazol-2-one (150 mg, crude) in toluene (10 mL) was added phosphoryl bromide (825 mg, 2.88) at room temperature under an inert atmosphere. The reaction mixture was heated to 80° C. and stirred for 16 h. After consumption of starting material (by TLC), the reaction mixture was diluted with CH$_2$Cl$_2$ (20 mL), warm water (20 mL) was added and the mixture was stirred for 30 min. The reaction mixture was basified using aqueous Na$_2$CO$_3$ solution to pH~10 and extracted with CH$_2$Cl$_2$ (2×20 mL). The combined organic extracts were washed with water (20 mL), dried over anhydrous Na$_2$SO$_4$ and concentrated under reduced pressure. The crude material was purified by silica gel column chromatography (eluent: 10% EtOAc/hexane) to afford 2-bromo-6-chloro-1-cyclopropyl-1H-benzo[d]imidazole (80 mg, 0.30 mmol, 41%) as an off-white solid.

$^1$H NMR (400 MHz, DMSO-d$_6$): δ 7.63 (s, 1H), 7.58 (d, J=8.7 Hz, 1H), 7.24 (dd, J=8.6, 2.1 Hz, 1H), 3.36-3.30 (m, 1H), 1.27-1.18 (m, 2H), 1.10-1.02 (m, 2H)

6'-chloro-1'-cyclopropyl-5,6-difluoro-1'H-1,2'-bibenzo[d]imidazole (Ex. 26)

To a stirred solution of 2-bromo-6-chloro-1-cyclopropyl-1H-benzo[d]imidazole (80 mg, 0.30 mmol) in DMSO (5 mL) was added potassium carbonate (123 mg, 0.88 mmol) and 5,6-difluoro-1H-benzo[d]imidazole (92 mg, 0.59 mmol) at room temperature under an inert atmosphere. The reaction mixture was heated to 80° C. and stirred for 16 h. After consumption of starting material (by TLC), the reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 6'-chloro-1'-cyclopropyl-5,6-difluoro-1'H-1,2'-bibenzo[d]imidazole Ex. 26 (30 mg, 0.08 mmol, 29%) as an off white solid.

$^1$H NMR (400 MHz, DMSO-d$_6$): δ 8.99 (s, 1H), 7.98-7.96 (m, 2H), 7.79 (s, 1H), 7.77 (d, J=7.0 Hz, 1H), 7.40-7.34 (m, 1H), 3.74-3.68 (m, 1H), 1.08-0.99 (m, 2H), 0.72-0.62 (m, 2H)

LC-MS: m/z 344.9 [M+H]$^+$ at 2.71 RT (96.05% purity)
HPLC: 93.47%

Example 27 & Example 28

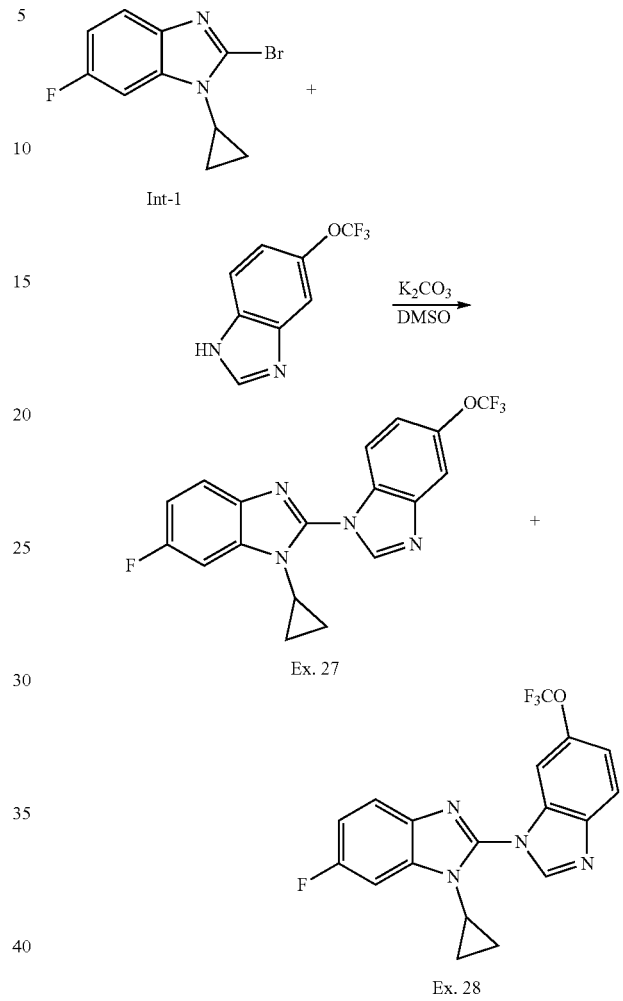

1'-cyclopropyl-6'-fluoro-5-(trifluoromethoxy)-1'H-1,2'-bibenzo[d]imidazole (Ex. 27) & 1'-cyclopropyl-6'-fluoro-6-(trifluoromethoxy)-1'H-1,2'-bibenzo[d]imidazole (Ex. 28)

To a stirred solution of 2-bromo-1-cyclopropyl-6-fluoro-1H-benzo[d]imidazole Int-1 (100 mg, 0.39 mmol) in DMSO (4 mL) was added 5-(trifluoromethoxy)-1H-benzo[d]imidazole (80 mg, 0.40 mmol) and potassium carbonate (108 mg, 0.78 mmol) at room temperature under an inert atmosphere. The reaction mixture was heated to 80° C. and stirred for 24 h. After consumption of starting material (by TLC), the reaction mixture was diluted with ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 20-30% EtOAc/hexane) to afford 1'-cyclopropyl-6'-fluoro-5-(trifluoromethoxy)-1'H-1,2'-bibenzo[d]imidazole Ex. 27 (20 mg, 0.05 mmol, 14%) & 1'-cyclopropyl-6'-fluoro-6-(trifluoromethoxy)-1'H-1,2'-bibenzo[d]imidazole Ex. 28 (20 mg, 0.05 mmol, 14%) as off-white solids respectively. The two structures were confirmed by 2 D NMR (NOESY, DQFCOSY).

Analytical Data of Ex. 27:
$^1$H NMR (400 MHz, CD$_3$OD): δ 8.88 (s, 1H), 7.87 (d, J=8.9 Hz, 1H), 7.78-7.68 (m, 2H), 7.51 (dd, J=8.7, 2.3 Hz, 1H), 7.40 (dd, J=8.9, 1.4 Hz, 1H), 7.19-7.17 (m, 1H), 3.66-3.61 (m, 1H), 1.07-1.00 (m, 2H), 0.71-0.63 (m, 2H)

LC-MS: m/z 377.0 [M+H]$^+$ at 3.36 RT (96.14% purity)
HPLC: 92.27%

Analytical Data of Ex. 28:
$^1$H NMR (400 MHz, CD$_3$OD): δ 8.89 (s, 1H), 7.92 (d, J=8.8 Hz, 1H), 7.81-7.77 (m, 1H), 7.75 (dd, J=8.9, 4.6 Hz, 1H), 7.51 (dd, J=8.7, 2.4 Hz, 1H), 7.41-7.37 (m, 1H), 7.21-7.14 (m, 1H), 3.68-3.61 (m, 1H), 1.08-1.04 (m, 2H), 0.74-0.68 (m, 2H)

LC-MS: m/z 377.0 [M+H]$^+$ at 3.34 RT (98.88% purity)
HPLC: 96.61%

Example 29

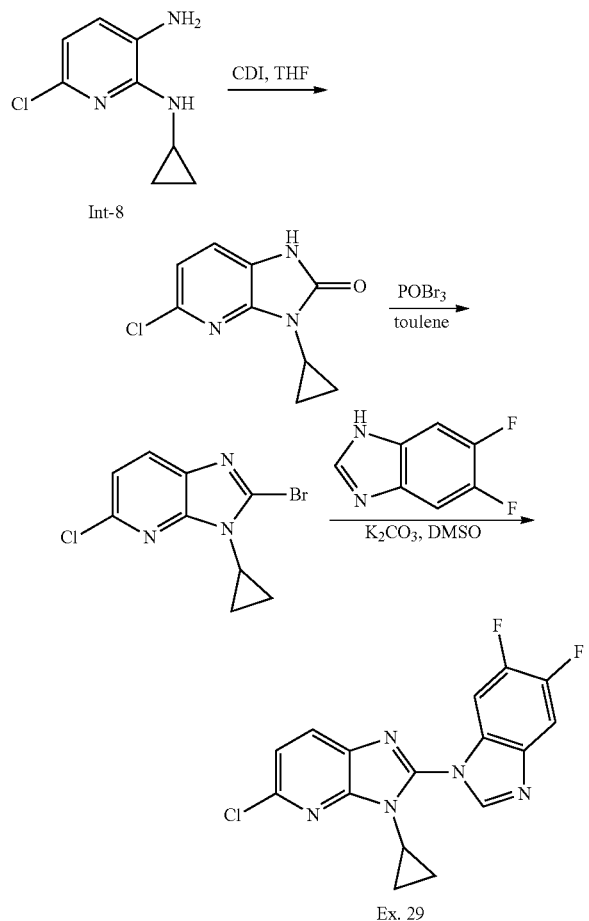

5-chloro-3-cyclopropyl-1,3-dihydro-2H-imidazo[4,5-b]pyridin-2-one

To a stirred solution of 6-chloro-N$^2$-cyclopropylpyridine-2,3-diamine Int-8 (300 mg, 1.64 mmol) in THF (5 mL) was added 1,1'-carbonyldiimidazole (398 mg, 2.46 mmol) at room temperature under an inert atmosphere and the mixture was stirred for 16 h. After consumption of starting material (by TLC), the reaction mixture was diluted with 1 N HCl (10 mL) and extracted with EtOAc (2×10 mL). The combined organic extracts were dried over anhydrous Na$_2$SO$_4$ and concentrated under reduced pressure to afford 5-chloro-3-cyclopropyl-1,3-dihydro-2H-imidazo[4,5-b]pyridin-2-one (200 mg, crude) as a black solid. The crude material was taken to the next step without further purification.

2-bromo-5-chloro-3-cyclopropyl-3H-imidazo[4,5-b]pyridine

To a stirred solution of 5-chloro-3-cyclopropyl-1,3-dihydro-2H-imidazo[4,5-b]pyridin-2-one (200 mg, crude) in toluene (10 mL) was added phosphoryl bromide (1.09 g, 3.82 mmol) at room temperature under an inert atmosphere. The reaction mixture was heated to 80° C. and stirred for 16 h. After consumption of starting material (by TLC), the reaction mixture was diluted with CH$_2$Cl$_2$ (10 mL), warm water (10 mL) and the mixture was stirred for 30 min. The reaction mixture was basified using aqueous Na$_2$CO$_3$ solution to pH~10 and extracted with CH$_2$Cl$_2$ (2×10 mL). The combined organic extracts were washed with water (20 mL), dried over anhydrous Na$_2$SO$_4$ and concentrated under reduced pressure. The crude material was purified by silica gel column chromatography (eluent: 10% EtOAc/hexane) to afford 2-bromo-5-chloro-3-cyclopropyl-3H-imidazo[4,5-b]pyridine (70 mg, 0.25 mmol, 27% for two steps) as an off-white solid.

$^1$H NMR (400 MHz, DMSO-d$_6$): δ 8.07 (d, J=8.4 Hz, 1H), 7.36 (d, J=8.4 Hz, 1H), 3.40-3.32 (m, 1H), 1.26-1.19 (m, 4H)

5-chloro-3-cyclopropyl-2-(5,6-difluoro-1H-benzo[d]imidazol-1-yl)-3H-imidazo[4,5-b] pyridine (Ex. 29)

To a stirred solution of 2-bromo-5-chloro-3-cyclopropyl-3H-imidazo[4,5-b]pyridine (70 mg, 0.25 mmol) in DMSO (5 mL) was added potassium carbonate (107 mg, 0.77 mmol) and 5,6-difluoro-1H-benzo[d]imidazole (79 mg, 0.51 mmol) at room temperature under an inert atmosphere. The reaction mixture was heated to 80° C. and stirred for 16 h. After consumption of starting material (by TLC), the reaction mixture was diluted with ice cold water (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 5-chloro-3-cyclopropyl-2-(5,6-difluoro-1H-benzo[d]imidazol-1-yl)-3H-imidazo[4,5-b]pyridine Ex. 29 (50 mg, 0.14 mmol, 56%) as an off white solid.

$^1$H NMR (400 MHz, DMSO-d$_6$): δ 9.01 (s, 1H), 8.24 (d, J=9.2 Hz, 1H), 8.03-7.96 (m, 2H), 7.49 (dd, J=9.0 Hz, 1H), 3.68-3.61 (m, 1H), 1.08-1.01 (m, 2H), 0.82-0.77 (m, 2H)

LC-MS: m/z 345.9 [M+H]$^+$ at 3.03 RT (99.62% purity)
HPLC: 99.87%

Example 30

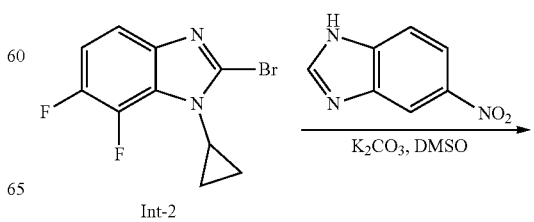

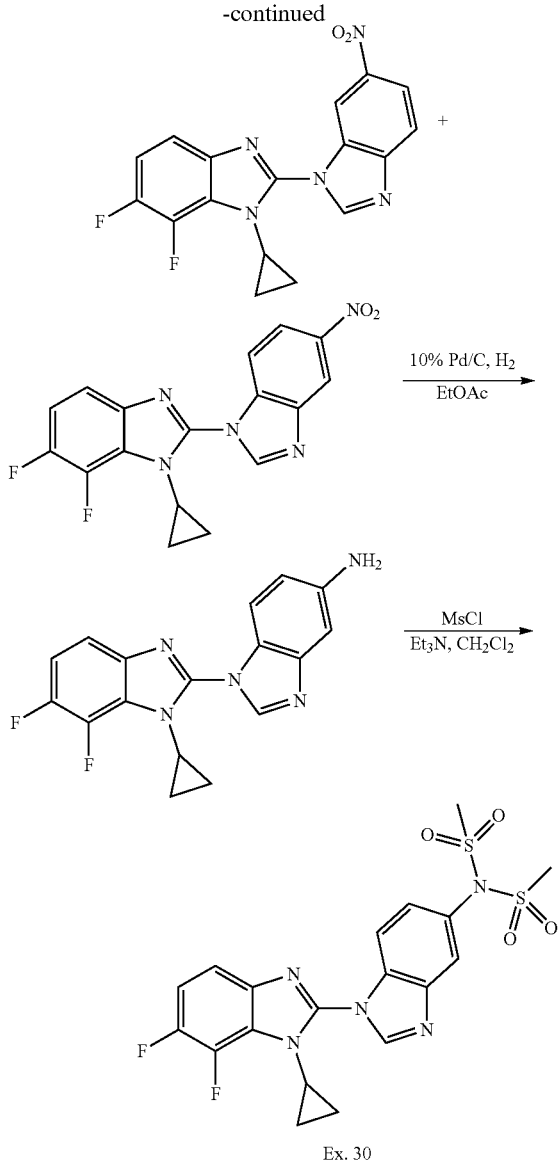

Ex. 30

1'-cyclopropyl-6',7'-difluoro-5-nitro-1'H-1,2'-bibenzo[d]imidazole & 1'-cyclopropyl-6',7'-difluoro-6-nitro-1'H-1,2'-bibenzo[d]imidazole To a stirred solution of 2-bromo-1-cyclopropyl-6,7-difluoro-1H-benzo[d]imidazole Int-2 (200 mg, 0.73 mmol) in DMSO (2 mL) was added 5-nitro-1H-benzo[d]imidazole (120 mg, 0.73 mmol) and potassium carbonate (305 mg, 2.21 mmol) at room temperature under an inert atmosphere. The reaction mixture was heated to 100° C. and stirred for 16 h. After consumption of starting material (by TLC), the reaction mixture was diluted with ice cold water (30 mL) and extracted with EtOAc (2×20 mL). The combined organic extracts were washed with water (15 mL), brine (20 mL), dried over anhydrous Na₂SO₄ and concentrated under reduced pressure to obtain the crude (~180 mg).

This material was combined with another lot (200 mg crude) and was purified by silica gel column chromatography (eluent: 20% EtOAc/hexane) to afford 1'-cyclopropyl-6',7'-difluoro-5-nitro-1'H-1,2'-bibenzo[d]imidazole (80 mg, 0.22 mmol, 15%) and (180 mg, mixture of isomers) as off-white solids respectively. The pure regio isomer (80 mg) was taken to the next step. The structure was confirmed in the final step.

$^1$H NMR (500 MHz, CDCl$_3$): δ 8.86 (d, J=2.3 Hz, 1H), 8.59 (s, 1H), 8.39 (dd, J=9.0, 2.0 Hz, 1H), 7.97 (d, J=8.7 Hz, 1H), 7.56-7.52 (m, 1H), 7.26-7.22 (m, 1H), 3.69-3.65 (m, 1H), 1.19-1.13 (m, 2H), 0.81-0.76 (m, 2H)

LC-MS: m/z 356 [M+H]$^+$ at 3.14 RT (97.14% purity)

1'-cyclopropyl-6',7'-difluoro-1'H-[1,2'-bibenzo[d]imidazol]-5-amine

To a stirred solution of 1'-cyclopropyl-6',7'-difluoro-5-nitro-1'H-1,2'-bibenzo[d]imidazole (80 mg, 0.22 mmol) in ethylacetate (5 mL) was added 10% Pd/C (15 mg) at room temperature under an inert atmosphere. The reaction mixture was stirred at room temperature under hydrogen atmosphere (balloon pressure) for 6 h. After consumption of starting material (by TLC), the reaction mixture was filtered through a pad of Celite and washed with methanol (30 mL). The filtrate was concentrated under reduced pressure to obtain 1'-cyclopropyl-6',7'-difluoro-1'H-[1,2'-bibenzo[d]imidazol]-5-amine (60 mg, 0.18 mmol, 82%) as a brown solid.

LC-MS: m/z 325.9 [M+H]$^+$ at 2.38 RT (96.51% purity)

N-(1'-cyclopropyl-6',7'-difluoro-1'H-[1,2'-bibenzo[d]imidazol]-5-yl)-N-(methylsulfonyl) methanesulfonamide (Ex. 30)

To a stirred solution of 1'-cyclopropyl-6',7'-difluoro-1'H-[1,2'-bibenzo[d]imidazol]-5-amine (60 mg, 0.18) in CH$_2$Cl$_2$ (3 mL) was added triethylamine (0.05 mL, 0.36 mmol) and methanesulfonyl chloride (0.02 mL, 0.22 mmol) at 0° C. under an inert atmosphere. The reaction mixture was gradually warmed to room temperature and stirred for 30 min. After consumption of starting material (by TLC), the reaction mixture was diluted with water (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: EtOAc) to afford N-(1'-cyclopropyl-6',7'-difluoro-1'H-[1,2'-bibenzo[d]imidazol]-5-yl)-N-(methylsulfonyl) methanesulfonamide Ex. 30 (40 mg, 0.08 mmol, 54%) as an off-white solid. The structure was further confirmed by 2 D NMR (NOESY, DQFCOSY).

$^1$H NMR (500 MHz, DMSO-d$_6$): δ 9.04 (s, 1H), 8.09 (s, 1H), 7.96 (d, J=8.7 Hz, 1H), 7.59 (dd, J=8.7, 3.5 Hz, 1H), 7.55 (dd, J=8.7, 2.3 Hz, 1H), 7.43-7.37 (m, 1H), 3.95-3.92 (m, 1H), 3.59 (s, 6H), 1.02-0.97 (m, 2H), 0.80-0.78 (m, 2H)

LC-MS: m/z 481.9 [M+H]$^+$ at 2.85 RT (98.72% purity)
HPLC: 96.03%

Example 31 & Example 33

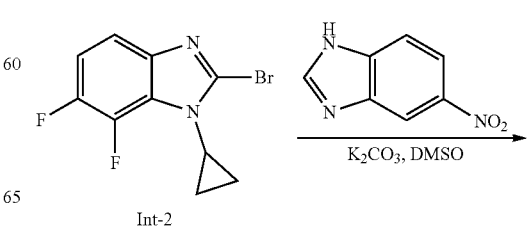

Int-2

67
-continued

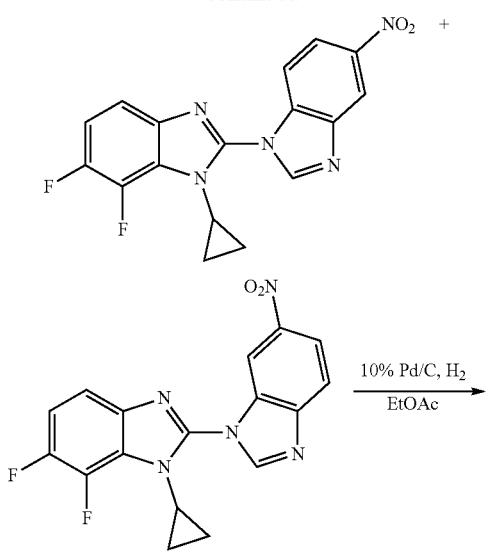

68
-continued

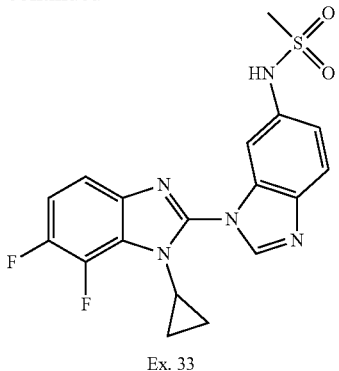 [SMILES: CS(=O)(=O)Nc1ccc2ncn(-c3nc4ccc(F)c(F)c4n3C3CC3)c2c1]

1'-cyclopropyl-6',7'-difluoro-5-nitro-1'H-1,2'-bibenzo[d]imidazole & 1'-cyclopropyl-6',7'-difluoro-6-nitro-1'H-1,2'-bibenzo[d]imidazole To a stirred solution of 2-bromo-1-cyclopropyl-6,7-difluoro-1H-benzo[d]imidazole Int-2 (200 mg, 0.73 mmol) in DMSO (2 mL) was added 5-nitro-1H-benzo[d]imidazole (120 mg, 0.73 mmol) and potassium carbonate (305 mg, 2.21 mmol) at room temperature under inert atmosphere. The reaction mixture was heated to 100° C. and stirred for 16 h. After consumption of starting material (by TLC), the reaction mixture was diluted with ice cold water (30 mL) and extracted with EtOAc (2×20 mL). The combined organic extracts were washed with water (15 mL), brine (20 mL), dried over anhydrous Na₂SO₄ and concentrated under reduced pressure to obtain the crude (~180 mg).

This material was combined with another lot (200 mg crude) and was purified by silica gel column chromatography (eluent: 20% EtOAc/hexane) to afford 1'-cyclopropyl-6',7'-difluoro-5-nitro-1'H-1,2'-bibenzo[d]imidazole (80 mg, 0.22 mmol, 15%) and 180 mg of the mixture of isomers as off-white solids respectively. The mixture was taken to next step without further purification.

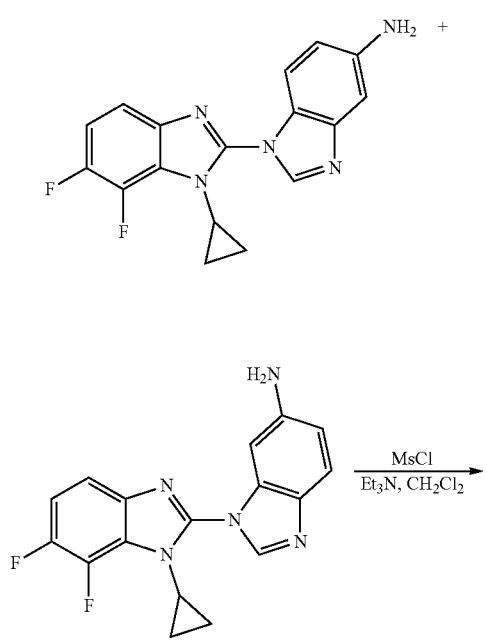

1'-cyclopropyl-6',7'-difluoro-1'H-[1,2'-bibenzo[d]imidazol]-5-amine & 1'-cyclopropyl-6',7'-difluoro-1'H-[1,2'-bibenzo[d]imidazol]-6-amine To a stirred solution of 1'-cyclopropyl-6',7'-difluoro-5-nitro-1'H-1,2'-bibenzo[d]imidazole & 1'-cyclopropyl-6',7'-difluoro-6-nitro-1'H-1,2'-bibenzo[d]imidazole (180 mg, mixture of isomers) in ethylacetate (12 mL) was added 10% Pd/C (40 mg) at room temperature under inert atmosphere. The reaction mixture was stirred at room temperature under hydrogen atmosphere (balloon pressure) for 6 h. After consumption of starting material (by TLC), the reaction mixture was filtered through a pad of celite and the celite bed was washed with methanol (30 mL). The filtrate was concentrated under reduced pressure to obtain 1'-cyclopropyl-6',7'-difluoro-1'H-[1,2'-bibenzo[d]imidazol]-5-amine & 1'-cyclopropyl-6',7'-difluoro-1'H-[1,2'-bibenzo[d]imidazol]-6-amine (130 mg, mixture of isomers) as a brown solid.

N-(1'-cyclopropyl-6',7'-difluoro-1'H-[1,2'-bibenzo[d]imidazol]-5-yl) methanesulfonamide (Ex. 31) & N-(1'-cyclopropyl-6',7'-difluoro-1'H-[1,2'-bibenzo[d]imidazol]-6-yl) methanesulfonamide (Ex. 33)

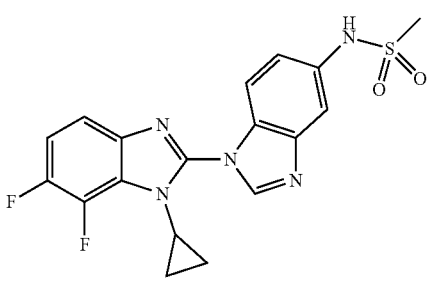

To a stirred solution of 1'-cyclopropyl-6',7'-difluoro-1'H-[1,2'-bibenzo[d]imidazol]-5-amine (130 mg, mixture of isomers) in CH₂Cl₂ (8 mL) was added triethylamine (0.11 mL, 0.5 mmol) and methanesulfonyl chloride (0.03 mL, 0.24 mmol) at 0° C. under inert atmosphere. The reaction mixture was stirred at 0° C. for 30 min. After consumption of starting material (by TLC), the reaction mixture was diluted with water (20 mL) and extracted with CH₂Cl₂ (2×20 mL). The combined organic extracts were dried over anhydrous Na₂SO₄ and concentrated under reduced pressure. The crude material was purified by silica gel column chromatography (eluent: 50% EtOAc/hexane) followed by chiral preparative HPLC to afford N-(1'-cyclopropyl-6',7'-difluoro-1'H-[1,2'-bibenzo[d]imidazol]-5-yl) methanesulfonamide Ex. 31 (30 mg, 0.07 mmol, 19%) & N-(1'-cyclopropyl-6',7'-difluoro-1'H-[1,2'-bibenzo[d]imidazol]-6-yl) methanesulfonamide Ex. 32 (30 mg, 0.07 mmol, 19%) as pale yellow solids respectively. The two structures were confirmed by 2 D NMR (NOESY, DQFCOSY).

Analytical Data of Ex. 31:

¹H NMR (500 MHz, DMSO-d₆): δ 9.70 (br s, 1H), 8.87 (s, 1H), 7.82 (d, J=8.7 Hz, 1H), 7.65 (d, J=1.7 Hz, 1H), 7.56 (dd, J=9.0, 3.8 Hz, 1H), 7.40-7.37 (m, 1H), 7.28 (dd, J=8.7, 2.3 Hz, 1H), 3.90-3.86 (m, 1H), 2.97 (s, 3H), 1.02-0.91 (m, 2H), 0.73-0.71 (m, 2H).

LC-MS: m/z 404.0 [M+H]⁺ at 2.57 RT (99.65% purity). HPLC: 98.78%.

Analytical Data of Ex. 33:

¹H NMR (500 MHz, DMSO-d₆): δ 9.66 (br s, 1H), 8.83 (s, 1H), 7.78 (d, J=8.7 Hz, 1H), 7.74 (s, 1H), 7.56 (dd, J=8.7, 3.5 Hz, 1H), 7.40-7.35 (m, 1H), 7.26 (dd, J=8.7, 1.7 Hz, 1H), 3.94-3.78 (m, 1H), 2.94 (s, 3H), 0.99-0.92 (m, 2H), 0.74-0.72 (m, 2H)

LC-MS: m/z 404.0 [M+H]⁺ at 2.51 RT (99.34% purity) HPLC: 99.25%

Example 32

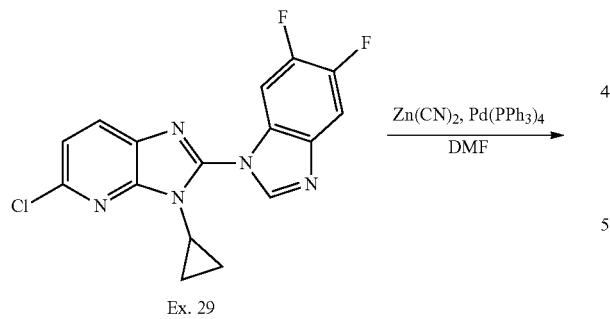

Ex. 32

3-cyclopropyl-2-(5,6-difluoro-1H-benzo[d]imidazol-1-yl)-3H-imidaz[4,5-b]pyridine-5-carbonitrile (Ex. 32)

To a stirred solution of 5-chloro-3-cyclopropyl-2-(5,6-difluoro-1H-benzo[d]imidazol-1-yl)-3H-imidazo[4,5-b]pyridine Ex. 29 (100 mg, 0.28 mmol) in DMF (2 mL) was added zinc cyanide (34 mg, 0.28 mmol) and Pd(PPh₃)₄ (34 mg, 0.02 mmol) in sealed tube at room temperature and the mixture was purged under argon for 10 min. The reaction mixture was heated to 100° C. and stirred for 16 h. After consumption of starting material (by TLC), the reaction mixture was diluted with ice cold water (20 mL) and extracted with EtOAc (2×20 mL). The combined organic extracts were dried over anhydrous Na₂SO₄ and concentrated under reduced pressure. The crude material was purified by preparative HPLC to afford 3-cyclopropyl-2-(5,6-difluoro-1H-benzo[d]imidazol-1-yl)-3H-imidazo[4,5-b]pyridine-5-carbonitrile Ex. 32 (40 mg, 0.11 mmol, 41%) as an off-white solid.

¹H NMR (500 MHz, DMSO-d₆): δ 9.12 (s, 1H), 8.39 (d, J=8.1 Hz, 1H), 8.09 (dd, J=10.4, 7.0 Hz, 1H), 8.01-7.98 (m, 2H), 3.81-3.71 (m, 1H), 1.18-1.07 (m, 2H), 0.91-0.83 (m, 2H)

LC-MS: m/z 336.9 [M+H]⁺ at 2.87 RT (98.89% purity) HPLC: 99.49%

Example 34

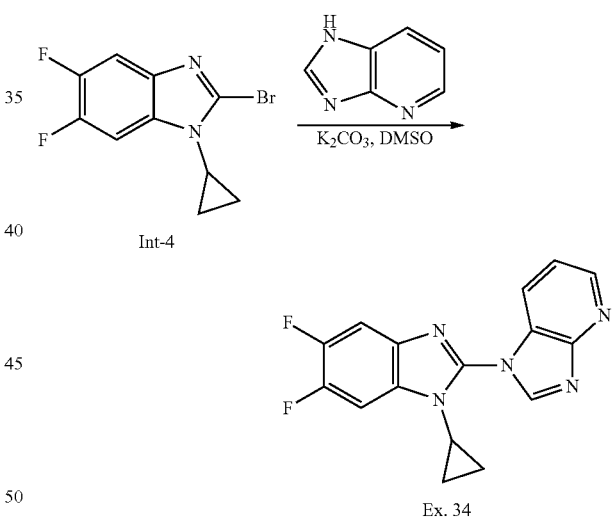

1-(1-cyclopropyl-5,6-difluoro-1H-benzo[d]imidazol-2-yl)-1H-imidazo[4,5-b]pyridine (Ex. 34)

To a stirred solution of 2-bromo-1-cyclopropyl-5,6-difluoro-1H-benzo[d]imidazole Int-4 (100 mg, 0.36 mmol) in DMSO (1 mL) was added 1H-imidazo[4,5-b]pyridine (52 mg, 0.44 mmol) and potassium carbonate (152 mg, 1.10 mmol) at room temperature under an inert atmosphere. The reaction mixture was heated to 90° C. and stirred for 16 h. After consumption of starting material (by TLC), the reaction mixture was diluted with ice cold water (20 mL) and extracted with EtOAc (2×50 mL). The combined organic extracts were washed with water (20 mL), brine (20 mL), dried over anhydrous Na₂SO₄ and concentrated under reduced pressure. The crude material was purified by silica gel column chromatography (eluent: 2% MeOH/CH$_2$Cl$_2$) to afford 1-(1-cyclopropyl-5,6-difluoro-1H-benzo[d]imidazol-2-yl)-1H-imidazo[4,5-b]pyridine Ex. 34 (60 mg, 0.19 mmol, 52%) as a pale yellow solid. The structure was further confirmed by 2 D NMR (NOESY, DQFCOSY).

$^1$H NMR (400 MHz, DMSO-d$_6$): δ 9.18 (s, 1H), 8.59 (dd, J=4.8, 1.6 Hz, 1H), 8.31 (dd, J=8.2, 1.6 Hz, 1H), 7.90-7.84 (m, 2H), 7.46 (dd, J=8.2, 4.8 Hz, 1H), 3.78-3.55 (m, 1H), 1.10-0.94 (m, 2H), 0.75-0.57 (m, 2H)

LC-MS: m/z 311.9 [M+H]$^+$ at 2.37 RT (98.26% purity) HPLC: 96.30%

Example 35 & Example 36

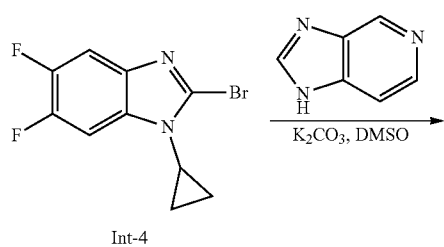

Int-4

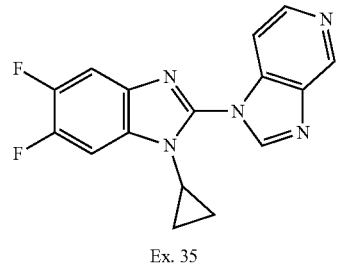

Ex. 35

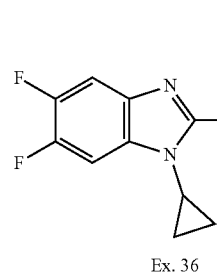

Ex. 36

1-(1-cyclopropyl-5,6-difluoro-1H-benzo[d]imidazol-2-yl)-1H-imidazo[4,5-c]pyridine (Ex. 35) & 3-(1-cyclopropyl-5,6-difluoro-1H-benzo[d]imidazol-2-yl)-3H-imidazo[4,5-c] pyridine (Ex. 36)

To a stirred solution of 2-bromo-1-cyclopropyl-5,6-difluoro-1H-benzo[d]imidazole Int-4 (150 mg, 0.55 mmol) in DMSO (2 mL) was added 1H-imidazo[4,5-c]pyridine (98 mg, 0.83 mmol) and potassium carbonate (229 mg, 1.66 mmol) at room temperature under an inert atmosphere. The reaction mixture heated to 100° C. and stirred for 16 h. After consumption of starting material (by TLC), the reaction mixture was diluted with ice cold water (20 mL) and extracted with EtOAc (2×20 mL). The combined organic extracts were washed with water (20 mL), brine (20 mL), dried over anhydrous Na$_2$SO$_4$ and concentrated under reduced pressure. The crude material was purified by preparative HPLC to afford 1-(1-cyclopropyl-5,6-difluoro-1H-benzo[d]imidazol-2-yl)-1H-imidazo[4,5-c]pyridine Ex. 35 (32 mg, 0.1 mmol, 19%) as an off-white solid & 3-(1-cyclopropyl-5,6-difluoro-1H-benzo[d]imidazol-2-yl)-3H-imidazo[4,5-c]pyridine Ex. 36 (28 mg, 0.09 mmol, 16%) as off-white solids respectively. The structures were confirmed by 2D NMR (NOESY, DQFCOSY).

Analytical Data for B-510:

$^1$H NMR (400 MHz, CD$_3$OD): δ 9.12 (s, 1H), 9.91 (s, 1H), 8.53 (d, J=5.6 Hz, 1H), 7.91 (dd, J=5.6, 0.8 Hz, 1H), 7.72 (dd, J=10.0, 7.0 Hz, 1H), 7.66 (dd, J=10.4, 7.3 Hz, 1H), 3.74-3.68 (m, 1H), 1.12-1.06 (m, 2H), 0.75-0.69 (m, 2H)

LC-MS: m/z 311.9 [M+H]$^+$ at 2.29 RT (99.86% purity) HPLC: 99.93% Analytical data for B-511:

$^1$H NMR (400 MHz, CD$_3$OD): δ 9.22 (s, 1H), 9.08 (s, 1H), 8.55 (d, J=5.6 Hz, 1H), 7.91 (dd, J=5.6, 0.8 Hz, 1H), 7.72 (dd, J=10.0, 7.0 Hz, 1H), 7.66 (dd, J=10.4, 7.3 Hz, 1H), 3.74-3.68 (m, 1H), 1.16-1.05 (m, 2H), 0.78-0.71 (m, 2H)

LC-MS: m/z 311.9 [M+H]$^+$ at 2.26 RT (99.79% purity) HPLC: 99.74%

Example 37 & Example 38

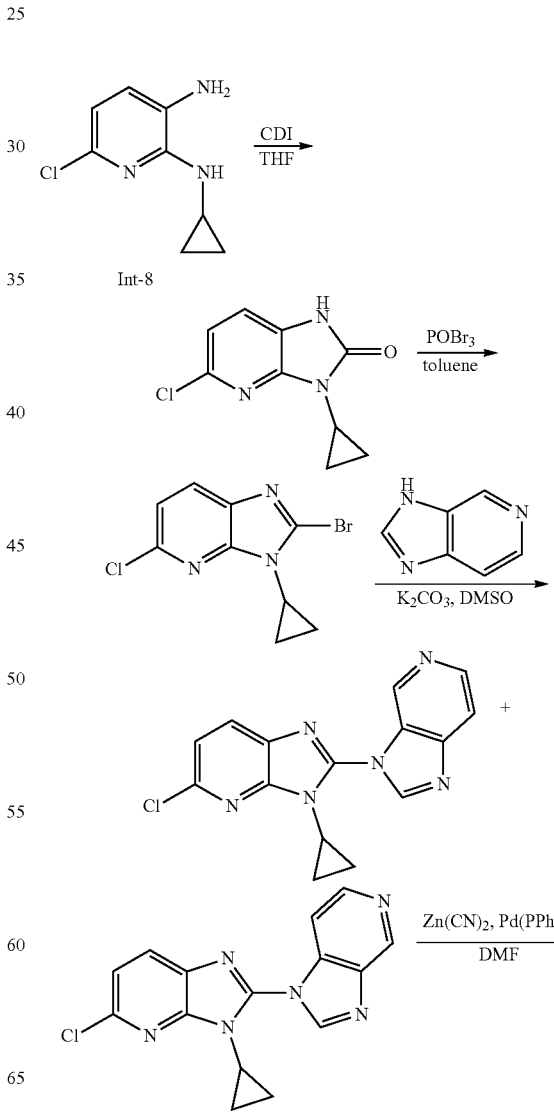

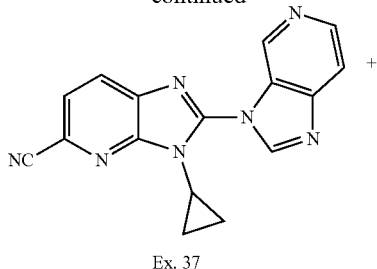

Ex. 37

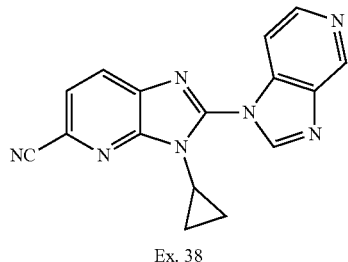

Ex. 38

5-chloro-3-cyclopropyl-1,3-dihydro-2H-imidazo[4,5-b]pyridin-2-one

To a stirred solution of 6-chloro-$N^2$-cyclopropylpyridine-2,3-diamine Int-8 (300 mg, 1.64 mmol) in THF (5 mL) was added 1,1'-carbonyldiimidazole (398 mg, 2.46 mmol) at room temperature under an inert atmosphere and the mixture was stirred for 16 h. After consumption of starting material (by TLC), the reaction mixture was quenched with 1 N HCl (10 mL) and extracted with EtOAc (2×10 mL). The combined organic extracts were dried over anhydrous $Na_2SO_4$ and concentrated under reduced pressure to afford 5-chloro-3-cyclopropyl-1,3-dihydro-2H-imidazo[4,5-b]pyridin-2-one (200 mg, crude) as a black solid. The crude material was taken to the next step without further purification.

2-bromo-5-chloro-3-cyclopropyl-3H-imidazo[4,5-b]pyridine

To a stirred solution of 5-chloro-3-cyclopropyl-1,3-dihydro-2H-imidazo[4,5-b]pyridin-2-one (200 mg, crude) in toluene (10 mL) was added phosphoryl bromide (1.09 g, 3.82 mmol) at room temperature under an inert atmosphere. The reaction mixture was heated to 80° C. and stirred for 16 h. After consumption of starting material (by TLC), the reaction mixture was diluted with $CH_2Cl_2$ (10 mL) and warm water (10 mL) and stirred for 30 min. The reaction mixture was basified using aqueous $Na_2CO_3$ solution to pH~10 and extracted with $CH_2Cl_2$ (2×10 mL). The combined organic extracts were washed with water (20 mL), dried over anhydrous $Na_2SO_4$ and concentrated under reduced pressure. The crude material was purified by silica gel column chromatography (eluent: 10% EtOAc/hexane) to afford 2-bromo-5-chloro-3-cyclopropyl-3H-imidaz [4,5-b]pyridine (70 mg, 0.25 mmol, 27% for two steps) as an off-white solid.

$^1$H NMR (400 MHz, DMSO-$d_6$): δ 8.07 (d, J=8.4 Hz, 1H), 7.36 (d, J=8.4 Hz, 1H), 3.40-3.32 (m, 1H), 1.26-1.19 (m, 4H)

5-chloro-3-cyclopropyl-2-(3H-imidazo[4,5-c]pyridin-3-yl)-3H-imidazo[4,5-b]pyridine To a stirred solution of 2-bromo-5-chloro-3-cyclopropyl-3H-imidazo[4,5-b]pyridine (500 mg, 1.83 mmol) in DMSO (5 mL) was added 3H-imidazo[4,5-c]pyridine (219 mg, 1.83 mmol) and potassium carbonate (761 mg, 5.51 mmol) at room temperature under inert atmosphere. The reaction mixture was heated to 80° C. and stirred for 16 h. After consumption of starting material (by TLC), the reaction mixture was diluted with water (30 mL) and extracted with EtOAc (2×30 mL). The combined organic extracts were dried over anhydrous $Na_2SO_4$ and concentrated under reduced pressure. The crude material was purified by silica gel column chromatography (eluent: 5% MeOH/$CH_2Cl_2$) to afford 5-chloro-3-cyclopropyl-2-(3H-imidazo[4,5-c]pyridin-3-yl)-3H-imidazo[4,5-b]pyridine and regioisomer (350 mg) as an off white solid.

$^1$H NMR (500 MHz, DMSO-$d_6$): δ 9.20-9.15 (m, 1H), 9.08 (s, 1H), 8.55 (d, J=5.2 Hz, 1H), 8.29-8.23 (m, 1H), 8.00-7.86 (m, 1H), 7.52-7.48 (m, 1H), 3.77-3.67 (m, 1H), 1.09-0.99 (m, 2H), 0.87-0.76 (m, 2H)

3-cyclopropyl-2-(3H-imidazo[4,5-c]pyridin-3-yl)-3H-imidazo[4,5-b]pyridine-5-carbonitrile (Ex. 37) & 3-cyclopropyl-2-(1H-imidazo[4,5-c]pyridin-1-yl)-3H-imidazo[4,5-b]pyridine-5-carbonitrile (Ex. 38)

To a stirred solution of 5-chloro-3-cyclopropyl-2-(3H-imidazo[4,5-c]pyridin-3-yl)-3H-imidazo[4,5-b]pyridine and regioisomer (175 mg, mixture of isomers) in DMF (2.5 mL) was added zinc cyanide (132 mg, 1.13 mmol) in a microwave vessel at room temperature under inert an atmosphere and the mixture was purged under argon for 15 min. To this reaction mixture was added Pd(PPh$_3$)$_4$ (65 mg, 0.06 mmol). The vessel was sealed and irradiated to 150° C. and stirred for 1 h. After consumption of starting material (by TLC), the reaction mixture was diluted with ice cold water (20 mL) and extracted with EtOAc (2×20 mL). The combined organic extracts were dried over anhydrous $Na_2SO_4$ and concentrated under reduced pressure. The crude material was purified by silica gel column chromatography (eluent: 3% MeOH/$CH_2Cl_2$) to afford a mixture of isomers (85 mg) as a pale yellow solid.

This material was combined with another lot (85 mg) and was purified by preparative HPLC to afford 3-cyclopropyl-2-(3H-imidazo[4,5-c]pyridin-3-yl)-3H-imidazo[4,5-b]pyridine-5-carbonitrile Ex. 37 (10 mg, 0.03 mmol) & 3-cyclopropyl-2-(1H-imidazo[4,5-c]pyridin-1-yl)-3H-imidazo[4,5-b]pyridine-5-carbonitrile Ex. 38 (30 mg, 0.1 mmol). The two structures were confirmed by 2 D NMR (NOESY, DQF-COSY).

Analytical Data of Ex. 37:

$^1$H NMR (400 MHz, CD$_3$OD): δ 9.44 (d, J=0.9 Hz, 1H), 9.27 (s, 1H), 8.58 (d, J=5.6 Hz, 1H), 8.28 (d, J=8.2 Hz, 1H), 7.93 (dd, J=5.6, 1.0 Hz, 1H), 7.88 (d, J=8.2 Hz, 1H), 3.80-3.75 (m, 1H), 1.30-1.23 (m, 2H), 1.00-0.94 (m, 2H)

LC-MS: m/z 301.9 [M+H]$^+$ at 1.92 RT (95.35% purity)

HPLC: 98.60% Analytical data of Ex. 38:

$^1$H NMR (400 MHz, CD$_3$OD): δ 9.15-9.12 (m, 2H), 8.57 (d, J=5.8 Hz, 1H), 8.28 (d, J=8.3 Hz, 1H), 8.14 (dd, J=5.8, 1.0 Hz, 1H), 7.89 (d, J=8.3 Hz, 1H), 3.77-3.72 (m, 1H), 1.23-1.19 (m, 2H), 0.94-0.88 (m, 2H)

LC-MS: m/z 301.9 [M+H]$^+$ at 1.91 RT (99.31% purity)

HPLC: 99.25%

Example 39

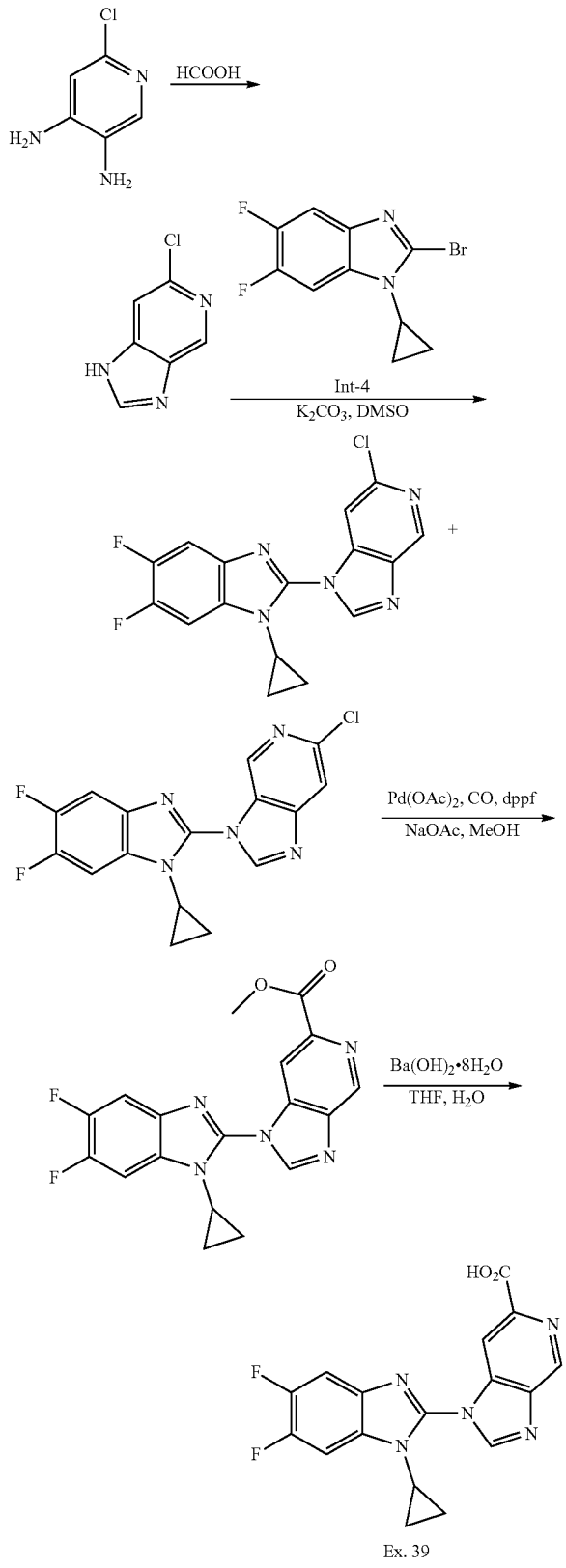

6-chloro-1H-imidazo[4,5-c]pyridine

To 6-chloropyridine-3,4-diamine (2 g, 13.99 mmol) was added formic acid (20 mL) at room temperature under an inert atmosphere. The reaction mixture was heated to 120° C. and stirred for 16 h. After consumption of starting material (by TLC), the reaction mixture was basified using saturated NaHCO$_3$ solution (100 mL) and extracted with EtOAc (2×100 mL). The combined organic extracts were dried over anhydrous Na$_2$SO$_4$ and concentrated under reduced pressure to afford 6-chloro-1H-imidazo[4,5-c]pyridine (2 g) as a pale brown solid. The crude material was taken to the next step without further purification.

LC-MS: m/z 151.9 [M–H]$^-$ at 6.38 RT (59.98% purity)

6-chloro-1-(1-cyclopropyl-5,6-difluoro-1H-benzo[d]imidazol-2-yl)-1H-imidazo[4,5-c]pyridine To a stirred solution of 2-bromo-1-cyclopropyl-5,6-difluoro-1H-benzo[d]imidazole Int-4 (1.5 g, 5.49 mmol) in DMSO (15 mL) was added 6-chloro-1H-imidazo[4,5-c]pyridine (841 mg, 5.49 mmol) and potassium carbonate (2.27 g, 16.48 mmol) at room temperature under an inert atmosphere. The reaction mixture was heated to 80° C. and stirred for 16 h. After consumption of starting material (by TLC), the reaction mixture was diluted with water (100 mL) and extracted with EtOAc (2×40 mL). The combined organic extracts were dried over anhydrous Na$_2$SO$_4$ and concentrated under reduced pressure. The crude material was purified by silica gel column chromatography (eluent: 40-50% EtOAc/hexane) to afford 6-chloro-1-(1-cyclopropyl-5,6-difluoro-1H-benzo[d]imidazol-2-yl)-1H-imidazo[4,5-c]pyridine and the associated regioisomer (750 mg, mixture of isomers) as an off white solid. The mixture was taken to the next step without further purification.

LC-MS: m/z 346.4 [M+H]$^+$ at 3.58 RT (96.38% purity)

methyl 1-(1-cyclopropyl-5,6-difluoro-1H-benzo[d]imidazol-2-yl)-1H-imidazo[4,5-c] pyridine-6-carboxylate To a stirred solution of 6-chloro-1-(1-cyclopropyl-5,6-difluoro-1H-benzo[d]imidazol-2-yl)-1H-imidazo[4,5-c pyridine and regioisomer (500 mg, mixture) in methanol (30 mL) was added sodium acetate (356 mg, 4.35 mmol), dppf (40 mg, 0.07 mmol) followed by Pd(OAc)$_2$ (49 mg, 0.07 mmol) at room temperature under an inert atmosphere. To this reaction mixture, CO gas was passed under 200 psi pressure and the reaction was heated to 100° C. and stirred for 28 h. After consumption of starting material (by TLC), the reaction mixture was diluted with EtOAc (80 mL) and washed with water (30 mL). The combined organic extracts were dried over anhydrous Na$_2$SO$_4$ and concentrated under reduced pressure. The crude material was purified by silica gel column chromatography (eluent: 100% EtOAc) to afford methyl 1-(1-cyclopropyl-5,6-difluoro-1H-benzo[d]imidazol-2-yl)-1H-imidazo[4,5-c]pyridine-6-carboxylate (170 mg, 0.46 mmol, 32%) as a pale brown solid. The structure was confirmed by 2 D NMR (NOESY, gDQFCOSY).

$^1$H NMR (400 MHz, DMSO-d$_6$): δ 9.29 (s, 1H), 9.24 (d, J=1.0 Hz, 1H), 8.61 (d, J=1.0 Hz, 1H), 7.99 (dd, J=10.9, 7.4 Hz, 1H), 7.89 (dd, J=10.4, 7.3 Hz, 1H), 3.90 (s, 3H), 3.77-3.71 (m, 1H), 1.06-1.00 (m, 2H), 0.74-0.68 (m, 2H)

LC-MS: m/z 370.1 [M+H]$^+$ at 2.50 RT (96.82% purity)

1-(1-cyclopropyl-5,6-difluoro-1H-benzo[d]imidazol-2-yl)-1H-imidazo[4,5-c]pyridine-6-carboxylic acid
(Ex. 39)

To a stirred solution of methyl 1-(1-cyclopropyl-5,6-difluoro-1H-benzo[d]imidazol-2-yl)-1H-imidazo[4,5-c]pyridine-6-carboxylate (30 mg, 0.08 mmol) in a mixture of THF (0.4 mL) and water (0.3 mL) was added barium hydroxide octahydrate (51 mg, 0.16 mmol) at room temperature and the mixture was stirred for 3 h. After consumption of starting material (by TLC), the reaction mixture was quenched with dry ice. The obtained solid was filtered and the filtrate was lyophilized to afford 1-(1-cyclopropyl-5,6-difluoro-1H-benzo[d]imidazol-2-yl)-1H-imidazo[4,5-c]pyridine-6-carboxylic acid Ex. 39 (16 mg, 0.04 mmol, 57%) as an off white solid.

$^1$H NMR (400 MHz, THF+D$_2$O): δ 9.19 (brs, 1H), 8.92 (s, 1H), 8.56-8.40 (m, 1H), 7.78-7.54 (m, 2H), 3.78-3.76 (m, 1H), 1.05-1.01 (m, 2H), 0.58-0.54 (m, 2H)

LC-MS: m/z 356.2 [M+H]$^+$ at 1.75 RT (95.96% purity)
HPLC: 97.81%

Example 40

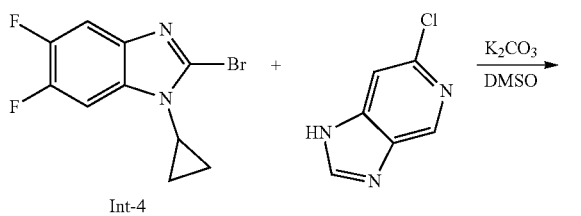

Int-4

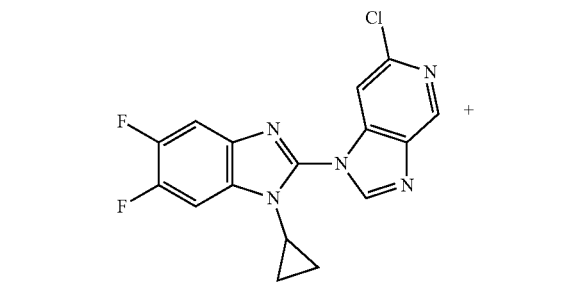

major isomer

+

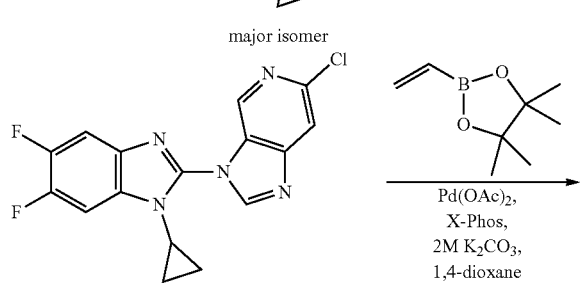

minor isomer

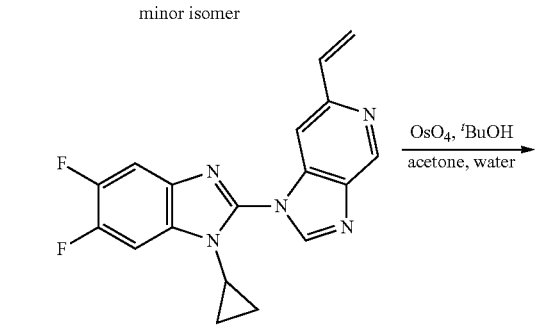

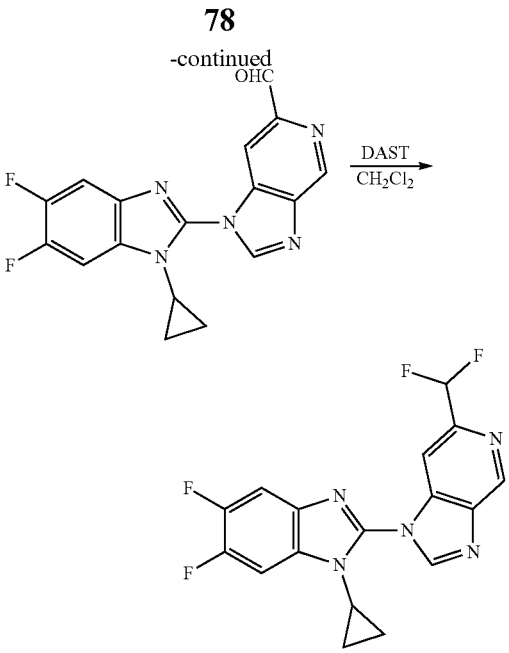

Ex. 40

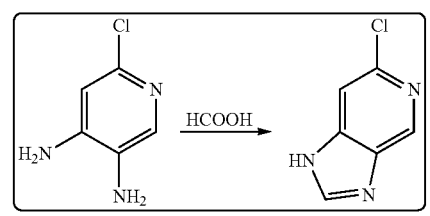 [SMILES: Nc1cnc(Cl)cc1N ; "HCOOH" ; Clc1cc2[nH]cnc2cn1]

6-chloro-1H-imidazo[4,5-c]pyridine

To 6-chloropyridine-3,4-diamine (2 g, 13.99 mmol) was added formic acid (20 mL) at room temperature under an inert atmosphere. The reaction mixture was heated to 120° C. and stirred for 16 h. After consumption of starting material (by TLC), the reaction mixture was basified using saturated NaHCO$_3$ solution (100 mL) and extracted with EtOAc (2×100 mL). The combined organic extracts were dried over anhydrous Na$_2$SO$_4$ and concentrated under reduced pressure to afford 6-chloro-1H-imidazo[4,5-c]pyridine (2 g) as a pale brown solid. The crude material was taken to the next step without further purification.

LC-MS: m/z 151.9 [M−H]$^-$ at 6.38 RT (59.98% purity)

6-chloro-1-(1-cyclopropyl-5,6-difluoro-1H-benzo[d]imidazol-2-yl)-1H-imidazo[4,5-c]pyridine To a stirred solution of 2-bromo-1-cyclopropyl-5,6-difluoro-1H-benzo[d]imidazole Int-4 (2.5 g, 9.16 mmol) in DMSO (25 mL) was added 6-chloro-1H-imidazo[4,5-c]pyridine (1.4 g, crude) and potassium carbonate (3.79 g, 27.47 mmol) at room temperature under an inert atmosphere. The reaction mixture was heated to 90° C. and stirred for 16 h. After consumption of starting material (by TLC), the reaction mixture was poured into water (100 mL) and extracted with EtOAc (2×100 mL). The combined organic extracts were dried over anhydrous Na$_2$SO$_4$ and concentrated under reduced pressure. The crude material was purified by silica gel column chromatography (eluent: 1-2% MeOH/CH$_2$Cl$_2$) to afford 6-chloro-1-(1-cyclopropyl-5,6-difluoro-1H-benzo[d]imidazol-2-yl)-1H-imidazo[4,5-c]pyridine major isomer (1.2 g, 3.47 mmol) and 2 a minor isomer (500 mg, 1.45 mmol) as off white solids respectively.
Analytical Data of Major Isomer:
$^1$H NMR (400 MHz, DMSO-$d_6$): δ 9.23 (s, 1H), 9.04 (d, J=0.8 Hz, 1H), 8.03 (d, J=0.8 Hz, 1H), 7.94-7.85 (m, 2H), 3.78-3.72 (m, 1H), 1.08-1.02 (m, 2H), 0.77-0.72 (m, 2H)
LC-MS: m/z 345.9 [M+H]$^+$ at 2.83 RT (97.53% purity)
Analytical Data of Minor Isomer:
$^1$H NMR (400 MHz, DMSO-$d_6$): δ 9.11 (s, 1H), 8.98 (d, J=0.8 Hz, 1H), 7.99 (d, J=1.0 Hz, 1H), 7.95-7.83 (m, 2H), 3.75-3.69 (m, 1H), 1.06-0.99 (m, 2H), 0.76-0.69 (m, 2H)
LC-MS: m/z 345.9 [M+H]$^+$ at 2.84 RT (76.09% purity)

1-(1-cyclopropyl-5,6-difluoro-1H-benzo[d]imidazol-2-yl)-6-vinyl-1H-imidazo[4,5-c]pyridine To a stirred solution of 6-chloro-1-(1-cyclopropyl-5,6-difluoro-1H-benzo[d]imidazol-2-yl)-1H-imidazo[4,5-c]pyridine (major isomer) (200 mg, 0.58 mmol) in 1,4-dioxane (4 mL) was added 4,4,5,5-tetramethyl-2-vinyl-1,3,2-dioxaborolane (178 mg, 1.16 mmol) and a solution of aqueous potassium carbonate (2 M, 0.6 mL) in a sealed tube at room temperature and purged under argon for 5 min. To this reaction mixture was added Pd(OAc)$_2$ (20 mg, 0.03 mmol) and X-Phos (41 mg, 0.09 mmol) and the mixture was again degassed under argon for 5 min. The reaction mixture was heated to 80° C. and stirred for 16 h. After consumption of starting material (by TLC), the reaction mixture was poured into water (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1-(1-cyclopropyl-5,6-difluoro-1H-benzo[d imidazol-2-yl)-6-vinyl-1H-imidazo[4,5-c]pyridine (90 mg, 0.27 mmol, 46%) as a yellow solid.
$^1$H NMR (400 MHz, CDCl$_3$): δ 9.19 (d, J=0.8 Hz, 1H), 8.41 (s, 1H), 7.72 (d, J=0.7 Hz, 1H), 7.63 (dd, J=10.1, 7.3 Hz, 1H), 7.43 (dd, J=9.4, 6.9 Hz, 1H), 6.93 (dd, J=17.3, 10.7 Hz, 1H), 6.30 (dd, J=17.3, 1.2 Hz, 1H), 5.50 (dd, J=10.7, 1.2 Hz, 1H), 3.46-3.41 (m, 1H), 1.17-1.11 (m, 2H), 0.76-0.70 (m, 2H)
LC-MS: m/z 338.1 [M+H]$^+$ at 2.70 RT (96.65% purity)

1-(1-cyclopropyl-5,6-difluoro-1H-benzo[d]imidazol-2-yl)-1H-imidazo[4,5-c]pyridine-6-carbaldehyde To a stirred solution of 1-(1-cyclopropyl-5,6-difluoro-1H-benzo[d]imidazol-2-yl)-6-vinyl-1H-imidazo[4,5-c]pyridine (60 mg, 0.18 mmol) in tert-butanol/acetone/water (1:1:1, 3.6 mL) was added sodium periodate (76 mg, 0.36 mmol) followed by a solution of osmium tetroxide (1 M in toluene, 1.2 mL) drop wise at 0° C. under an inert atmosphere. The reaction mixture was gradually warmed to room temperature and stirred for 1 h. After consumption of starting material (by TLC), the reaction mixture was filtered through a pad of Celite and washed with EtOAC (20 mL). The filtrate was extracted with EtOAc (2×10 mL). The combined organic extracts were dried over anhydrous Na$_2$SO$_4$ and concentrated under reduced pressure to afford 1-(1-cyclopropyl-5,6-difluoro-1H-benzo[d]imidazol-2-yl)-1H-imidazo[4,5-c]pyridine-6-carbaldehyde (60 mg) as an off white solid. The crude material was taken to the next step without further purification.
$^1$H NMR (400 MHz, DMSO-$d_6$): δ 10.14 (s, 1H), 9.36 (d, J=0.8 Hz, 1H), 9.33 (s, 1H), 8.48 (d, J=1.0 Hz, 1H), 7.98 (dd, J=10.9, 7.4 Hz, 1H), 7.88 (dd, J=10.4, 7.3 Hz, 1H), 3.79-3.71 (m, 1H), 1.06-1.00 (m, 2H), 0.76-0.70 (m, 2H)
LC-MS: m/z 339.9 [M+H]$^+$ at 2.55 RT (81.70% purity)

1-(1-cyclopropyl-5,6-difluoro-1H-benzo[d]imidazol-2-yl)-6-(difluoromethyl)-1H-imidazo[4,5-c]pyridine
(Ex. 40)

To a stirred solution of 1-(1-cyclopropyl-5,6-difluoro-1H-benzo[d]imidazol-2-yl)-1H-imidazo[4,5-c]pyridine-6-carbaldehyde (60 mg, crude) in CH$_2$Cl$_2$ (3 mL) was added diethylaminosulfur trifluoride (0.05 mL, 0.35 mmol) at 0° C. under an inert atmosphere. The reaction mixture was gradually warmed to room temperature and stirred for 1 h. After consumption of starting material (by TLC), the reaction mixture was basified with saturated NaHCO$_3$ solution (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 20-30% EtOAc/hexane) to afford 1-(1-cyclopropyl-5,6-difluoro-1H-benzo[d]imidazol-2-yl)-6-(difluoromethyl)-1H-imidazo[4,5-c]pyridine Ex. 40 (25 mg, 0.07 mmol, 39% from two steps) as an off white solid. The structure was further confirmed by 2 D NMR (NOESY, DQFCOSY) studies.

$^1$H NMR (400 MHz, DMSO-$d_6$): δ 9.27-9.21 (m, 2H), 8.23 (s, 1H), 7.95 (dd, J=10.8, 7.4 Hz, 1H), 7.88 (dd, J=10.4, 7.3 Hz, 1H), 7.28-6.95 (m, 1H), 3.77-3.71 (m, 1H), 1.08-1.00 (m, 2H), 0.76-0.68 (m, 2H)

LC-MS: m/z 362.2 [M+H]$^+$ at 2.36 RT (96.77% purity)

HPLC: 96.68%

Chiral HPLC (purity): 100.00%; $R_t$=12.25 min (Chiralpak IA, 250×4.6 mm, 5 μm); mobile phase (A) 0.1% DEA in n-hexane (B) DCM:MeOH (50:50) (A:B::85:15); flow Rate: 1.0 mL/min).

Example 41

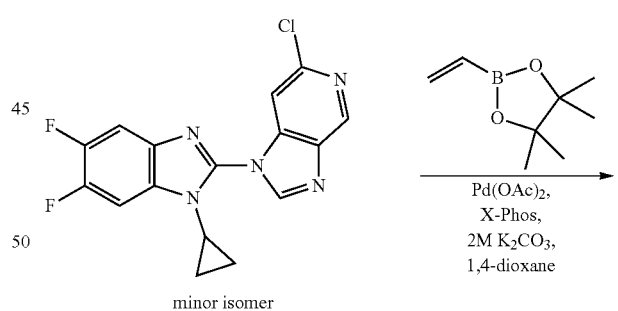

minor isomer

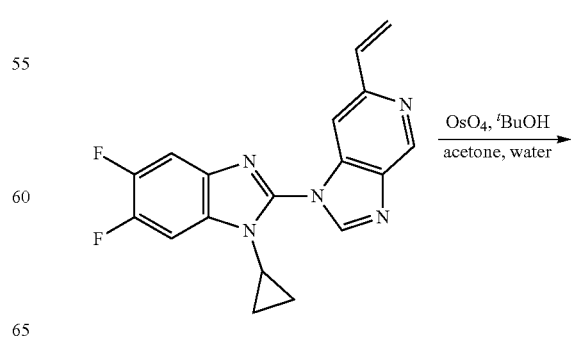

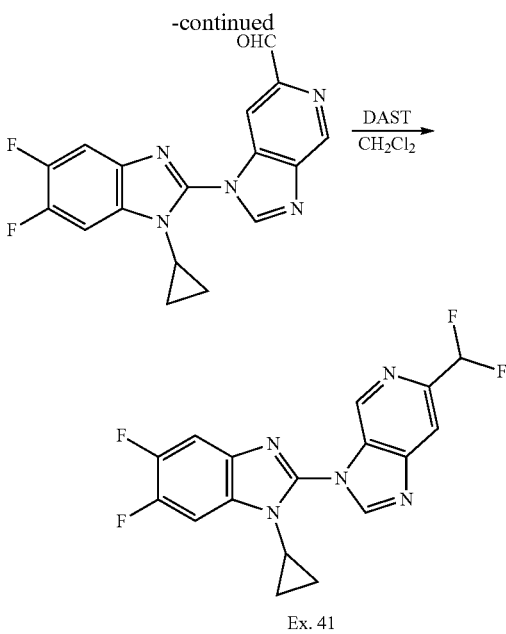

Ex. 41

1-(1-cyclopropyl-5,6-difluoro-1H-benzo[d]imidazol-2-yl)-6-vinyl-1H-imidazo[4,5-c]pyridine To a stirred solution of 6-chloro-1-(1-cyclopropyl-5,6-difluoro-1H-benzo[d]imidazol-2-yl)-1H-imidazo[4,5-c]pyridine (minor isomer) (200 mg, 0.58 mmol) in 1,4-dioxane (5 mL) was added 4,4,5,5-tetramethyl-2-vinyl-1,3,2-dioxaborolane (178 mg, 1.16 mmol) and a solution of aqueous potassium carbonate (2 M, 0.6 mL) in a sealed tube at room temperature and the mixture was purged under argon for 5 min. Pd (OAc)$_2$ (20 mg, 0.03 mmol) and X-Phos (41 mg, 0.09 mmol) were added and the mixture was degassed under argon for 5 min. The reaction mixture was heated to 80° C. and stirred for 16 h. After consumption of starting material (by TLC), the reaction mixture was poured into water (20 mL) and extracted with EtOAc (2×30 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1-(1-cyclopropyl-5,6-difluoro-1H-benzo[d]imidazol-2-yl)-6-vinyl-1H-imidazo[4,5-c]pyridine (120 mg, 0.35 mmol, 61%) as a pale yellow solid.

$^1$H NMR (400 MHz, CDCl$_3$): δ 9.14 (d, J=1.0 Hz, 1H), 8.50 (s, 1H), 7.84 (d, J=0.8 Hz, 1H), 7.61 (dd, J=10.1, 7.2 Hz, 1H), 7.43 (dd, J=9.5, 6.9 Hz, 1H), 6.99 (dd, J=17.3, 10.7 Hz, 1H), 6.26 (dd, J=17.4, 1.3 Hz, 1H), 5.50 (dd, J=10.7, 1.2 Hz, 1H), 3.49-3.44 (m, 1H), 1.16-1.10 (m, 2H), 0.78-0.72 (m, 2H)

LC-MS: m/z 338.1 [M+H]$^+$ at 2.74 RT (96.95% purity)

1-(1-cyclopropyl-5,6-difluoro-1H-benzo[d]imidazol-2-yl)-1H-imidazo[4,5-c]pyridine-6-carbaldehyde To a stirred solution of 1-(1-cyclopropyl-56-difluoro-1H-benzo[d]imidazol-2-yl)-6-vinyl-1H-imidazo[4,5-c]pyridine (120 mg, 0.36 mmol) in tert-butanol/acetone/water (1:1:1, 7.2 mL) was added sodium periodate (152 mg, 0.71 mmol) followed by a solution of osmium tetroxide (1 M in toluene, 2.4 mL) drop wise at 0° C. under an inert atmosphere. The reaction mixture was gradually warmed to room temperature and stirred for 1 h After consumption of starting material (by TLC), the reaction mixture was filtered through a pad of Celite and washed with EtOAC (10 mL). The filtrate was extracted with EtOAc (2×20 mL). The combined organic extracts were dried over anhydrous Na$_2$SO$_4$ and concentrated under reduced pressure to afford 1-(1-cyclopropyl-5,6-difluoro-1H-benzo[d]imidazol-2-yl)-1H-imidazo[4,5-c]pyridine-6-carbaldehyde (120 mg) as a brown solid. The crude material was taken to the next step without further purification.

$^1$H NMR (400 MHz, DMSO-d$_6$): δ 10.15 (s, 1H), 9.41 (d, J=1.0 Hz, 1H), 9.32 (s, 1H), 8.42 (d, J=0.8 Hz, 1H), 7.97-7.87 (m, 2H), 3.80-3.75 (m, 1H), 1.06-1.02 (m, 2H), 0.77-0.71 (m, 2H)

LC-MS: m/z 339.9 [M+H]$^+$ at 2.49 RT (77.00% purity)

3-(1-cyclopropyl-5,6-difluoro-1H-benzo[d]imidazol-2-yl)-6-(difluoromethyl)-3H-imidazo[4,5-c]pyridine (Ex. 41)

To a stirred solution of 1-(1-cyclopropyl-5,6-difluoro-1H-benzo[d]imidazol-2-yl)-1H-imidazo[4,5-c]pyridine-6-carbaldehyde (120 mg, crude) in CH$_2$Cl$_2$ (6 mL) was added diethylaminosulfur trifluoride (0.09 mL, 0.71 mmol) at 0° C. under an inert atmosphere. The reaction mixture was gradually warmed to room temperature and stirred for 90 min. After consumption of starting material (by TLC), the reaction mixture was basified with saturated NaHCO$_3$ solution (100 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 20-30% EtOAc/hexane) to afford 3-(1-cyclopropyl-5,6-difluoro-1H-benzo[d]imidazol-2-yl)-6-(difluoromethyl)-3H-imidazo[4,5-c]pyridine Ex. 41 (55 mg, 0.15 mmol, 43% from two steps) as a pale yellow solid. The structure was further confirmed by 2 D NMR (NOESY, DQFCOSY) studies.

$^1$H NMR (400 MHz, DMSO-d$_6$): δ 9.33-9.25 (m, 2H), 8.19 (s, 1H), 7.95-7.86 (m, 2H), 7.30-6.96 (m, 1H), 3.80-3.74 (m, 1H), 1.08-1.00 (m, 2H), 0.79-0.70 (m, 2H)

LC-MS: m/z 361.9 [M+H]$^+$ at 2.78 RT (97.33% purity)
HPLC: 98.97%
Chiral HPLC (purity): 100.00%; R$_t$=20.73 min (Chiralpak IA, 250×4.6 mm, 5 µm); mobile phase (A) 0.1% DEA in n-hexane (B) DCM:MeOH (50:50) (A:B::85:15); flow Rate: 1.0 mL/min).

Example 42 & Example 43

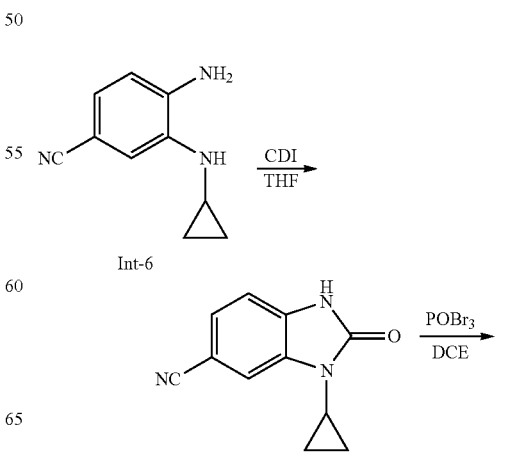

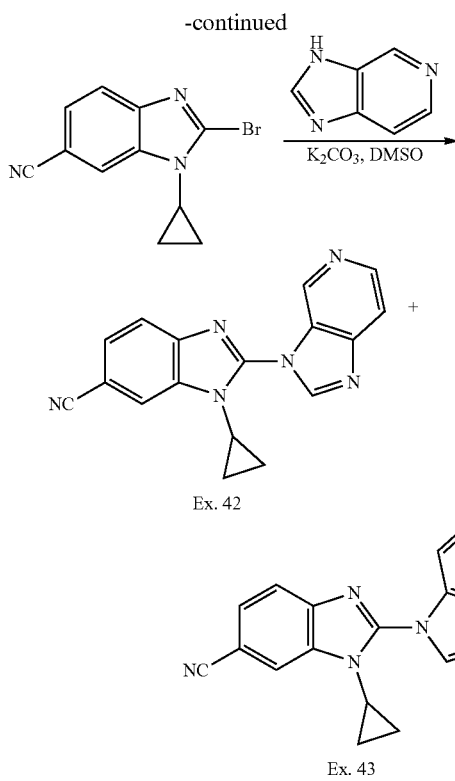

Ex. 42

Ex. 43

3-cyclopropyl-2-oxo-2,3-dihydro-1H-benzo[d]imidazole-5-carbonitrile

To a stirred solution of 4-amino-3-(cyclopropylamino) benzonitrile Int-6 (4 g, 23.12 mmol) in THF (80 mL) was added 1,1'-carbonyldiimidazole (5.62 g, 34.68 mmol) at 0° C. under an inert atmosphere. The reaction mixture was gradually warmed to room temperature and stirred for 16 h. After consumption of starting material (by TLC), the reaction mixture was diluted with EtOAc (50 mL). The combined organic extracts were washed with 1 N HCl solution (20 mL), water (50 mL) and brine (50 mL). The organic layer was separated, dried over anhydrous $Na_2SO_4$ and concentrated under reduced pressure. The crude material was purified by silica gel column chromatography (eluent: 40% EtOAc/hexane) to afford 3-cyclopropyl-2-oxo-2,3-dihydro-1H-benzo[d]imidazole-5-carbonitrile (3.8 g, 19.07 mmol, 83%) as an off-white solid.

$^1$H NMR (400 MHz, DMSO-$d_6$): δ 11.30 (s, 1H), 7.54 (d, J=1.3 Hz, 1H), 7.45 (dd, J=8.1, 1.6 Hz, 1H), 7.08 (dd, J=8.1, 0.4 Hz, 1H), 2.89-2.82 (m, 1H), 1.07-0.98 (m, 2H), 0.92-0.84 (m, 2H)

LC-MS: m/z 200.2 [M+H]$^+$ at 1.73 RT (99.76% purity)

2-bromo-1-cyclopropyl-1H-benzo[d]imidazole-6-carbonitrile

To a stirred solution of 3-cyclopropyl-2-oxo-2,3-dihydro-1H-benzo[d]imidazole-5-carbonitrile (3.8 g, 19.09 mmol) in 1,2-dichloroethane (250 mL) was added phosphoryl bromide (10.95 g, 38.19 mmol) portion wise at 0° C. under an inert atmosphere. The reaction mixture was heated to 95° C. and stirred for 16 h. Then another lot of phosphoryl bromide (5.47 g, 19.09 mmol) was added at 0° C. The reaction mixture was heated to 95° C. and stirred for another 16 h. After consumption of starting material (by TLC), the reaction mixture was poured into ice cold water (50 mL), basified using saturated $NaHCO_3$ solution to pH~8 and extracted with EtOAc (2×100 mL). The combined organic extracts were dried over anhydrous $Na_2SO_4$ and concentrated under reduced pressure. The crude material was purified by silica gel column chromatography (eluent: 20% EtOAc/hexane) to afford 2-bromo-1-cyclopropyl-1H-benzo[d]imidazole-6-carbonitrile (2.8 g, 10.68 mmol, 56%) as an off-white solid.

$^1$H NMR (400 MHz, DMSO-$d_6$): δ 8.18 (dd, J=1.6, 0.6 Hz, 1H), 7.77 (dd, J=8.3, 0.6 Hz, 1H), 7.64 (dd, J=8.3, 1.6 Hz, 1H), 3.45-3.38 (m, 1H), 1.32-1.26 (m, 2H), 1.16-1.12 (m, 2H)

LC-MS: m/z 261.7 [M+H]$^+$ at 2.52 RT (95.12% purity)

1-cyclopropyl-2-(3H-imidazo[4,5-c]pyridin-3-yl)-1H-benzo[d]imidazole-6-carbonitrile (Ex. 42) & 1-cyclopropyl-2-(1H-imidazo[4,5-c]pyridin-1-yl)-1H-benzo[d]imidazole-6-carbonitrile (Ex. 43)

To a stirred solution of 2-bromo-1-cyclopropyl-1H-benzo[d]imidazole-6-carbonitrile (225 mg, 0.86 mmol) in DMSO (2.5 mL) was added 3H-imidazo[4,5-c]pyridine (102 mg, 0.86 mmol) and potassium carbonate (355 mg, 2.58 mmol) at room temperature under an inert atmosphere. The reaction mixture was heated to 80° C. and stirred for 16 h. After consumption of starting material (by TLC), the reaction mixture was diluted with ice cold water (50 mL) and extracted with EtOAc (2×20 mL). The combined organic extracts were dried over anhydrous $Na_2SO_4$ and concentrated under reduced pressure. The crude material was purified by silica gel column chromatography (eluent: 5% MeOH/$CH_2Cl_2$) followed by chiral preparative HPLC to afford 1-cyclopropyl-2-(3H-imidazo[4,5-c]pyridin-3-yl)-1H-benzo[d]imidazole-6-carbonitrile Ex. 42 (25 mg, 0.08 mmol, 10%) & 1-cyclopropyl-2-(1H-imidazo[4,5-c]pyridin-1-yl)-1H-benzo[d]imidazole-6-carbonitrile Ex. 43 (55 mg, 0.18 mmol, 21%) as off white solids respectively. The structures were confirmed by 2 D NMR (NOESY, DQF-COSY).

Analytical Data of Ex. 42:

$^1$H NMR (400 MHz, DMSO-$d_6$): δ 9.32 (d, J=0.9 Hz, 1H), 9.23 (s, 1H), 8.55 (d, J=5.5 Hz, 1H), 8.31 (d, J=1.0 Hz, 1H), 7.95 (d, J=8.3 Hz, 1H), 7.89 (dd, J=5.5, 0.9 Hz, 1H), 7.76 (dd, J=8.4, 1.5 Hz, 1H), 3.88-3.81 (m, 1H), 1.15-1.09 (m, 2H), 0.83-0.77 (m, 2H)

LC-MS: m/z 300.9 [M+H]$^+$ at 2.13 RT (99.85% purity)

HPLC: 99.77%

Chiral HPLC (purity): 95.01%; $R_t$=10.29 min (Chiralpak IA, 250×4.6 mm, 5 μm); mobile phase (A) 0.1% DEA in n-hexane (B) DCM:MeOH (50:50) (A:B: 75:25); flow Rate: 1.0 mL/min).

Analytical Data of Ex. 43:

$^1$H NMR (400 MHz, DMSO-$d_6$): δ 9.16 (d, J=1.0 Hz, 1H), 9.12 (s, 1H), 8.55 (d, J=5.5 Hz, 1H), 8.32 (dd, J=1.5, 0.6 Hz, 1H), 7.98 (dd, J=5.6, 1.1 Hz, 1H), 7.94 (dd, J=8.4, 0.6 Hz, 1H), 7.76 (dd, J=8.4, 1.6 Hz, 1H), 3.84-3.78 (m, 1H), 1.12-1.06 (m, 2H), 0.79-0.74 (m, 2H)

LC-MS: m/z 300.9 [M+H]$^+$ at 2.15 RT (99.84% purity)

HPLC: 99.68%

Chiral HPLC (purity): 100.00%; $R_t$=9.10 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min)

Example 44 & Example 51

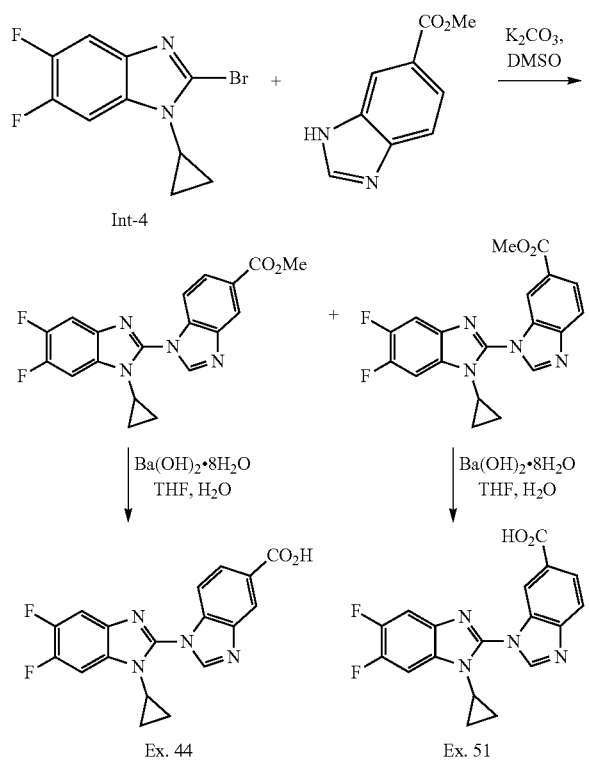

methyl 1'-cyclopropyl-5',6'-difluoro-1'H-[1,2'-bibenzo[d]imidazole]-5-carboxylate & methyl 1'-cyclopropyl-5',6'-difluoro-1'H-[1,2'-bibenzo[d]imidazole]-6-carboxylate To a stirred solution of 2-bromo-1-cyclopropyl-5,6-difluoro-1H-benzo[d]imidazole Int-4 (500 mg, 1.83 mmol) in DMSO (5 mL) was added methyl 1H-benzo[d]imidazole-6-carboxylate (323 mg, 1.83 mmol) and potassium carbonate (654 mg, 5.49 mmol) at room temperature under an inert atmosphere. The reaction mixture was heated to 80° C. and stirred for 16 h. After consumption of starting material (by TLC), the reaction mixture was diluted with water (70 mL) and extracted with EtOAc (2×30 mL). The combined organic extracts were dried over anhydrous $Na_2SO_4$ and concentrated under reduced pressure. The crude material was purified by silica gel column chromatography (eluent: 5% MeOH/$CH_2Cl_2$) followed by chiral preparative HPLC to afford methyl 1'-cyclopropyl-5',6'-difluoro-1'H-[1,2'-bibenzo[d]imidazole]-5-carboxylate (200 mg, 0.54 mmol, 30%) & methyl 1'-cyclopropyl-5',6'-difluoro-1'H-[1,2'-bibenzo[d]imidazole]-6-carboxylate (200 mg, 0.54 mmol, 30%) as off white solids respectively. The structures were confirmed by 2 D NMR (NOESY, DQFCOSY) studies.

Analytical Data of methyl 1'-cyclopropyl-5',6'-difluoro-1'H-[1,2'-bibenzo[d]imidazole]-5-carboxylate $^1$H NMR (500 MHz, DMSO-$d_6$): δ 9.07 (s, 1H), 8.40 (d, J=0.9 Hz, 1H), 8.06-8.03 (m, 1H), 7.99-7.96 (m, 1H), 7.92-7.84 (m, 2H), 3.91 (s, 3H), 3.75-3.70 (m, 1H), 1.04-0.99 (m, 2H), 0.69-0.65 (m, 2H)

LC-MS: m/z 369.0 [M+H]$^+$ at 2.98 RT (99.80% purity)
HPLC: 99.18%
Chiral HPLC (purity): 100.00%; $R_t$=11.09 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min

Analytical Data of methyl 1'-cyclopropyl-5',6'-difluoro-1'H-[1,2'-bibenzo[d]imidazole]-6-carboxylate $^1$H NMR (500 MHz, DMSO-$d_6$): δ 9.15 (s, 1H), 8.49 (s, 1H), 8.02-7.99 (m, 1H), 7.98-7.93 (m, 2H), 7.86 (dd, J=10.3, 7.3 Hz, 1H), 3.88 (s, 3H), 3.76-3.71 (m, 1H), 1.04-1.01 (m, 2H), 0.70-0.65 (m, 2H)
LC-MS: m/z 369.0 [M+H]$^+$ at 2.97 RT (96.73% purity)
HPLC: 99.00%
Chiral HPLC (purity): 100.00%; $R_t$=6.11 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min

1'-cyclopropyl-5',6'-difluoro-1'H-[1,2'-bibenzo[d]imidazole]-5-carboxylic acid (Ex. 44)

To a stirred solution of methyl 1'-cyclopropyl-5',6'-difluoro-1'H-[1,2'-bibenzo[d]imidazole]-5-carboxylate (50 mg, 0.13 mmol) in a mixture of THF (1 mL) and water (0.5 mL) was added barium hydroxide octahydrate (128 mg, 0.41 mmol) at room temperature and the mixture was stirred for 16 h. After consumption of starting material (by TLC), the reaction mixture was quenched with dry ice. The obtained solid was filtered and the filtrate was concentrated under reduced pressure. The crude material was triturated with $CH_2Cl_2$ (2×3 mL), n-pentane (2×10 mL) and lyophilized to afford 1'-cyclopropyl-5',6'-difluoro-1'H-[1,2'-bibenzo[d]imidazole]-5-carboxylic acid Ex. 44 (35 mg, 0.1 mmol, 73%) as an off white solid.

$^1$H NMR (400 MHz, DMSO-$d_6$): δ 9.01 (s, 1H), 8.36 (d, J=0.9 Hz, 1H), 8.02 (dd, J=8.6, 1.4 Hz, 1H), 7.92-7.82 (m, 3H), 3.75-3.70 (m, 1H), 1.04-0.98 (m, 2H), 0.69-0.64 (m, 2H)
LC-MS: m/z 355.2 [M+H]$^+$ at 2.16 RT (98.43% purity)
HPLC: 98.50%

1'-cyclopropyl-5',6'-difluoro-1'H-[1,2'-bibenzo[d]imidazole]-6-carboxylic acid (Ex. 51)

To a stirred solution of methyl 1'-cyclopropyl-5',6'-difluoro-1'H-[1,2'-bibenzo[d]imidazole]-6-carboxylate (160 mg, 0.43 mmol) in a mixture of THF (3 mL) and water (1.5 mL) was added barium hydroxide octahydrate (411 mg, 1.3 mmol) at room temperature and the mixture was stirred for 24 h. Then another lot of barium hydroxide octahydrate (411 mg, 1.3 mmol) was added at room temperature and stirred for another 24 h. After consumption of starting material (by TLC), the reaction mixture was quenched with dry ice. The reaction mixture was filtered through a pad of celite and the celite bed was washed with THF/water/methanol (1:1:1, 12 mL). The filtrate was concentrated under reduced pressure. The crude material was lyophilized and again triturated with 2% MeOH/$CH_2Cl_2$ (6 mL) to afford 1'-cyclopropyl-5',6'-difluoro-1'H-[1,2'-bibenzo[d]imidazole]-6-carboxylic acid Ex. 51 (28 mg, 0.08 mmol, 19%) as an off white solid.

$^1$H NMR (400 MHz, DMSO-$d_6$): δ 13.05 (brs, 1H), 9.13 (s, 1H), 8.48 (d, J=1.0 Hz, 1H), 8.01-7.94 (m, 2H), 7.93-7.82 (m, 2H), 3.76-3.71 (m, 1H), 1.07-1.01 (m, 2H), 0.71-0.64 (m, 2H)

LC-MS: m/z 355.2 [M+H]⁺ at 2.13 RT (94.55% purity)
HPLC: 93.56%

Example 45 & Example 46

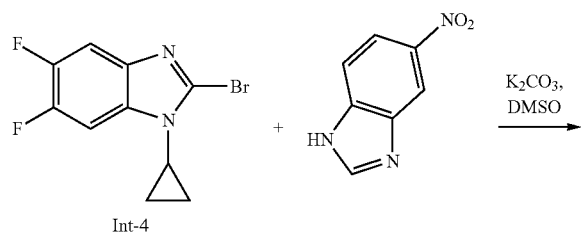

Int-4

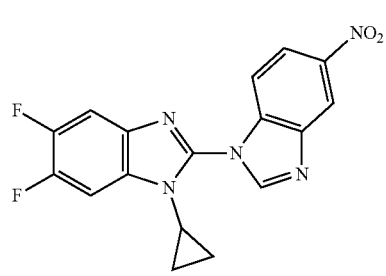

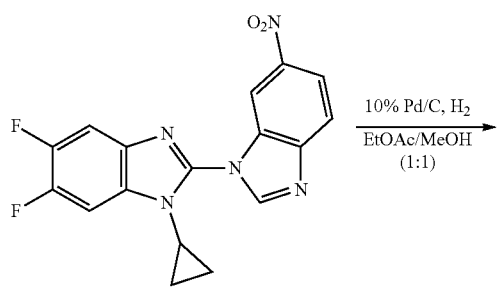

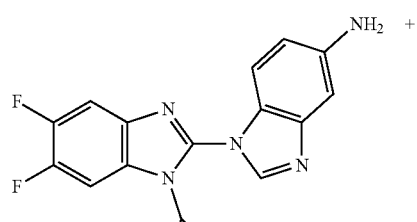

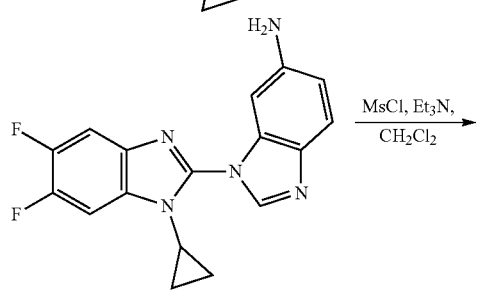

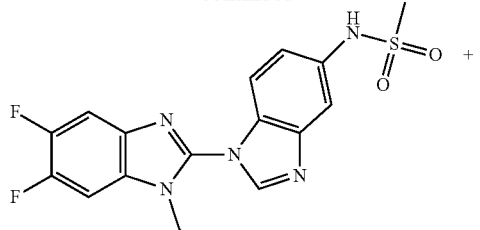

Ex. 46

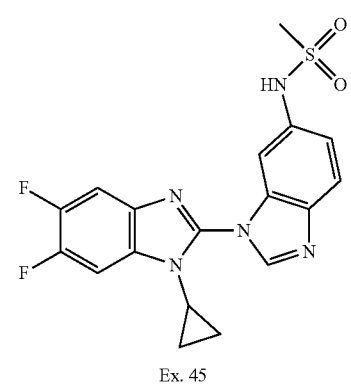 [SMILES: CS(=O)(=O)Nc1ccc2ncn(-c3nc4cc(F)c(F)cc4n3C3CC3)c2c1]

Ex. 45

1'-cyclopropyl-5',6'-difluoro-5-nitro-1'H-1,2'-bibenzo[d]imidazole

To a stirred solution of 2-bromo-1-cyclopropyl-5,6-difluoro-1H-benzo[d]imidazole Int-4 (500 mg, 1.84 mmol) in DMSO (5 mL) was added 5-nitro-1H-benzo[d]imidazole (451 mg, 2.77 mmol) and potassium carbonate (764 mg, 5.53 mmol) at room temperature under an inert atmosphere. The reaction mixture was heated to 100° C. and stirred for 16 h. After consumption of starting material (by TLC), the reaction mixture was poured into ice cold water (60 mL). The obtained solid was filtered. The residue was purified by silica gel column chromatography (eluent: 20% EtOAc/hexane) to afford 1'-cyclopropyl-5',6'-difluoro-5-nitro-1'H-1,2'-bibenzo[d]imidazole (620 mg, mixture of isomers) as a pale yellow solid. The mixture was taken to the next step without further purification.

1'-cyclopropyl-5',6'-difluoro-1'H-[1,2'-bibenzo[d]imidazol]-5-amine

To a stirred solution of 1'-cyclopropyl-5',6'-difluoro-5-nitro-1'H-1,2'-bibenzo[d]imidazole (100 mg, mixture) in a mixture of ethylacetate/methanol (1:1, 20 mL) was added 10% Pd/C (50% wet, 25 mg) at room temperature under an inert atmosphere. The reaction mixture was stirred at room temperature under hydrogen atmosphere (balloon pressure) for 4 h. After consumption of starting material (by TLC), the reaction mixture was filtered through a pad of celite and the celite bed was washed with methanol (20 mL). The filtrate was concentrated under reduced pressure to afford 1'-cyclopropyl-5',6'-difluoro-1'H-[1,2'-bibenzo[d]imidazol]-5-amine and regioisomer (60 mg, mixture of isomers) as brown syrup. The crude material was taken to the next step without further purification.
LC-MS: m/z 326.0 [M+H]⁺ at 2.36 RT (88.53% purity)

N-(1'-cyclopropyl-5',6'-difluoro-1'H-[1,2'-bibenzo[d]imidazol]-5-yl) methanesulfonamide (Ex. 46) &
N-(1'-cyclopropyl-5',6'-difluoro-1'H-[1,2'-bibenzo[d]imidazol]-6-yl) methanesulfonamide (Ex. 45)

To a stirred solution of 1'-cyclopropyl-5',6'-difluoro-1'H-[1,2'-bibenzo[d]imidazol]-5-amine and regioisomer (300 mg, crude) in CH$_2$Cl$_2$ (30 mL) was added triethylamine (0.13 mL, 0.92 mmol) followed by methanesulfonyl chloride (0.06 mL, 0.74 mmol) at 0° C. under an inert atmosphere and stirred at 0° C. for 1 h. After consumption of starting material (by TLC), the reaction mixture was quenched using saturated NaHCO$_3$ solution (20 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 30% MeOH/CH$_2$Cl$_2$) followed by chiral preparative HPLC to afford Ex. 46 (42 mg, 0.1 mmol) & Ex. 45 (31 mg, 0.08 mmol) as pale yellow solids respectively. The structures were confirmed by 2 D NMR (NOESY, gDQFCOSY) studies.

Analytical Data of Ex. 46:

$^1$H NMR (500 MHz, DMSO-d$_6$): δ 9.72 (s, 1H), 8.91 (s, 1H), 7.90-7.80 (m, 3H), 7.67 (d, J=1.8 Hz, 1H), 7.29 (dd, J=8.7, 1.8 Hz, 1H), 3.74-3.69 (m, 1H), 2.99 (s, 3H), 1.06-0.99 (m, 2H), 0.69-0.61 (m, 2H)

LC-MS: m/z 404.0 [M+H]$^+$ at 2.51 RT (99.13% purity)

HPLC: 98.74%

Chiral HPLC (purity): 100.00%; R$_t$=14.73 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min)

Analytical Data of Ex. 45:

$^1$H NMR (500 MHz, DMSO-d$_6$): δ 9.77 (s, 1H), 8.87 (s, 1H), 7.90-7.83 (m, 2H), 7.79 (d, J=8.3 Hz, 1H), 7.74 (d, J=1.8 Hz, 1H), 7.27 (dd, J=8.7, 1.8 Hz, 1H), 3.73-3.66 (m, 1H), 2.95 (s, 3H), 1.05-0.98 (m, 2H), 0.69-0.65 (m, 2H)

LC-MS: m/z 403.9 [M+H]$^+$ at 2.46 RT (96.45% purity)

HPLC: 96.12%

Chiral HPLC (purity): 100.00%; R$_t$=7.82 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min)

Example 47 & Example 48

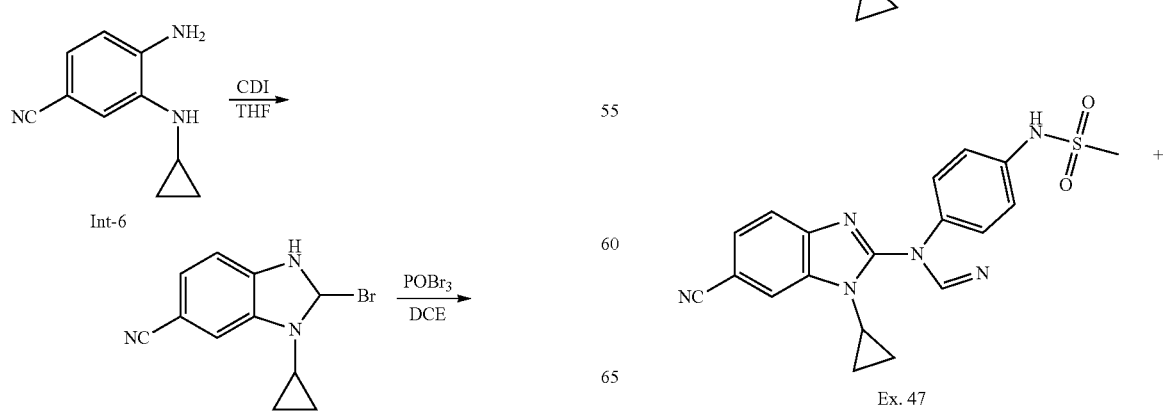

Ex. 47

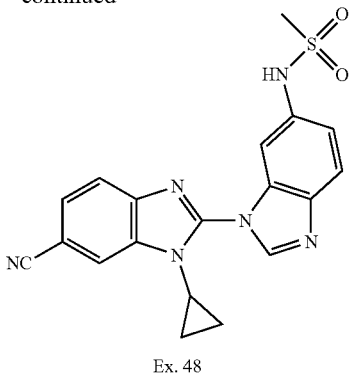

Ex. 48

3-cyclopropyl-2-oxo-2,3-dihydro-1H-benzo[d]imidazole-5-carbonitrile

To a stirred solution of 4-amino-3-(cyclopropylamino) benzonitrile Int-6 (4 g, 23.12 mmol) in THF (80 mL) was added 1,1'-carbonyldiimidazole (5.62 g, 34.68 mmol) at 0° C. under an inert atmosphere. The reaction mixture was gradually warmed to room temperature and stirred for 16 h. After consumption of starting material (by TLC), the reaction mixture was diluted with EtOAc (50 mL). The combined organic extracts were washed with 1 N HCl solution (20 mL), water (50 mL) and brine (50 mL). The organic layer was separated, dried over anhydrous $Na_2SO_4$ and concentrated under reduced pressure. The crude material was purified by silica gel column chromatography (eluent: 40% EtOAc/hexane) to afford 3-cyclopropyl-2-oxo-2,3-dihydro-1H-benzo[d]imidazole-5-carbonitrile (3.8 g, 19.07 mmol, 83%) as an off-white solid.

$^1$H NMR (400 MHz, DMSO-$d_6$): δ 11.30 (s, 1H), 7.54 (d, J=1.3 Hz, 1H), 7.45 (dd, J=8.1, 1.6 Hz, 1H), 7.08 (dd, J=8.1, 0.4 Hz, 1H), 2.89-2.82 (m, 1H), 1.07-0.98 (m, 2H), 0.92-0.84 (m, 2H)

LC-MS: m/z 200.2 [M+H]$^+$ at 1.73 RT (99.76% purity)

2-bromo-1-cyclopropyl-1H-benzo[d]imidazole-6-carbonitrile

To a stirred solution of 3-cyclopropyl-2-oxo-2,3-dihydro-1H-benzo[d]imidazole-5-carbonitrile (3.8 g, 19.09 mmol) in 1,2-dichloroethane (250 mL) was added phosphoryl bromide (10.95 g, 38.19 mmol) portion wise at 0° C. under an inert atmosphere. The reaction mixture was heated to 95° C. and stirred for 16 h. Then another lot of phosphoryl bromide (5.47 g, 19.09 mmol) was added at 0° C. The reaction mixture was heated to 95° C. and stirred for another 16 h. After consumption of starting material (by TLC), the reaction mixture was poured into ice cold water (50 mL), basified with saturated NaHCO$_3$ solution to pH~8 and extracted with EtOAc (2×100 mL). The combined organic extracts were dried over anhydrous Na$_2$SO$_4$ and concentrated under reduced pressure. The crude material was purified by silica gel column chromatography (eluent: 20% EtOAc/hexane) to afford 2-bromo-1-cyclopropyl-1H-benzo[d]imidazole-6-carbonitrite (2.8 g, 10.68 mmol, 56%) as an off-white solid.

$^1$H NMR (400 MHz, DMSO-$d_6$): δ 8.18 (dd, J=1.6, 0.6 Hz, 1H), 7.77 (dd, J=8.3, 0.6 Hz, 1H), 7.64 (dd, J=8.3, 1.6 Hz, 1H), 3.45-3.38 (m, 1H), 1.32-1.26 (m, 2H), 1.16-1.12 (m, 2H)

LC-MS: m/z 261.7 [M+H]$^+$ at 2.52 RT (95.12% purity)

1'-cyclopropyl-5-nitro-1'H-[1,2'-bibenzo[d]imidazole]-6'-carbonitrile

To a stirred solution of 2-bromo-1-cyclopropyl-1H-benzo[d]imidazole-6-carbonitrile (1 g, 3.82 mmol) in DMSO (10 mL) was added 5-nitro-1H-benzo[d]imidazole (622 mg, 3.82 mmol) and potassium carbonate (1.58 g, 11.45 mmol) at room temperature under an inert atmosphere. The reaction mixture was heated to 90° C. and stirred for 16 h. After consumption of starting material (by TLC), the reaction mixture was poured into ice cold water (30 mL) and extracted with EtOAc (2×40 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 1'-cyclopropyl-5-nitro-1'H-[1,2'-bibenzo[d]imidazole]-6'-carbonitrile and regioisomer (550 mg, mixture of isomers) as a pale yellow solid.

LC-MS: m/z 345.0 [M+H]$^+$ at 2.84 RT (85.04% purity)

5-amino-1'-cyclopropyl-1'H-[1,2'-bibenzo[d]imidazole]-6'-carbonitrile

To a stirred solution of 1'-cyclopropyl-5-nitro-1'H-[1,2'-bibenzo[d]imidazole]-6'-carbonitrile (450 mg, 1.31 mmol) in a mixture of ethylacetate (80 mL) and methanol (80 mL) was added 10% Pd/C (50% wet, 112 mg) at room temperature under an inert atmosphere. The reaction mixture was stirred at room temperature under hydrogen atmosphere (balloon pressure) for 2 h. After consumption of starting material (by TLC), the reaction mixture was filtered through a pad of Celite and washed with EtOAc (100 mL). The filtrate was concentrated under reduced pressure to afford 5-amino-1'-cyclopropyl-1'H-[1,2'-bibenzo[d]imidazole]-6'-carbonitrile and regioisomer (400 mg) as a pale brown solid. The crude material was taken to the next step without further purification.

LC-MS: m/z 315.0 [M+H]$^+$ at 2.12 RT (58.42% purity)

N-(6'-cyano-1'-cyclopropyl-1'H-[1,2'-bibenzo[d]imidazol]-5-yl) methanesulfonamide (Ex. 47) & N-(6'-cyano-1'-cyclopropyl-1'H-[1,2'-bibenzo[d]imidazol]-6-yl) methanesulfonamide (Ex. 48)

To a stirred solution of 5-amino-1'-cyclopropyl-1'H-[1,2'-bibenzo[d]imidazole]-6'-carbonitrile and regioisomer (400 mg, crude) in CH$_2$Cl$_2$ (10 mL) was added triethylamine (0.27 mL, 1.91 mmol) followed by a solution of methanesulfonyl chloride (0.07 mL, 0.95 mmol) in CH$_2$Cl$_2$ (2 mL) drop wise at 0° C. under an inert atmosphere and stirred at 0° C. for 30 min. After consumption of starting material (by TLC), the reaction mixture was quenched using saturated NaHCO$_3$ solution (30 mL) and extracted with CH$_2$Cl$_2$ (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) followed by chiral preparative HPLC to afford N-(6'-cyano-1'-cyclopropyl-1'H-[1,2'-bibenzo[d]imidazol]-5-yl) methanesulfonamide Ex. 47 (110 mg, 0.28 mmol) & N-(6'-cyano-1'-cyclopropyl-1'H-[1,2'-bibenzo[d]imidazol]-6-yl) methanesulfonamide Ex. 48 (50 mg, 0.13 mmol) as yellow solids respectively. The structures were confirmed by 2 D NMR (NOESY, DQF-COSY) studies.

Analytical Data of Ex. 47:

$^1$H NMR (400 MHz, DMSO-$d_6$): δ 9.73 (brs, 1H), 8.99 (s, 1H), 8.28 (d, J=1.0 Hz, 1H), 7.95-7.89 (m, 2H), 7.73 (dd, J=8.3, 1.4 Hz, 1H), 7.68 (d, J=1.9 Hz, 1H), 7.31 (dd, J=8.7, 1.9 Hz, 1H), 3.84-3.77 (m, 1H), 2.99 (s, 3H), 1.14-1.07 (m, 2H), 0.77-0.71 (m, 2H)

LC-MS: m/z 393.0 [M+H]$^+$ at 2.30 RT (96.63% purity)

HPLC: 95.50%

Chiral HPLC (purity): 98.00%; R$_t$=18.80 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min)

Analytical Data of Ex. 48:

$^1$H NMR (400 MHz, DMSO-$d_6$): δ 9.80 (s, 1H), 8.94 (s, 1H), 8.29 (d, J=0.8 Hz, 1H), 7.93-7.86 (m, 2H), 7.80 (d, J=8.7 Hz, 1H), 7.74 (dd, J=8.3, 1.4 Hz, 1H), 7.29 (dd, J=8.7, 2.0 Hz, 1H), 3.83-3.75 (m, 1H), 2.96 (s, 3H), 1.14-1.07 (m, 2H), 0.79-0.72 (m, 2H)

LC-MS: m/z 393.1 [M+H]$^+$ at 2.26 RT (99.05% purity)

HPLC: 97.73%

Chiral HPLC (purity): 100.00%; R$_t$=11.19 min (Chiralpak IA, 250×4.6 mm, 5 μm); mobile phase (A) 0.1% DEA in n-hexane (B) DCM:MeOH (50:50) (A:B::75:25); flow Rate: 1.0 mL/min)

Example 49 & Example 50

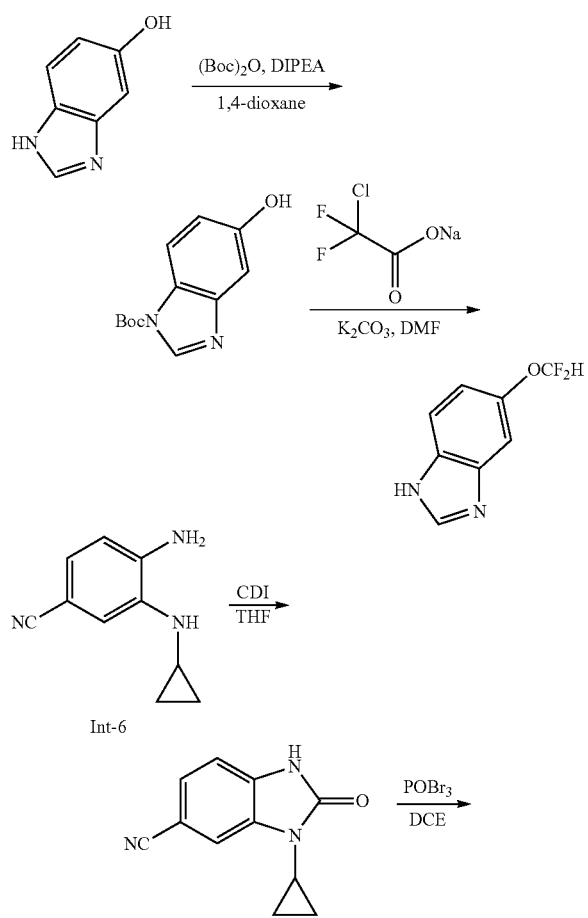

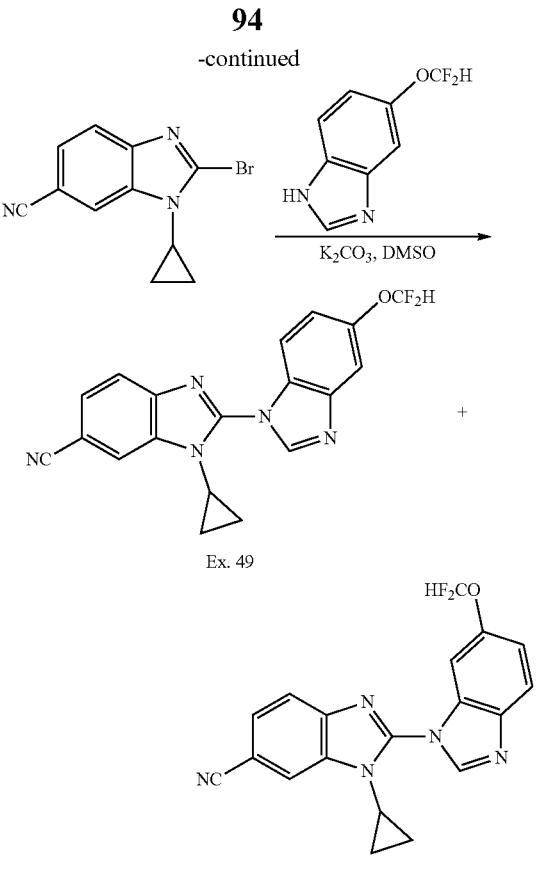

tert-butyl 5-hydroxy-1H-benzo[d]imidazole-1-carboxylate

To a stirred solution of 1H-benzo[d]imidazol-5-ol (1 g, 7.46 mmol) in 1,4-dioxane (30 mL) was added ethyldiisopropylamine (1.43 mL, 8.21 mmol) and di-tert-butyl dicarbonate (1.88 mL, 8.21 mmol) at room temperature under an inert atmosphere. The reaction mixture was heated to 80° C. and stirred for 1 h. After consumption of starting material (by TLC), the reaction mixture was concentrated under reduced pressure. The crude material was purified by silica gel column chromatography (eluent: 1% MeOH/CH$_2$Cl$_2$) to afford tert-butyl 5-hydroxy-1H-benzo[d]imidazole-1-carboxylate (1 g, 4.27 mmol, 57%) as a colorless syrup.

$^1$H NMR (400 MHz, DMSO-$d_6$): δ 9.68-9.37 (m, 1H), 8.54-8.37 (m, 1H), 7.75-7.46 (m, 1H), 7.37-7.02 (m, 1H), 6.91-6.77 (m, 1H), 1.65-1.62 (m, 9H)

LC-MS: m/z 232.9 [M–H]$^-$ at 2.31 RT (56.96% purity)

5-(difluoromethoxy)-1H-benzo[d]imidazole

To a stirred solution of tert-butyl 5-hydroxy-1H-benzo[d]imidazole-1-carboxylate (1.2 g, 5.13 mmol) in DMF (48 mL) was added sodium 2-chloro-2,2-difluoroacetate (1.56 g, 10.26 mmol) and potassium carbonate (2.12 g, 15.38 mmol) at room temperature under an inert atmosphere. The reaction mixture was heated to 100° C. and stirred for 20 h. After consumption of starting material (by TLC), the reaction mixture was poured into ice cold water (100 mL) and extracted with EtOAc (2×40 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) to afford 5-(difluoromethoxy)-1H-benzo[d] imidazole (100 mg, 0.35 mmol, 11%) as a pale brown semi solid.

LC-MS: m/z 184.9 [M+H]$^+$ at 1.87 RT (53.46% purity)

3-cyclopropyl-2-oxo-2,3-dihydro-1H-benzo[d]imidazole-5-carbonitrile

To a stirred solution of 4-amino-3-(cyclopropylamino) benzonitrile Int-6 (4 g, 23.12 mmol) in THF (80 mL) was added 1,1'-carbonyldiimidazole (5.62 g, 34.68 mmol) at 0° C. under an inert atmosphere. The reaction mixture was gradually warmed to room temperature and stirred for 16 h. After consumption of starting material (by TLC), the reaction mixture was diluted with EtOAc (50 mL). The combined organic extracts were washed with 1 N HCl solution (20 mL), water (50 mL) and brine (50 mL). The organic layer was separated, dried over anhydrous Na$_2$SO$_4$ and concentrated under reduced pressure. The crude material was purified by silica gel column chromatography (eluent: 40% EtOAc/hexane) to afford 3-cyclopropyl-2-oxo-2,3-dihydro-1H-benzo[d]imidazole-5-carbonitrile (3.8 g, 19.07 mmol, 83%) as an off-white solid.

$^1$H NMR (400 MHz, DMSO-d$_6$): δ 11.30 (s, 1H), 7.54 (d, J=1.3 Hz, 1H), 7.45 (dd, J=8.1, 1.6 Hz, 1H), 7.08 (dd, J=8.1, 0.4 Hz, 1H), 2.89-2.82 (m, 1H), 1.07-0.98 (m, 2H), 0.92-0.84 (m, 2H)

LC-MS: m/z 200.2 [M+H]$^+$ at 1.73 RT (99.76% purity)

2-bromo-1-cyclopropyl-1H-benzo[d]imidazole-6-carbonitrile

To a stirred solution of 3-cyclopropyl-2-oxo-2,3-dihydro-1H-benzo[d]imidazole-5-carbonitrile (3.8 g, 19.09 mmol) in 1,2-dichloroethane (250 mL) was added phosphoryl bromide (10.95 g, 38.19 mmol) portion wise at 0° C. under an inert atmosphere. The reaction mixture was heated to 95° C. and stirred for 16 h. Then another lot of phosphoryl bromide (5.47 g, 19.09 mmol) was added at 0° C. The reaction mixture was heated to 95° C. and stirred for another 16 h. After consumption of starting material (by TLC), the reaction mixture was poured into ice cold water (50 mL), basified using saturated NaHCO$_3$ solution to pH~8 and extracted with EtOAc (2×100 mL). The combined organic extracts were dried over anhydrous Na$_2$SO$_4$ and concentrated under reduced pressure. The crude material was purified by silica gel column chromatography (eluent: 20% EtOAc/hexane) to afford 2-bromo-1-cyclopropyl-1H-benzo [d]imidazole-6-carbonitrile (2.8 g, 10.68 mmol, 56%) as an off-white solid.

$^1$H NMR (400 MHz, DMSO-d$_6$): δ 8.18 (dd, J=1.6, 0.6 Hz, 1H), 7.77 (dd, J=8.3, 0.6 Hz, 1H), 7.64 (dd, J=8.3, 1.6 Hz, 1H), 3.45-3.38 (m, 1H), 1.32-1.26 (m, 2H), 1.16-1.12 (m, 2H)

LC-MS: m/z 261.7 [M+H]$^+$ at 2.52 RT (95.12% purity)

1'-cyclopropyl-5-(difluoromethoxy)-1'H-[1,2'-bibenzo[d]imidazole]-6'-carbonitrile (Ex. 49) & 1'-cyclopropyl-6-(difluoromethoxy)-1'H-[1,2'-bibenzo[d]imidazole]-6'-carbonitrile (Ex. 50)

To a stirred solution of 5-(difluoromethoxy)-1H-benzo[d] imidazole (150 mg, 0.57 mmol) in DMS0 (1.5 mL) was added 2-bromo-1-cyclopropyl-1H-benzo[d]imidazole-6-carbonitrile (105 mg, 0.57 mmol) and potassium carbonate (237 mg, 1.72 mmol) at room temperature under an inert atmosphere. The reaction mixture was heated to 100° C. and stirred for 16 h. After consumption of starting material (by TLC), the reaction mixture was poured into ice cold water (20 mL) and extracted with EtOAc (2×20 mL). The combined organic extracts were dried over anhydrous Na$_2$SO$_4$ and concentrated under reduced pressure. The crude material was purified by silica gel column chromatography (eluent: 2% MeOH/CH$_2$Cl$_2$) followed by chiral preparative HPLC to afford 1'-cyclopropyl-5-(difluoromethoxy)-1'H-[1, 2'-bibenzo[d]imidazole]-6'-carbonitrile Ex. 49 (25 mg, 0.07 mmol) & 1'-cyclopropyl-6-(difluoromethoxy)-1'H-[1,2'-bibenzo[d]imidazole]-6'-carbonitrile Ex. 50 (25 mg, 0.07 mmol) as off white solids respectively. The two structures were confirmed by 2 D NMR (NOESY, DQFCOSY) studies.

Analytical Data of Ex. 49:

$^1$H NMR (400 MHz, CDCl$_3$): δ 8.54 (s, 1H), 7.98-7.92 (m, 2H), 7.87 (d, J=7.9 Hz, 1H), 7.69 (d, J=2.0 Hz, 1H), 7.65 (dd, J=8.3, 1.5 Hz, 1H), 7.29 (d, J=2.1 Hz, 1H), 6.78-6.39 (m, 1H), 3.58-3.50 (m, 1H), 1.29-1.22 (m, 2H), 0.84-0.78 (m, 2H)

LC-MS: m/z 366.2 [M+H]$^+$ at 2.42 RT (99.51% purity)

HPLC: 98.15%

Chiral HPLC (purity): 100.00%; R$_t$=12.05 min (Chiralpak IA, 250×4.6 mm, 5 μm); mobile phase (A) 0.1% DEA in n-hexane (B) DCM:MeOH (50:50) (A:B::80:20); flow Rate: 1.0 mL/min)

Analytical Data of Ex. 50:

$^1$H NMR (400 MHz, CDCl$_3$): δ 8.51 (s, 1H), 7.96 (dd, J=1.5, 0.8 Hz, 1H), 7.90-7.89 (m, 1H), 7.88-7.87 (m, 1H), 7.76 (d, J=2.0 Hz, 1H), 7.65 (dd, J=8.3, 1.6 Hz, 1H), 7.27-7.23 (m, 1H), 6.78-6.39 (m, 1H), 3.57-3.50 (m, 1H), 1.28-1.22 (m, 2H), 0.84-0.78 (m, 2H)

LC-MS: m/z 366.2 [M+H]$^+$ at 2.41 RT (99.66% purity)

HPLC: 99.16%

Chiral HPLC (purity): 100.00%; R$_t$=9.80 min (Chiralpak IA, 250×4.6 mm, 5 μm); mobile phase (A) 0.1% DEA in n-hexane (B) DCM:MeOH (50:50) (A:B::80:20); flow Rate: 1.0 mL/min)

Example 52 & Example 53

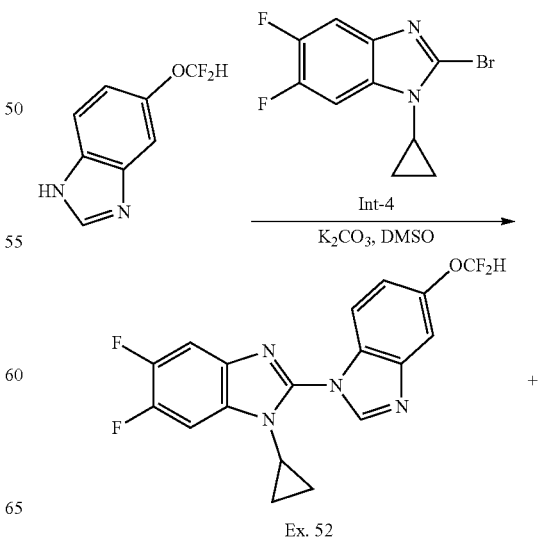

Ex. 52

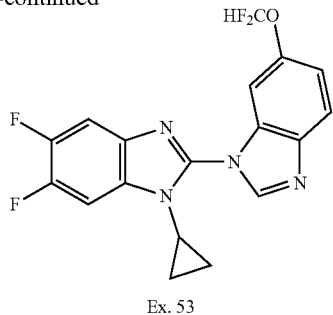

Ex. 53

1'-cyclopropyl-5-(difluoromethoxy)-5',6'-difluoro-1'H-1,2'-bibenzo[d]imidazole (Ex. 52) & 1'-cyclopropyl-6-(difluoromethoxy)-5',6'-difluoro-1'H-1,2'-bibenzo[d]imidazole (Ex. 53)

To a stirred solution of 2-bromo-1-cyclopropyl-5,6-difluoro-1H-benzo[d]imidazole Int-4 (178 mg, 0.65 mmol) in DMSO (2 mL) was added 5-(difluoromethoxy)-1H-benzo[d]imidazole (120 mg, 0.65 mmol) and potassium carbonate (270 mg, 1.96 mmol) at room temperature under an inert atmosphere. The reaction mixture was heated to 100° C. and stirred for 16 h. After consumption of starting material (by TLC), the reaction mixture was diluted with ice cold water (20 mL) and extracted with EtOAc (2×20 mL). The combined organic extracts were dried over anhydrous $Na_2SO_4$ and concentrated under reduced pressure. The crude material was purified by silica gel column chromatography (eluent: 2% $MeOH/CH_2Cl_2$) followed by chiral preparative HPLC to afford 1'-cyclopropyl-5-(difluoromethoxy)-5',6'-difluoro-1'H-1,2'-bibenzo[d]imidazole Ex. 52 (15 mg, 0.04 mmol, 6%) and 1'-cyclopropyl-6-(difluoromethoxy)-5',6'-difluoro-1'H-1,2'-bibenzo[d]imidazole Ex. 53 (15 mg, 0.04 mmol, 6%) as off white solids respectively. The structures were confirmed by 2 D NMR (NOESY, COSY) studies.

Analytical Data of Ex. 52:

$^1$H NMR (400 MHz, DMSO-$d_6$): δ 8.99 (s, 1H), 7.93-7.81 (m, 3H), 7.66 (d, J=2.3 Hz, 1H), 7.50-7.09 (m, 2H), 3.75-3.69 (m, 1H), 1.06-0.98 (m, 2H), 0.71-0.64 (m, 2H)

LC-MS: m/z 377.0 [M+H]$^+$ at 3.16 RT (99.27% purity)
HPLC: 99.64%

Chiral HPLC (purity): 100.00%; $R_t$=9.02 min (Chiralpak IA, 250×4.6 mm, 5 µm); mobile phase (A) 0.1% DEA in n-hexane (B) DCM:MeOH (50:50) (A:B::80:20); flow Rate: 1.0 mL/min)

Analytical Data of Ex. 53:

$^1$H NMR (400 MHz, DMSO-$d_6$): δ 8.95 (s, 1H), 7.95-7.82 (m, 3H), 7.70 (d, J=2.3 Hz, 1H), 7.43-7.04 (m, 2H), 3.74-3.69 (m, 1H), 1.05-0.97 (m, 2H), 0.69-0.63 (m, 2H)

LC-MS: m/z 377.0 [M+H]$^+$ at 3.13 RT (99.36% purity)
HPLC: 99.74%

Chiral HPLC (purity): 99.50%; $R_t$=10.96 min (Chiralpak IA, 250×4.6 mm, 5 µm); mobile phase (A) 0.1% DEA in n-hexane (B) DCM:MeOH (50:50) (A:B::80:20); flow Rate: 1.0 mL/min)

Example 54: Metalloenzyme activity

V79-4 cells expressing recombinant andrenodoxin and andrenodoxin reductase with either recombinant human CYP11B2 or CYP11B1 were prepared according to methods previously described (LaSala et al 2009 Anal Bioch 394: 56-61). An enzyme enriched microsomal fraction was prepared from cellular lysates and subsequently used as the enzyme source for determining inhibitor $IC_{50}$s. The substrate Km values were experimentally determined for 11-deoxycorticosterone (CYP11B2 substrate) and 11-deoxycortisol (CYP11B1 substrate). Enzyme assays for inhibitor screening employed CYP11B2 and CYP11B1 enzyme enriched microsomes and were run at the Km of the respective substrates. Products of the enzyme reactions, aldosterone for CYP11B2 or cortisol for CYP11B1, were measured by LC-MS. Assays were run under conditions of less than 20% substrate turnover. Inhibitor $IC_{50}$s were generated by determining the product formation in the absence or presence of inhibitor at various concentrations. In the absence of the test compound, the product formed ($P_t$) in each data set was defined as 100% activity. In the absence of enzyme, the product formed ($P_b$) in each data set was defined as 0% activity. The percent activity in the presence of each inhibitor was calculated according to the following equation: % activity=(P-$P_b$)/($P_t$-$P_b$), where P=the product formed in the presence of the inhibitor. The $IC_{50}$ value was defined as the inhibitor concentration causing a 50% decrease in activity relative to the no inhibitor control reaction.

TABLE 2

Results: CYP11B2 Activity

| Example Number | hCYP11B2 $IC_{50}$[g] | hCYP11B1 $IC_{50}$[g] | HPLC Retention Time (min)[a] | LCMS (M + 1)[b] | Structure |
|---|---|---|---|---|---|
| 1 | ++++ | +++ | 10.35 (min)[c] | 292.9 [M + H]$^{+a}$ | 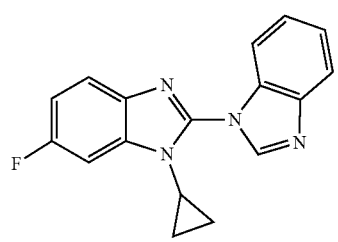 [SMILES: Fc1ccc2nc(-n3cnc4ccccc43)n(C3CC3)c2c1] |

TABLE 2-continued
Results: CYP11B2 Activity
| Example Number | hCYP11B2 IC$_{50}$[g] | hCYP11B1 IC$_{50}$[g] | HPLC Retention Time (min)[a] | LCMS (M + 1)[b] | Structure |
|---|---|---|---|---|---|
| 2 | ++++ | ++ | 9.63 (min)[b] | 310.9 [M + H]⁺[a] | 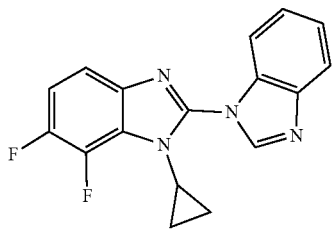 [SMILES: Fc1ccc2nc(-n3cnc4ccccc43)n(C3CC3)c2c1F] |
| 3 | ++ | + | 9.81 (min)[b] | 328.9 [M + H]⁺[a] | 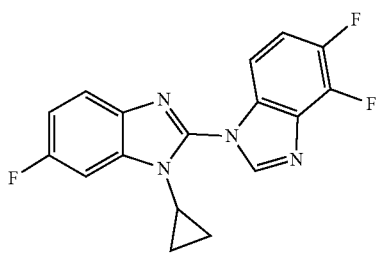 [SMILES: Fc1ccc2nc(-n3cnc4c(F)c(F)ccc43)n(C3CC3)c2c1] |
| 4 | ++++ | ++ | 9.77 (min)[b] | 328.9 [M + H]⁺[b] | 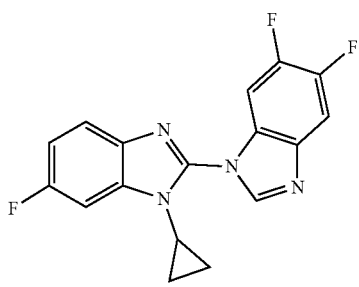 [SMILES: Fc1ccc2nc(-n3cnc4cc(F)c(F)cc43)n(C3CC3)c2c1] |
| 5 | ++++ | ++ | 7.90 (min)[b] | 353.0 [M + H]⁺[c] | 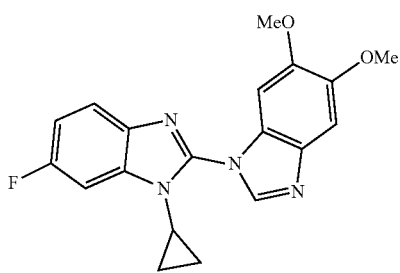 [SMILES: COc1cc2ncn(-c3nc4ccc(F)cc4n3C3CC3)c2cc1OC] |
| 6 | ++++ | ++ | 9.46 (min)[b] | 317.9 [M + H]⁺[c] | 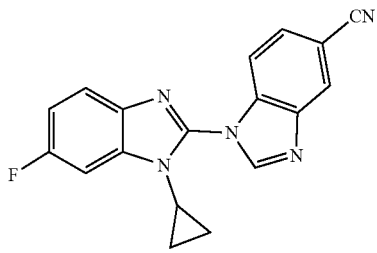 [SMILES: N#Cc1ccc2c(c1)ncn2-c1nc2ccc(F)cc2n1C1CC1] |

TABLE 2-continued

| | | | | |
|---|---|---|---|---|
| | | Results: CYP11B2 Activity | | |

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 7 | +++ | + | 9.43 (min)$^b$ | 317.9 [M + H]$^{+c}$ | 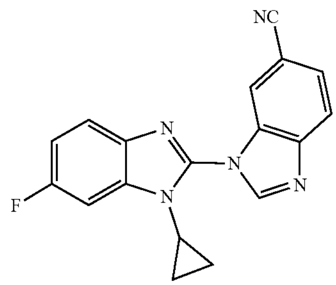 [SMILES: N#Cc1ccc2ncn(-c3nc4ccc(F)cc4n3C3CC3)c2c1] |
| 8 | ++++ | +++ | 9.57 (min)$^b$ | 306.9 [M + H]$^{+b}$ | 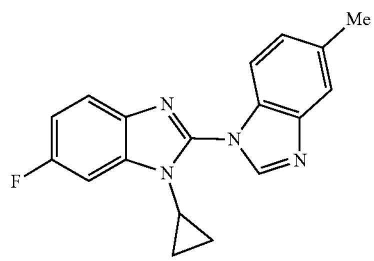 [SMILES: Cc1ccc2c(c1)ncn2-c1nc2ccc(F)cc2n1C1CC1] |
| 9 | ++++ | +++ | 9.63 (min)$^b$ | 306.9 [M + H]$^{+b}$ | 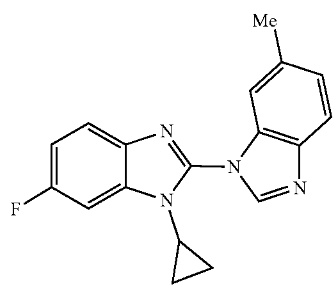 [SMILES: Cc1ccc2ncn(-c3nc4ccc(F)cc4n3C3CC3)c2c1] |
| 10 | ++++ | +++ | 10.30 (min)$^b$ | 320.9 [M + H]$^{+b}$ | 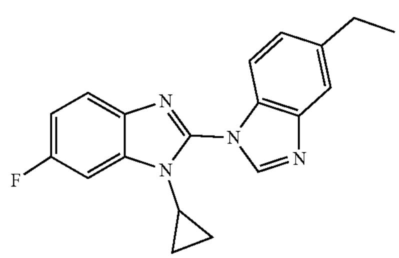 [SMILES: CCc1ccc2c(c1)ncn2-c1nc2ccc(F)cc2n1C1CC1] |
| 11 | ++++ | ++ | 10.30 (min)b | 321.0 [M + H]$^{+b}$ | 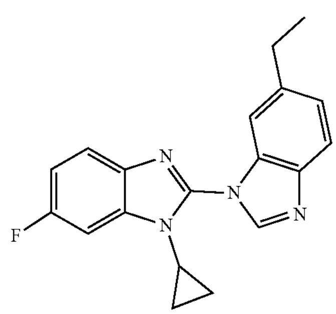 [SMILES: CCc1ccc2ncn(-c3nc4ccc(F)cc4n3C3CC3)c2c1] |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 12 | ++++ | +++ | 9.07 (min)$^b$ | 323.1 [M + H]$^{+c}$ | 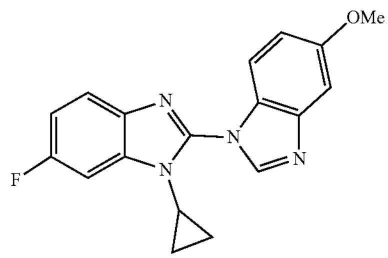 [SMILES: COc1ccc2c(c1)ncn2-c1nc2ccc(F)cc2n1C1CC1] |
| 13 | ++++ | +++ | 8.99 (min)$^b$ | 323.0 [M + H]$^{+c}$ | 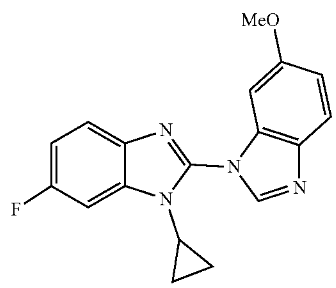 [SMILES: COc1ccc2ncn(-c3nc4ccc(F)cc4n3C3CC3)c2c1] |
| 14 | ++ | + | 9.55 (min)$^b$ | 306.9 [M + H]$^{+b}$ | 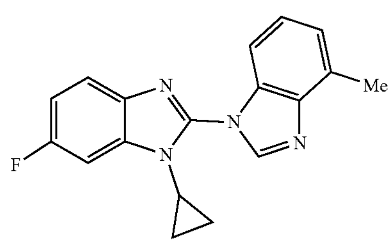 [SMILES: Cc1cccc2c1ncn2-c1nc2ccc(F)cc2n1C1CC1] |
| 15 | ++++ | ++ | 10.72 (min)$^b$ | 347.0 [M + H]$^{+c}$ | 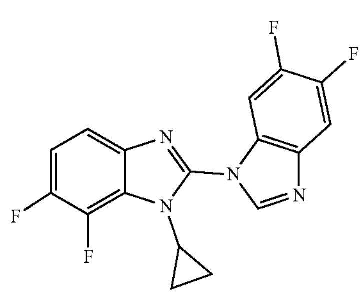 [SMILES: Fc1cc2ncn(-c3nc4ccc(F)c(F)c4n3C3CC3)c2cc1F] |
| 16 | ++++ | +++ | 9.49 (min)$^b$ | 310.9 [M + H]$^{+b}$ | 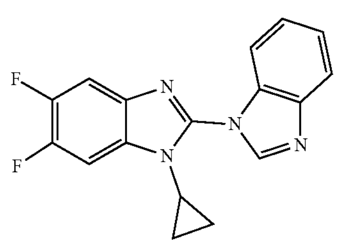 [SMILES: Fc1cc2nc(-n3cnc4ccccc43)n(C3CC3)c2cc1F] |

TABLE 2-continued
Results: CYP11B2 Activity
| Example Number | hCYP11B2 IC50[g] | hCYP11B1 IC50[g] | HPLC Retention Time (min)[a] | LCMS (M + 1)[b] | Structure |
|---|---|---|---|---|---|
| 17 | ++++ | ++ | 10.63 (min)[b] | 347.0 [M + H]+[b] | 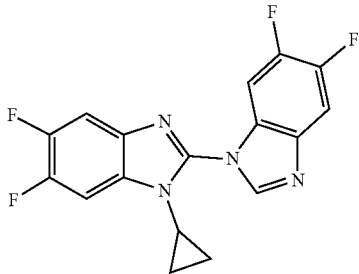 [SMILES: Fc1cc2ncn(-c3nc4cc(F)c(F)cc4n3C3CC3)c2cc1F] |
| 18 | ++++ | +++ | 9.70 (min)[b] | 310.9 [M + H]+[b] | 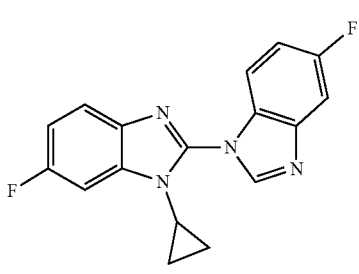 [SMILES: Fc1ccc2c(c1)ncn2-c1nc2ccc(F)cc2n1C1CC1] |
| 19 | ++++ | ++ | 9.74 (min)[b] | 310.9 [M + H]+[b] | 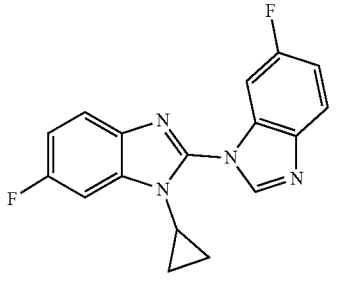 [SMILES: Fc1ccc2ncn(-c3nc4ccc(F)cc4n3C3CC3)c2c1] |
| 20 | ++++ | +++ | 10.93 (min)[b] | 360.9 [M + H]+[b] | 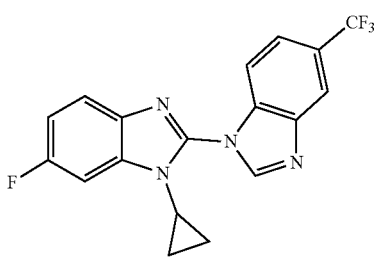 [SMILES: Fc1ccc2nc(-n3cnc4cc(C(F)(F)F)ccc43)n(C3CC3)c2c1] |
| 21 | ++++ | ++ | 10.92 (min)[b] | 361.0 [M + H]+[b] | 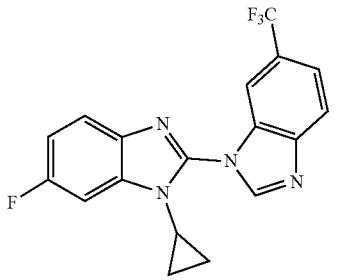 [SMILES: Fc1ccc2nc(-n3cnc4ccc(C(F)(F)F)cc43)n(C3CC3)c2c1] |

TABLE 2-continued
Results: CYP11B2 Activity
| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 22 | ++++ | ++ | 10.31 (min)$^c$ | 323.9 [M + H]$^{+b}$ | 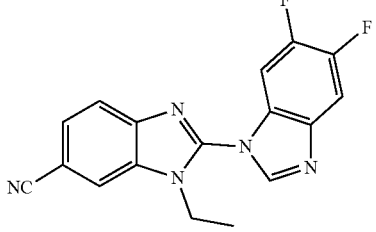 |
| 23 | ++++ | ++ | 9.77 (min)$^b$ | 336.0 [M + H]$^{+b}$ | 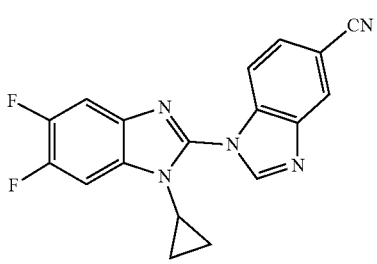 [SMILES: N#Cc1ccc2c(c1)ncn2-c1nc2cc(F)c(F)cc2n1C1CC1] |
| 24 | +++ | + | 9.73 (min)$^b$ | 335.9 [M + H]$^{+b}$ | 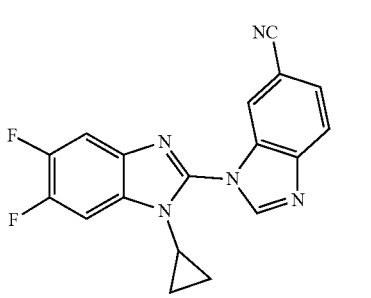 [SMILES: N#Cc1ccc2ncn(-c3nc4cc(F)c(F)cc4n3C3CC3)c2c1] |
| 25 | ++++ | ++ | 10.68 (min)$^c$ | 336.0 [M + H]$^{+b}$ | 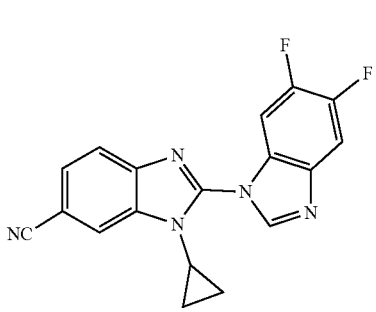 [SMILES: N#Cc1ccc2nc(-n3cnc4cc(F)c(F)cc43)n(C3CC3)c2c1] |
| 26 | ++++ | ++ | 11.49 (min)$^c$ | 344.9 [M + H]$^{+c}$ | 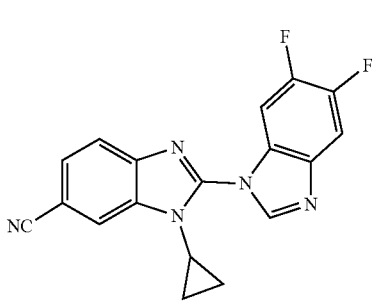 [SMILES: N#Cc1ccc2nc(-n3cnc4cc(F)c(F)cc43)n(C3CC3)c2c1] |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 27 | ++++ | +++ | 11.67 (min)$^b$ | 377.0 [M + H]$^{+b}$ | 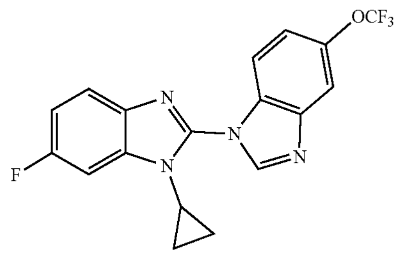 [SMILES: Fc1ccc2nc(-n3cnc4cc(OC(F)(F)F)ccc43)n(C3CC3)c2c1] |
| 28 | +++ | + | 11.67 (min)$^b$ | 377.0 [M + H]$^{+b}$ | 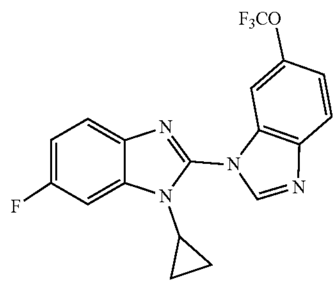 [SMILES: Fc1ccc2nc(-n3cnc4ccc(OC(F)(F)F)cc43)n(C3CC3)c2c1] |
| 29 | ++++ | ++ | 10.23 (min)$^b$ | 345.9 [M + H]$^{+b}$ | 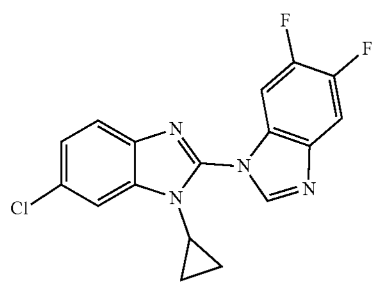 [SMILES: Fc1cc2ncn(-c3nc4ccc(Cl)cc4n3C3CC3)c2cc1F] |
| 30 | ++ | + | 9.55 (min)$^b$ | 481.9 [M + H]$^{+b}$ | 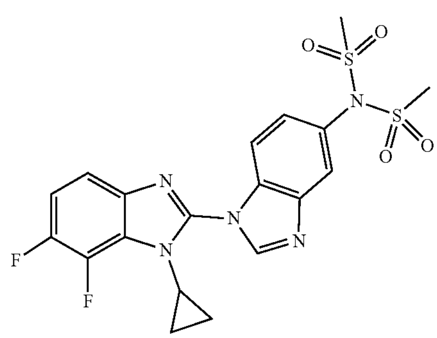 [SMILES: CS(=O)(=O)N(c1ccc2c(c1)ncn2-c1nc2ccc(F)c(F)c2n1C1CC1)S(C)(=O)=O] |
| 31 | ++++ | + | 8.53 (min)$^b$ | 404.0 [M + H]$^{+b}$ | 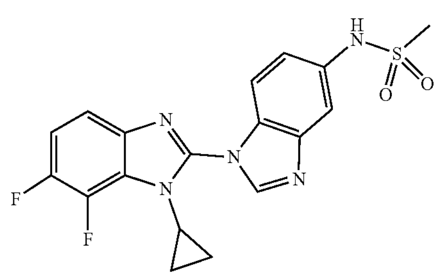 [SMILES: CS(=O)(=O)Nc1ccc2c(c1)ncn2-c1nc2ccc(F)c(F)c2n1C1CC1] |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 32 | ++++ | ++ | 9.68 (min)$^b$ | 336.9 [M + H]$^{+b}$ | 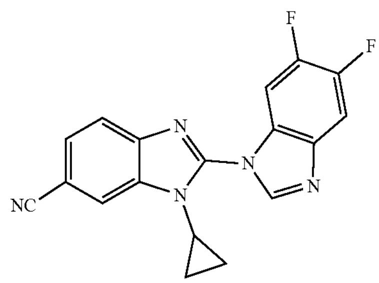 [SMILES: N#Cc1ccc2nc(-n3cnc4cc(F)c(F)cc43)n(C3CC3)c2c1] |
| 33 | ++ | + | 8.34 (min)$^b$ | 404.0 | 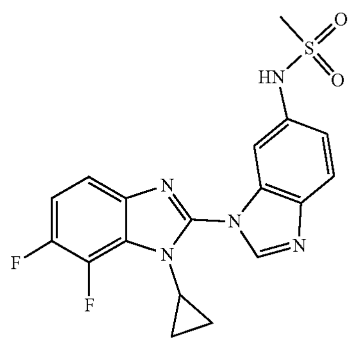 [SMILES: CS(=O)(=O)Nc1ccc2ncn(-c3nc4ccc(F)c(F)c4n3C3CC3)c2c1] |
| 34 | ++ | + | 7.86 (min)$^b$ | 311.9 [M + H]$^{+b}$ | 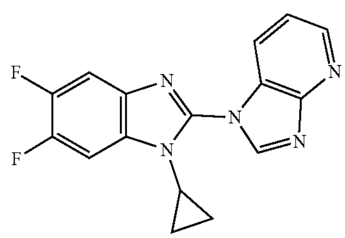 [SMILES: Fc1cc2nc(-n3cnc4ncccc43)n(C3CC3)c2cc1F] |
| 35 | ++++ | ++ | 4.93 (min)$^b$ | 311.9 [M + H]$^{+b}$ | 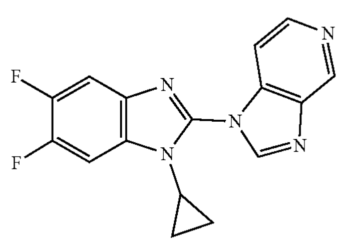 [SMILES: Fc1cc2nc(-n3cnc4cnccc43)n(C3CC3)c2cc1F] |
| 36 | ++++ | ++ | 4.89 (min)$^b$ | 311.9 [M + H]$^{+b}$ | 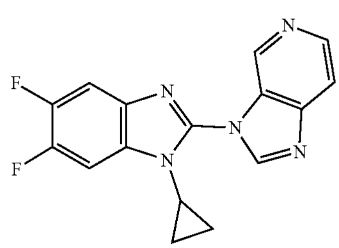 [SMILES: Fc1cc2nc(-n3cnc4ccncc43)n(C3CC3)c2cc1F] |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 37 | ++++ | ++ | 4.33 (min)$^b$ | 301.9 [M + H]$^{+b}$ | 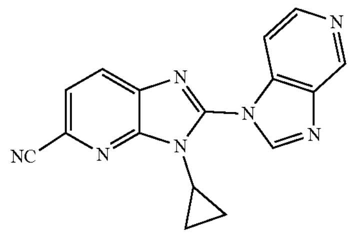 [SMILES: N#Cc1ccc2nc(-n3cnc4cnccc43)n(C3CC3)c2n1] |
| 38 | +++ | + | 4.32 (min)$^b$ | 301.9 [M + H]$^{+b}$ | 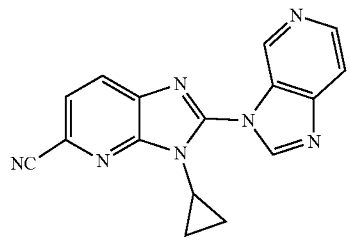 [SMILES: N#Cc1ccc2nc(-n3cnc4ccncc43)n(C3CC3)c2n1] |
| 39 | ++ | + | 6.15 (min)$^b$ | 356.2 [M + H]$^{+c}$ | 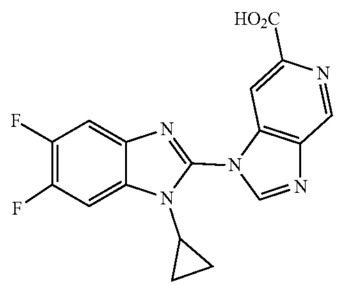 [SMILES: O=C(O)c1cc2c(cn1)ncn2-c1nc2cc(F)c(F)cc2n1C1CC1] |
| 40 | ++++ | + | 8.99 (min)$^b$ | 362.2 [M + H]$^{+c}$ | 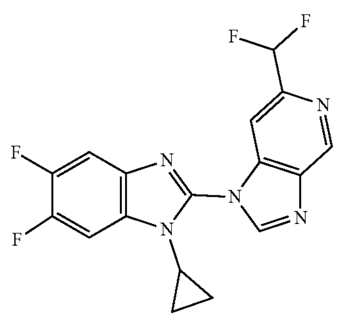 [SMILES: Fc1cc2nc(-n3cnc4cnc(C(F)F)cc43)n(C3CC3)c2cc1F] |
| 41 | ++++ | ++ | 9.24 (min)$^b$ | 361.9 [M + H]$^{+b}$ | 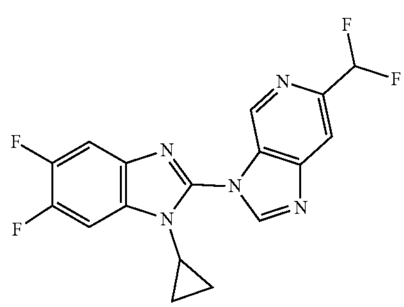 [SMILES: Fc1cc2nc(-n3cnc4cc(C(F)F)ncc43)n(C3CC3)c2cc1F] |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 42 | ++++ | + | 4.56 (min)$^b$ | 300.9 [M + H]$^{+b}$ | 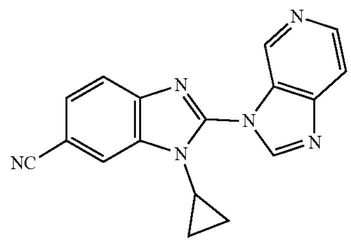 [SMILES: N#Cc1ccc2nc(-n3cnc4ccncc43)n(C3CC3)c2c1] |
| 43 | ++++ | + | 4.57 (min)$^b$ | 300.9 [M + H]$^{+b}$ | 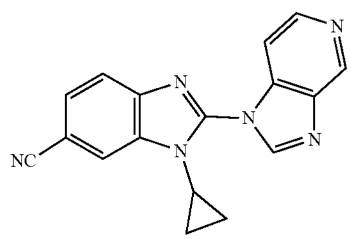 [SMILES: N#Cc1ccc2nc(-n3cnc4cnccc43)n(C3CC3)c2c1] |
| 44 | ++ | + | 8.59 (min)$^b$ | 355.2 [M + H]$^{+c}$ | 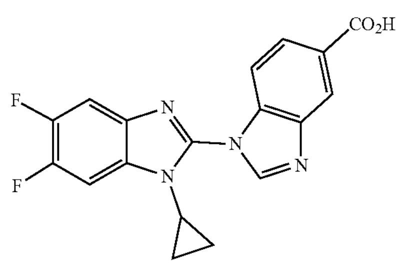 [SMILES: O=C(O)c1ccc2c(c1)ncn2-c1nc2cc(F)c(F)cc2n1C1CC1] |
| 45 | ++ | + | 8.18 (min)$^b$ | 403.9 [M + H]$^{+b}$ | 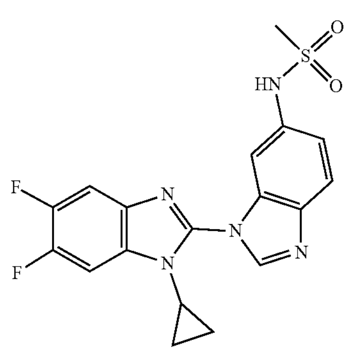 [SMILES: CS(=O)(=O)Nc1ccc2ncn(-c3nc4cc(F)c(F)cc4n3C3CC3)c2c1] |
| 46 | +++ | + | 8.39 (min)$^b$ | 404.0 [M + H]$^{+b}$ | 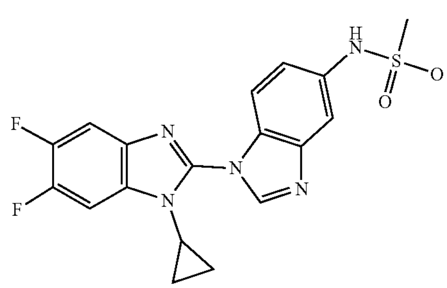 |

TABLE 2-continued

Results: CYP11B2 Activity

| Example Number | hCYP11B2 IC$_{50}$$^g$ | hCYP11B1 IC$_{50}$$^g$ | HPLC Retention Time (min)$^a$ | LCMS (M + 1)$^b$ | Structure |
|---|---|---|---|---|---|
| 47 | +++ | + | 7.22 (min)$^b$ | 393.0 [M + H]$^{+b}$ | 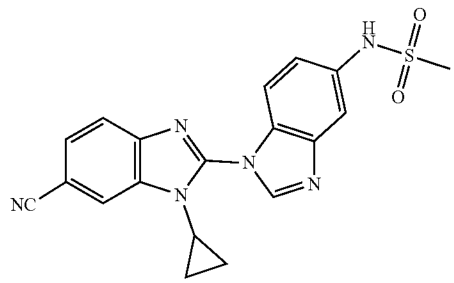 [SMILES: CS(=O)(=O)Nc1ccc2c(c1)ncn2-c1nc2ccc(C#N)cc2n1C1CC1] |
| 48 | ++ | + | 7.07 (min)$^b$ | 393.1 [M + H]$^{+b}$ | 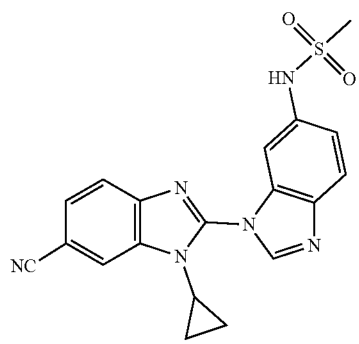 [SMILES: CS(=O)(=O)Nc1ccc2ncn(-c3nc4ccc(C#N)cc4n3C3CC3)c2c1] |
| 49 | ++++ | +++ | 9.38 (min)$^b$ | 366.2 [M + H]$^{+c}$ | 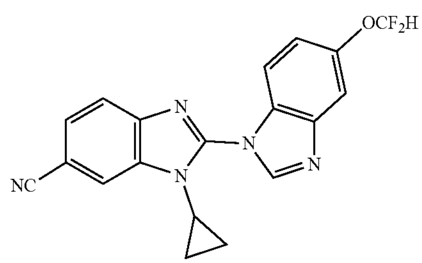 |
| 50 | ++++ | ++ | 9.26 (min)$^b$ | 366.2 [M + H]$^{+c}$ | 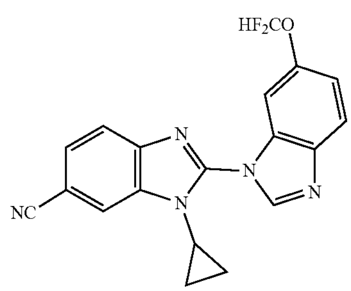 |
| 51 | | | 8.55 (min)$^b$ | 355.2 [M + H]$^{+c}$ | 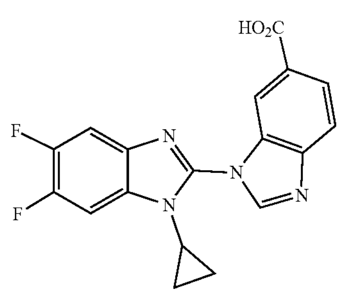 [SMILES: O=C(O)c1ccc2ncn(-c3nc4cc(F)c(F)cc4n3C3CC3)c2c1] |

TABLE 2-continued

Results: CYP11B2 Activity

| Example Number | hCYP11B2 IC$_{50}$[g] | hCYP11B1 IC$_{50}$[g] | HPLC Retention Time (min)[a] | LCMS (M + 1)[b] | Structure |
|---|---|---|---|---|---|
| 52 | ++++ | +++ | 10.54 (min)[b] | 377.0 [M + H]$^{+b}$ | 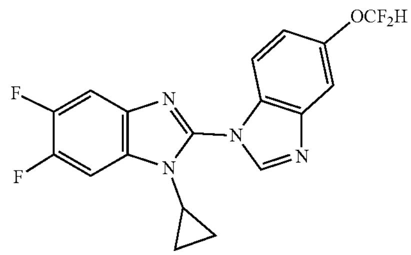 |
| 53 | ++++ | ++ | 10.43 (min)[b] | 377.0 [M + H]$^{+b}$ | 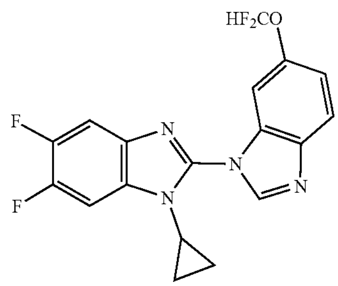 |

[f] See table 1 for HPLC and LCMS methods
[g] IC$_{50}$ ranges: + >10 µM; ++ 1-10 µM; +++ 0.1-1 µM; ++++ 0.001-0.1 µM The results in Table 2 demonstrate that compounds of Formula I are potent inhibitors of CYP11B2, and many compounds of Formula I have significant selectivity for inhibiting CYP11B2 over CYP11B1.

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:
1. A compound of Formula I:

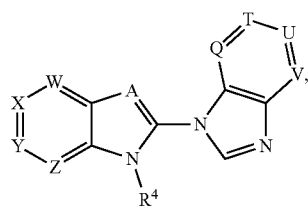

I or a pharmaceutically acceptable salt thereof; wherein
W, X, Y, and Z are each independently N or CR$^1$;
Q, T, U, and V are each independently N or CR$^2$;
A is N;
provided that no more than two of W, X, Y, and Z are N; and no more than two of Q, T, U, and V are N;
each R$^1$ is independently hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, (CR$^e$R$^f$)$_n$NR$^a$R$^b$, (CR$^e$R$^f$)$_n$NR$^c$S(O$_2$)R$^d$, (CR$^e$R$^f$)$_n$NR$^c$CO$_2$R$^d$, CO$_2$R$^e$, COR$^f$, or (CR$^e$R$^f$)$_n$OR$^f$; wherein at least one R$^1$ is halogen or cyano and any R$^1$ can be optionally substituted with 1-3 independent substituents R$^7$;
each R$^2$ is independently hydrogen, halogen, cyano, acyl, alkyl, alkenyl, alkynyl, haloalkyl, alkoxy, haloalkoxy, cycloalkyl, cycloalkoxy, aryl, arylalkyl, heteroaryl, heteroarylalkyl, heterocycloalkyl, heterocycloalkylalkyl, (CR$^e$R$^f$)$_n$NR$^a$R$^b$, (CR$^e$R$^f$)$_n$NR$^c$S(O$_2$)R$^d$, (CR$^e$R$^f$)$_n$NR$^c$CO$_2$R$^d$, N(S(O$_2$)R$^d$)$_2$, CO$_2$R$^e$, COR$^f$, or (CR$^e$R$^f$)$_n$OR$^f$; wherein any R$^2$ can be optionally substituted with 1-3 independent substituents R$^7$;
R$^3$ is hydrogen, cyano, alkyl, haloalkyl, heteroalkyl, or cycloalkyl;
R$^4$ is alkyl, cycloalkyl, haloalkyl, or heteroalkyl;
each n is independently 0, 1, 2, 3, 4, 5, 6, 7, 8, 9, or 10;
each occurrence of R$^7$ is, independently, halogen, alkyl, alkoxy, haloalkyl, carboxyl, aryl, aryl substituted with 1-3 independent halogen, —(CR$^e$R$^f$)$_n$C(O)NR$^a$R$^b$, —S(O)$_2$R$^d$, —CO$_2$R$^e$, or NR$^a$R$^b$; and
each occurrence of R$^a$, R$^b$, R$^c$, R$^d$, R$^e$, and R$^f$ are, independently, hydrogen, acyl, alkyl, alkenyl, alkynyl, heteroalkyl, haloalkyl, cycloalkyl, heterocycloalkyl, aryl, heteroaryl, alkoxyalkyl, C(O)OC$_{1-6}$ alkyl, C(O)OH, C(O)C$_{1-6}$ alkyl, S(O2)C$_{1-6}$ alkyl, S(O2)aryl, S(O₂)heteroaryl, a nitrogen protecting group when attached to a nitrogen atom, or an oxygen protecting group when attached to an oxygen atom; or $R^a$ and $R^b$ together with the atoms to which they are attached form a heterocycloalkyl ring; or $R^e$ and $R^f$ together with the atoms to which they are attached form a cycloalkyl ring; or $R^c$ and $R^d$ together with the atoms to which they are attached form a heterocycloalkyl ring.

2. The compound of claim 1, wherein the compound is of Formula I-a:

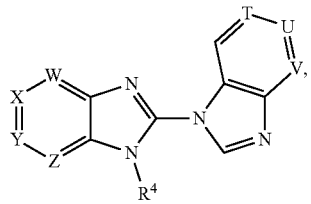

I-a or a pharmaceutically acceptable salt thereof.

3. The compound of claim 1, wherein the compound is of Formula I-b:

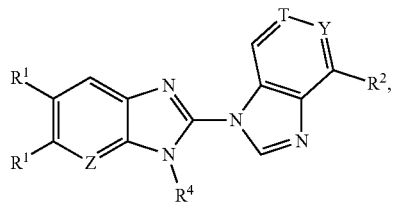

I-b or a pharmaceutically acceptable salt thereof.

4. The compound of claim 1, wherein the compound is of Formula I-c:

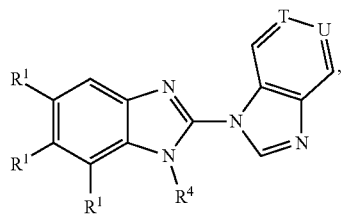

I-c or a pharmaceutically acceptable salt thereof.

5. The compound of claim 1, wherein the compound is of Formula I-d:

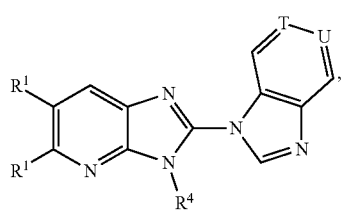

I-d or a pharmaceutically acceptable salt thereof.

6. The compound of claim 1, wherein the compound is of Formula I-e:

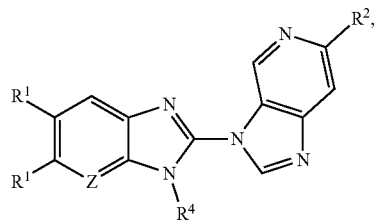

I-e or a pharmaceutically acceptable salt thereof.

7. The compound of claim 1, wherein the compound is of Formula I-f:

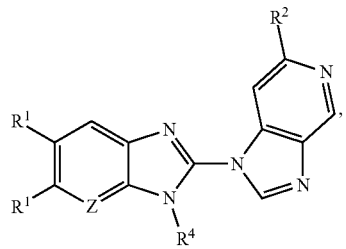

I-f or a pharmaceutically acceptable salt thereof.

8. The compound of claim 1, wherein the compound is of Formula I-g:

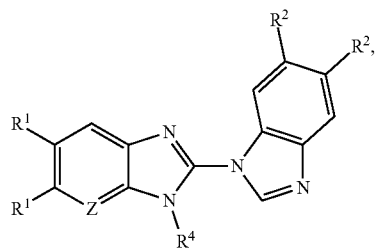

I-g or a pharmaceutically acceptable salt thereof.

9. The compound of claim 1, wherein the compound is of Formula I-h:

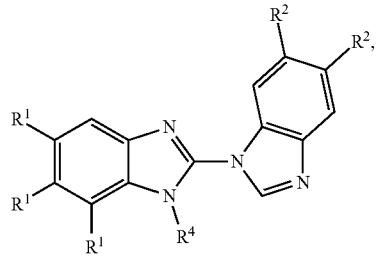

I-h or a pharmaceutically acceptable salt thereof.

10. The compound of claim 1, wherein the compound is of Formula I-i:

I-i or a pharmaceutically acceptable salt thereof.

11. The compound of claim 1, wherein the compound is of Formula I-j:

I-j or a pharmaceutically acceptable salt thereof.

12. The compound of claim 1, or a pharmaceutically acceptable salt thereof, wherein each R1 is independently hydrogen, halogen, cyano, alkyl, alkoxy, haloalkyl, or haloalkoxy.

13. The compound of claim 1, or a pharmaceutically acceptable salt thereof, wherein each $R^1$ is independently hydrogen, halogen, or cyano.

14. The compound of claim 1, or a pharmaceutically acceptable salt thereof, wherein each $R^2$ is independently hydrogen, halogen, cyano, acyl, alkyl, alkenyl, alkynyl, haloalkyl, alkoxy, haloalkoxy, cycloalkyl, cycloalkoxy, $(CR^e R^f)_n NR^a R^b$, $(CR^e R^f)_n NR^c S(O_2) R^d$, $(CR^e R^f)_n NR^c CO_2 R^d$, $CO_2 R^e$, $COR^f$, $(CR^e R^f)_n OR^f$, $NHS(O_2)R^d$, and $R^d$ is alkyl.

15. The compound of claim 1, or a pharmaceutically acceptable salt thereof, wherein no more than one of W, X, Y, and Z is N.

16. The compound of claim 1, or a pharmaceutically acceptable salt thereof, wherein W, X, Y, and Z are each $CR^1$.

17. The compound of claim 1, or a pharmaceutically acceptable salt thereof, wherein no more than one of Q, T, U, and V is N, or wherein Q, T, U, and V are each $CR^2$.

18. The compound of claim 1, or a pharmaceutically acceptable salt thereof, wherein: each $R^1$ is independently hydrogen, halogen, or cyano; and $R^4$ is cyclopropyl.

19. The compound of claim 1, wherein the compound is
1'-Cyclopropyl-6'-fluoro-1'H-1,2'-bibenzo[d]imidazole (1);
1'-Cyclopropyl-6',7'-difluoro-1'H-1,2'-bibenzo[d]imidazole (2);
1'-Cyclopropyl-4,5,6'-trifluoro-1'H-1,2'-bibenzo[d]imidazole (3);
1'-Cyclopropyl-5,6,6'-trifluoro-1'H-1,2'-bibenzo[d]imidazole (4);
1'-Cyclopropyl-6'-fluoro-5,6-dimethoxy-1'H-1,2'-bibenzo[d] imidazole (5);
1'-Cyclopropyl-6'-fluoro-1'H-[1,2'-bibenzo[d]imidazole[-5-carbonitrile (6);
1'-Cyclopropyl-6'-fluoro-1'H-[1,2'-bibenzo[d]imidazole[-6-carbonitrile (7);
1'-Cyclopropyl-6'-fluoro-5-methyl-1'H-1,2'-bibenzo[d] imidazole (8);
1'-Cyclopropyl-6'-fluoro-6-methyl-1'H-1,2'-bibenzo[d] imidazole (9);
1'-Cyclopropyl-5-ethyl-6'-fluoro-1'H-1,2'-bibenzo[d]imidazole (10);
1'-Cyclopropyl-6-ethyl-6'-fluoro-1'H-1,2'-bibenzo[d]imidazole (11);
1'-Cyclopropyl-6'-fluoro-5-methoxy-1'H-1,2'-bibenzo[d] imidazole (12);
1'-Cyclopropyl-6'-fluoro-6-methoxy-1'H-1,2'-bibenzo[d] imidazole (13);
1'-Cyclopropyl-6'-fluoro-4-methyl-1'H-1,2'-bibenzo[d] imidazole (14);
1'-Cyclopropyl-5,6,6',7'-tetrafluoro-1'H-1,2'-bibenzo[d] imidazole (15);
1'-Cyclopropyl-5',6'-difluoro-1'H-1,2'-bibenzo[d]imidazole (16);
1'-Cyclopropyl-5,5',6,6'-tetrafluoro-1'H-1,2'-bibenzo[d] imidazole (17);
1'-Cyclopropyl-5,6'-difluoro-1'H-1,2'-bibenzo[d]imidazole (18);
1'-Cyclopropyl-6,6'-difluoro-1'H-1,2'-bibenzo[d]imidazole (19);
1'-Cyclopropyl-6'-fluoro-5-(trifluoromethyl)-1'H-1,2'-bibenzo[d]imidazole (20);
1'-Cyclopropyl-6'-fluoro-6-(trifluoromethyl)-1'H-1,2'-bibenzo[d]imidazole (21);
1'-ethyl-5,6-difluoro-1'H-[1,2'-bibenzo[d]imidazole]-6'-carbonitrile (22);
1'-Cyclopropyl-5',6'-difluoro-1'H-[1,2'-bibenzo[d]imidazole]-5-carbonitrile (23);
1'-Cyclopropyl-5',6'-difluoro-1'H-[1,2'-bibenzo[d]imidazole]-6-carbonitrile (24);
1'-Cyclopropyl-5,6-difluoro-1'H-[1,2'-bibenzo[d]imidazole]-6'-carbonitrile (25);
6'-Chloro-1'-cyclopropyl-5,6-difluoro-1'H-1,2'-bibenzo [d] imidazole (26);
1'-Cyclopropyl-6'-fluoro-5-(trifluoromethoxy)-1'H-1,2'-bibenzo [d] imidazole (27);
1'-Cyclopropyl-6'-fluoro-6-(trifluoromethoxy)-1'H-1,2'-bibenzo [d] imidazole (28);
5-Chloro-3-cyclopropyl-2-(5,6-difluoro-1H-benzo [d] imidazol-1-yl)-3H-imidazo[4,5 b]pyridine (29);
N-(1'-cyclopropyl-6',7'-difluoro-1'H-[1,2'-bibenzo [d]imidazol]-5-yl)-N (methylsulfonyl) methanesulfonamide (30);
N-(1'-cyclopropyl-6',7'-difluoro-1'H-[1,2'-bibenzo[d]imidazol]-5-yl) methanesulfonamide (31);
3-Cyclopropyl-2-(5,6-difluoro-1H-benzo[d]imidazol-1-yl)-3H-imidaz[4,5-b]pyridine-5-carbonitrile (32);
N-(1'-cyclopropyl-6',7'-difluoro-1'H-[1,2'-bibenzo[d]imidazol]-6-yl) methanesulfonamide (33);
1-(1-Cyclopropyl-5,6-difluoro-1H-benzo[d]imidazol-2-yl)-1H-imidazo[4,5-b]pyridine (34);
1-(1-Cyclopropyl-5,6-difluoro-1H-benzo [d]imidazol-2-yl)-1H-imidazo[4,5-c]pyridine (35);
3-(1-Cyclopropyl-5,6-difluoro-1H-benzo [d] imidazol-2-yl)-3H-imidazo[4,5-c]pyridine (36);

3-cyclopropyl-2-(3H-imidazo[4,5-c]pyridin-3-yl)-3H-imidazo[4,5-b]pyridine-5 carbonitrile (37); 3-cyclopropyl-2-(1H-imidazo[4,5-c]pyridin-1-yl)-3H-imidazo[4,5-b]pyridin 5-carbonitrile (38);

1-(1-Cyclopropyl-5,6-difluoro-1H-benzo [d] imidazol-2-yl)-1H-imidazo[4,5-c]pyridine 6-carboxylic acid (39);

1-(1-Cyclopropyl-5,6-difluoro-1H-benzo [d] imidazol-2-yl)-6-(difluoromethyl)-1H imidazo[4,5-c]pyridine (40);

3-(1-Cyclopropyl-5,6-difluoro-1H-benzo [d] imidazol-2-yl)-6-(difluoromethyl)-3H imidazo[4,5-c]pyridine (41);

1-Cyclopropyl-2-(3H-imidazo[4,5-c]pyridin-3-yl)-1H-benzo[d]imidazole-6 carbonitrile (42);

1-Cyclopropyl-2-(1H-imidazo[4,5-c]pyridin-1-yl)-1H-benzo[d]imidazole-6 carbonitrile (43);

1'-Cyclopropyl-5',6'-difluoro-1'H-[1,2'-bibenzo[d]imidazole]-5-carboxylic acid (Ex. 44);

N-(1'-Cyclopropyl-5',6'-difluoro-1'H-[1,2'-bibenzo[d]imidazol]-6 yl) methanesulfonamide (45);

N-(1'-Cyclopropyl-5',6'-difluoro-1'H-[1,2'-bibenzo[d]imidazol]-5-yl) methanesulfonamide (46);

N-(6'-Cyano-1'-cyclopropyl-1'H-[1,2'-bibenzo[d] imidazol]-5-yl) methanesulfonamide (47);

N-(6'-Cyano-1'-cyclopropyl-1'H-[1,2'-bibenzo[d]imidazol]-6-yl) methanesulfonamide (48);

1'-Cyclopropyl-5-(difluoromethoxy)-1'H-[1,2'-bibenzo[d]imidazole]-6'-carbonitrile (49);

1'-Cyclopropyl-6-(difluoromethoxy)-1'H-[1,2'-bibenzo[d]imidazole]-6'-carbonitrile (50);

1'-Cyclopropyl-5',6'-difluoro-1'H-[1,2'-bibenzo[d]imidazole]-6-carboxylic acid (51);

1'-Cyclopropyl-5-(difluoromethoxy)-5',6'-difluoro-1'H-1,2'-bibenzo[d]imidazole (52);

1'-Cyclopropyl-6-(difluoromethoxy)-5',6'-difluoro-1'H-1,2'-bibenzo[d]imidazole (53); or a pharmaceutically acceptable salt thereof.

20. The compound of claim 1, or a pharmaceutically acceptable salt thereof, wherein:

each $R^1$ is independently hydrogen, halogen, or cyano; wherein at least one $R^1$ is halogen or cyano;

each $R^2$ is independently hydrogen, halogen, cyano, alkyl, haloalkyl, alkoxy, haloalkoxy, or $(CR^eR^f)_nNR^cS(O_2)R^d$; and $R^4$ is cyclopropyl.

* * * * *